US012427197B2

(12) United States Patent
Lindley et al.

(10) Patent No.: US 12,427,197 B2
(45) Date of Patent: Sep. 30, 2025

(54) METHODS OF PRODUCING COBALT NANOPARTICLES AND HOLLOW METAL NANOSPHERES

(71) Applicant: The Regents of the University of California, Oakland, CA (US)

(72) Inventors: Sarah Lindley, Santa Cruz, CA (US); Jin Zhang, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 918 days.

(21) Appl. No.: 16/493,677

(22) PCT Filed: Mar. 15, 2018

(86) PCT No.: PCT/US2018/022713
§ 371 (c)(1),
(2) Date: Sep. 12, 2019

(87) PCT Pub. No.: WO2018/170304
PCT Pub. Date: Sep. 20, 2018

(65) Prior Publication Data
US 2020/0129619 A1    Apr. 30, 2020

Related U.S. Application Data

(60) Provisional application No. 62/636,824, filed on Feb. 28, 2018, provisional application No. 62/471,401, filed on Mar. 15, 2017.

(51) Int. Cl.
*B22F 9/24*    (2006.01)
*A61K 33/242*    (2019.01)
(Continued)

(52) U.S. Cl.
CPC ........ *A61K 41/0052* (2013.01); *A61K 33/242* (2019.01); *A61K 47/51* (2017.08);
(Continued)

(58) Field of Classification Search
None
See application file for complete search history.

(56) References Cited

U.S. PATENT DOCUMENTS 6,262,129 B1    7/2001 Murray et al.
2006/0003163 A1*   1/2006 Mayes .................. H01F 1/44
428/407

(Continued)

FOREIGN PATENT DOCUMENTS

DE        10214226        6/2016

OTHER PUBLICATIONS

Gomez, L. et al., "Scaled-up production of plasmonic nanoparticles using microfluidics: from metal precursors to functionalized and sterilized nanoparticles", Lab on a Chip, vol. 14, pp. 325-332, published Sep. 30, 2013.*

(Continued)

*Primary Examiner* — George Wyszomierski
(74) *Attorney, Agent, or Firm* — Brian E. Davy; Bozicevic, Field & Francis LLP

(57) ABSTRACT

Provided are methods of producing cobalt-based nanoparticles ($Co_xB_y$ NPs) of a pre-selected diameter. The methods include reducing $Co^{2+}$ ions with a sodium borohydride ($NaBH_4$) solution having a selected ratio of tetrahydroxyborate ($B(OH)_4^-$) to tetrahydroborate ($BH_4^-$) based on the pre-selected diameter, where the ratio of $B(OH)_4^-$ to $BH_4^-$ is positively correlated with the pre-selected diameter. Also provided are methods of using the $Co_xB_y$ NPs to produce hollow metal nanospheres (HMNs). Methods of producing $Co_xB_y$ NP core/metal shell structures are also provided, such methods including combining in an anaerobic galvanic exchange reaction a deaerated solution including $Co_xB_y$ NP scaffolds and a deaerated solution including a metal. Also provided are methods of producing HMNs from the $Co_xB_y$ NP core/metal shell structures. Compositions and kits that (Continued)

find use in practicing the methods of the present disclosure and using HMNs produced in accordance with the methods of the present disclosure, are also provided.

15 Claims, 39 Drawing Sheets

(51) Int. Cl.
  *A61K 41/00* (2020.01)
  *A61K 47/51* (2017.01)
  *C01B 35/04* (2006.01)
(52) U.S. Cl.
  CPC ............... *B22F 9/24* (2013.01); *C01B 35/04* (2013.01); *C01P 2002/82* (2013.01); *C01P 2002/85* (2013.01); *C01P 2002/86* (2013.01); *C01P 2004/03* (2013.01); *C01P 2004/04* (2013.01); *C01P 2004/34* (2013.01)

(56) References Cited

U.S. PATENT DOCUMENTS

| | | | | |
|---|---|---|---|---|
| 2009/0263485 | A1* | 10/2009 | Li | A61P 35/00 424/489 |
| 2010/0009338 | A1* | 1/2010 | Zhang | H01L 29/0673 435/5 |
| 2013/0177838 | A1* | 7/2013 | Wang | B01J 23/52 429/524 |
| 2017/0037494 | A1* | 2/2017 | Kuttiyiel | B22F 1/0018 |

OTHER PUBLICATIONS

Adams et al. (2014) "Key Factors Affecting the Reproducibility of Synthesis and Growth Mechanism of Near-Infrared Absorbing Hollow Gold Nanospheres" Chem. Mater., 26:6805-6810.
Adams et al. (2016) "Unique Optical Properties and Applications of Hollow Gold Nanospheres (HGNs)" Coord. Chem. Rev., 320-321:18-37.
An and Hyeon (2009) "Synthesis and Biomedical Applications of Hollow Nanostructures" Nano Today, 4:359-373.
Chen and Gao (2006) "Synthesis and Characterization of Ag Nanoshells by a Facile Sacrificial Template Route through in situ Replacement Reaction" Inorg. Chem. 45:5145-5149.
Chen et al. (2009) "Size Controlled Synthesis of Co Nanoparticles by Combination of Organic Solvent and Surfactant" Appl. Surf. Sci., 255:4039-4044.
Dávila-Ibáñez et al. (2011) "Amorphous Tunable-Size Co—B Magnetic Nanoparticles from the Cobalt-Catalyzed NaBH4 Hydrolysis" Phys. Chem. Chem. Phys., 13:20146-20154.
Genç et al. (2017) "Hollow Metal Nanostructures for Enhanced Plasmonics: Synthesis, Local Plasmonic Properties, and Applications" Nanophotonics, 6:193-213.
Glavee et al. (1992) "Borohydride Reductions of Metal Ions. A New Understanding of the Chemistry Leading to Nanoscale Particles of metals, Borides, and Metal Borates" Langmuir, 8:771-773.
Glavee et al. (1993) "Borohydride Reduction of Cobalt Ions in Water. Chemistry Leading to Nanoscale Metal, Boride, or Borate Particles" Langmuir, 9:162-169.
Liang et al. (2004) "Pt Hollow Nanospheres: Facile Synthesis and Enhanced Electrocatalyts" Angew. Chem. Int. Ed. 43:1540-1543.
Liang et al. (2005) "Gold Hollow Nanospheres: Tunable Surface Plasmon Resonance Controlled by Interior-Cavity Sizes" J. Phys. Chem. B., 109:7795-7800.
Lu et al. (2011) "Effects of Photoacoustic Imaging and Photothermal Ablation Therapy Mediated by Targeted Hollow Gold Nanospheres in an Orthotopic Mouse Xenograft Model of Glioma" Cancer Res., 71:6116-6121.
Netskina et al. (2016) "Aqueous-alkaline NaBH4 solution: The influence of storage duration of solutions on reduction and activity of cobalt catalysts" Renewable Energy, 99: 1073-1081.
Polte et al. (2010) "Nucleation and Growth of Gold Nanoparticles Studied viain situ Small Angle X-ray Scattering at Millisecond Time Resolution" ACS Nano, 4(2): 1076-1082.
Polte et al. (2012) "Formation Mechanism of Colloidal Silver Nanoparticles: Analogies and Differences to the Growth of Gold Nanoparticles" ACS Nano, 6(7): 5791-5802.
Preciado-Flores et al. (2011) "Highly Reproducible Synthesis of Hollow Gold Nanospheres with Near Infrared Surface Plasmon Absorption Using PVP as a Stabilizing Agent" J. Mater. Chem., 2344-2350.
Pu et al. (2017) "Size-Tunable Synthesis of Hollow Gold Nanospheres through Control of Reaction Temperature" Part. Part. Syst. Charact., 34:1600255.
Schwartzberg et al. (2006) "Synthesis, Characterization, and Tunable Optical Properties of Hollow Gold Nanospheres" J. Phys. Chem. B., 110:19935-19944.
Thanh et al. (2014) "Mechanisms of Nucleation and Growth of Nanoparticles in Solution" Chem. Rev., 114:7610-7630.
Van Hyning et al. (1998) "Formation Mechanisms and Aggregation Behavior of Borohydride Reduced Silver Particles" Langmuir, 14(24): 7034-7046.
Van Hyning et al. (2001) "Characterization of Colloidal Stability during Precipitation Reactions" Langmuir, 17:3120-3127.
Van Hyning et al. (2001) "Silver Nanoparticle Formation: Predictions and Verification of the Aggregative Growth Model" Langmuir, 17:3128-3135.
Wuithschick et al. (2013) "Size-Controlled Synthesis of Colloidal Silver Nanoparticles Based on Mechanistic Understanding" Chem. of Mat., 25:4679-4689.
Zhao et al. (2011) "Formation of hollow Ag/Au nanostructures in seeding approach: The competition of hydroxyl groups with chloride ions to Ag" Colloids and Surfaces A: Physicochem. Eng. Aspects, 386:172-178.
Holbrook et al. (1971) "Hydrolysis of the Borohydride Ion catalysed by Metal-Boron Alloys" J. Chem. Soc. A, 890-894.
Lindley et al. (2018) "Highly Tunable Hollow Gold Nanospheres: Gaining Size Control and Uniform Galvanic Exchange of Sacrificial Cobalt Boride Scaffolds" ACS Appl. Mater. Interfaces, 10(15):12992-13001.
Masa et al. (2016) "Amorphous Cobalt Boride (Co2B) as a Highly Efficient Nonprecious Catalyst for Electrochemical Water Splitting: Oxygen and Hydrogen Evolution" Adv. Energy Mater, 6:1502313.

* cited by examiner

FIG. 1
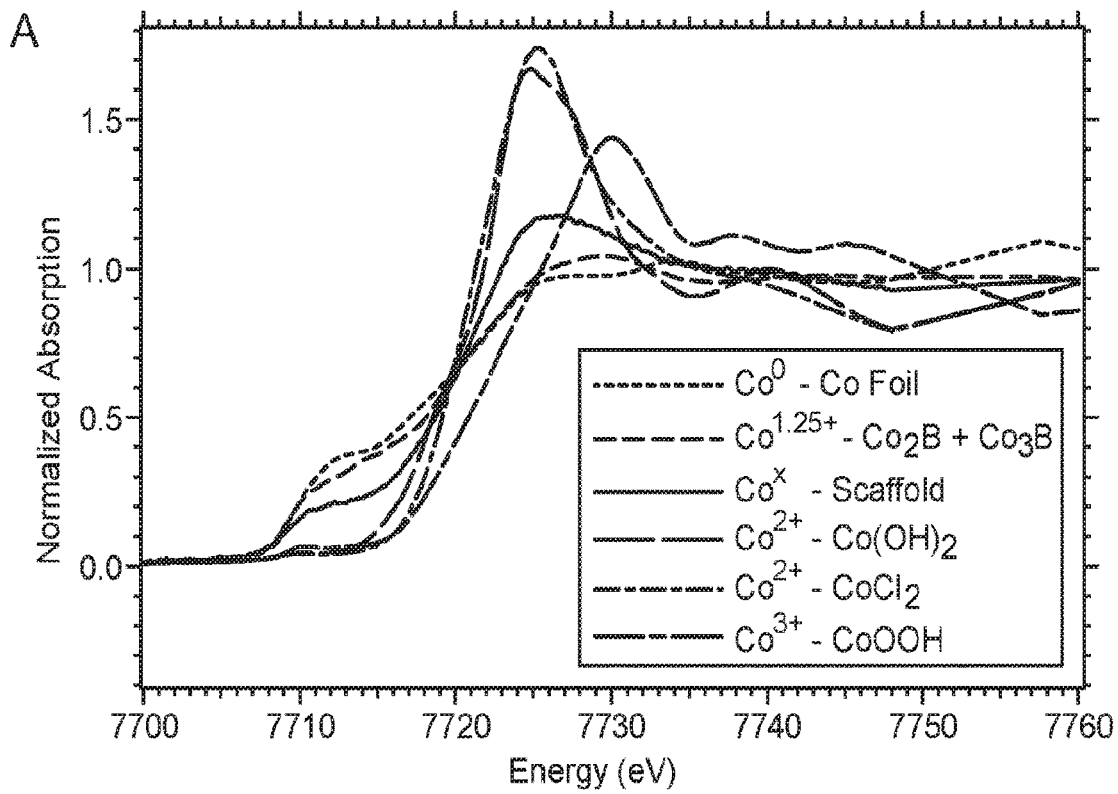
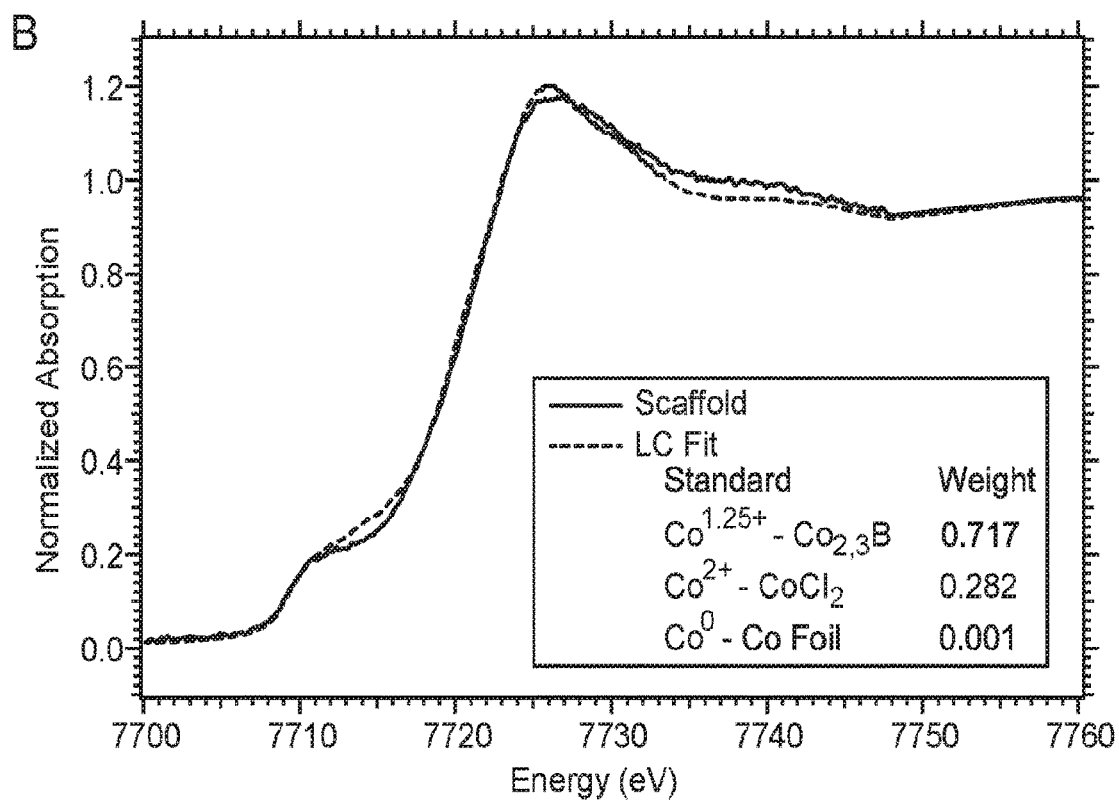

FIG. 2 (Cont.)
B
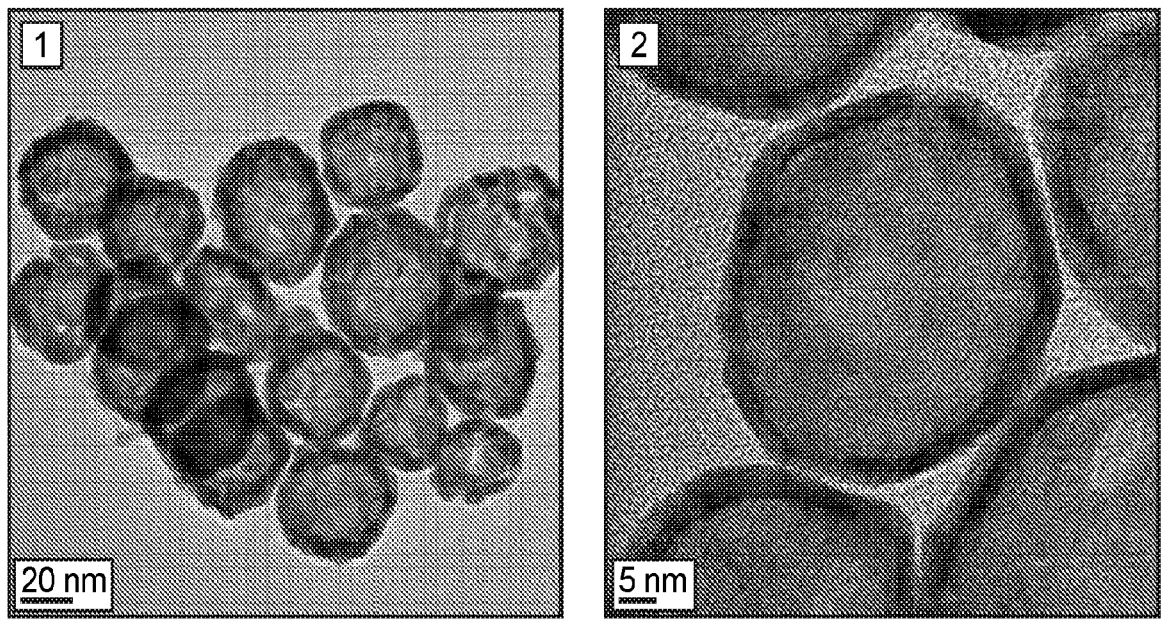
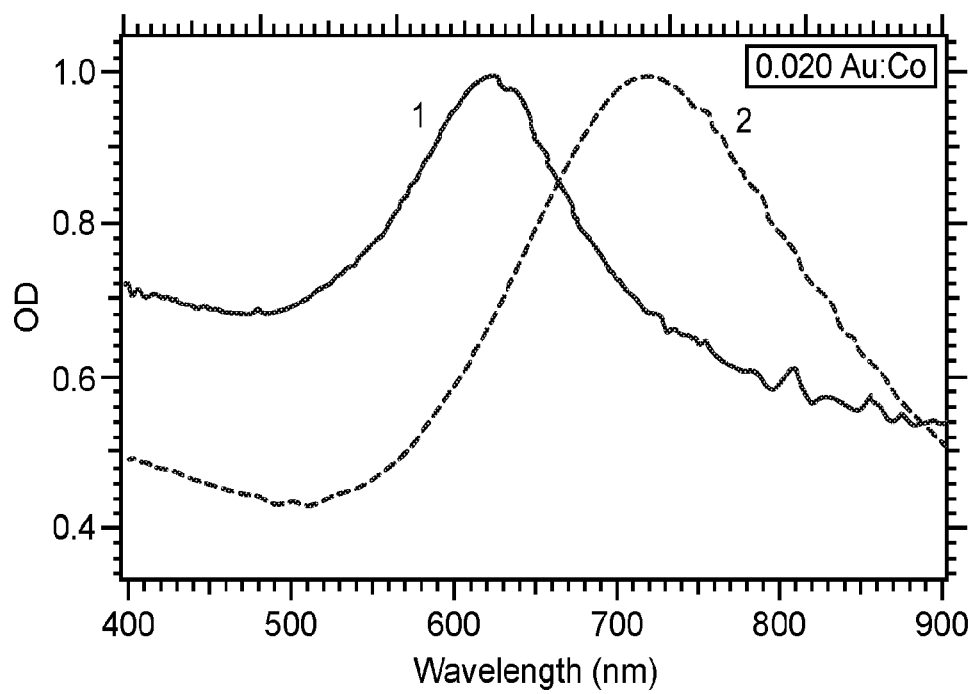

FIG. 4
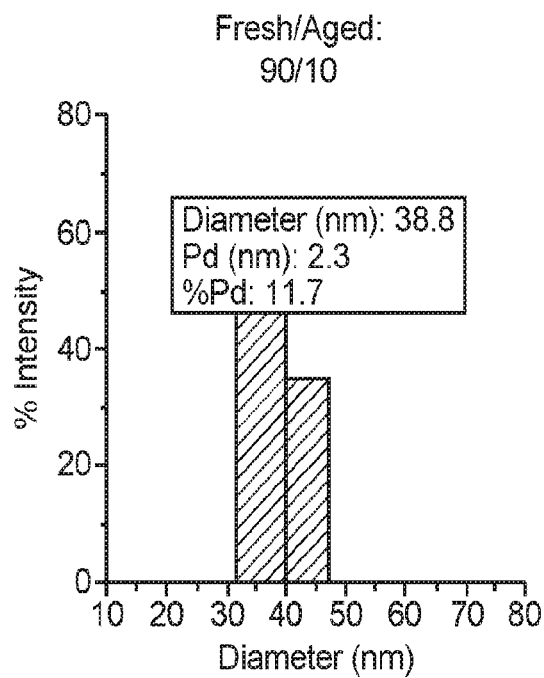
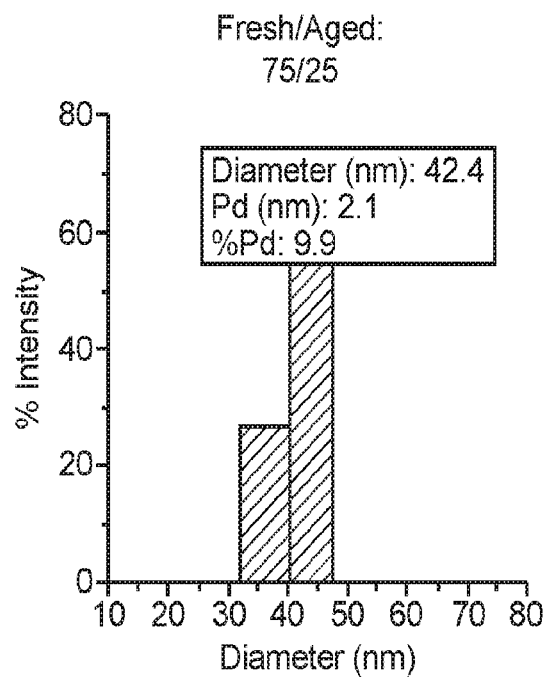
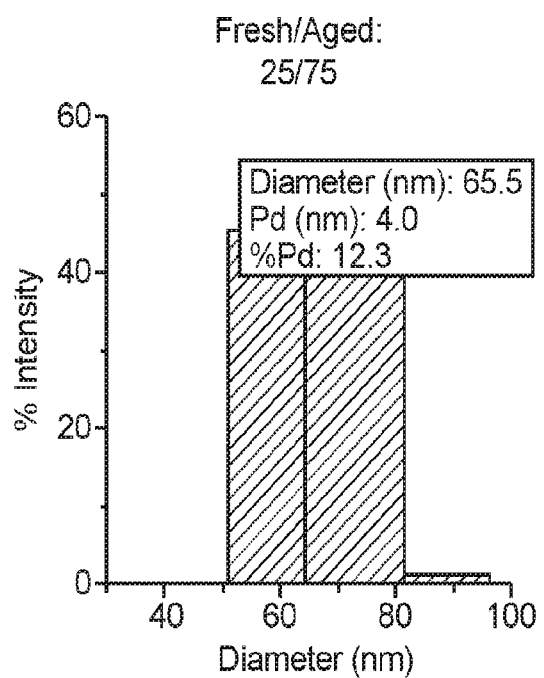
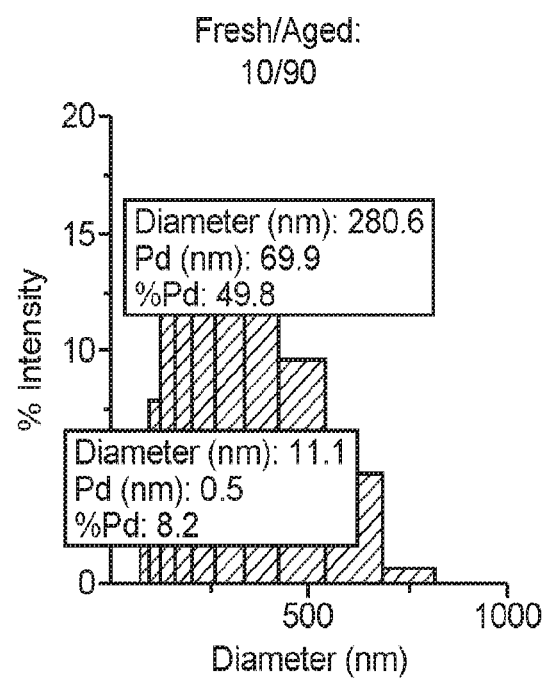

FIG. 5
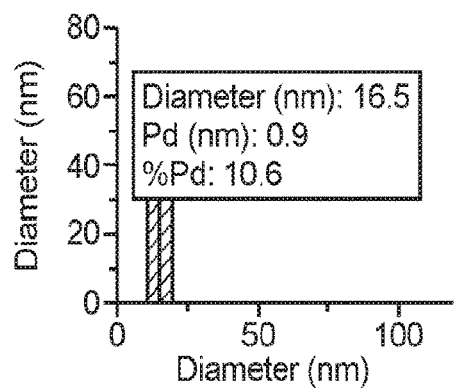
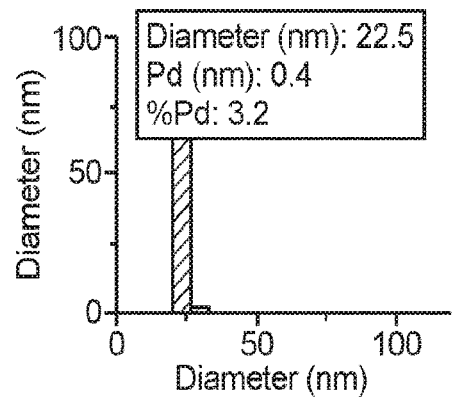
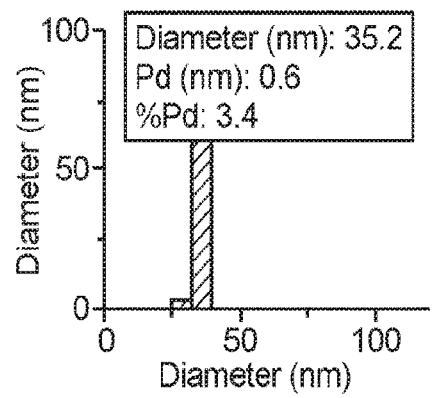
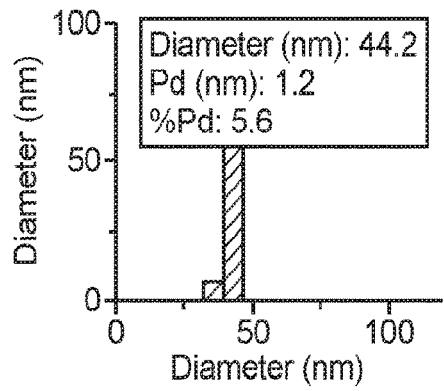
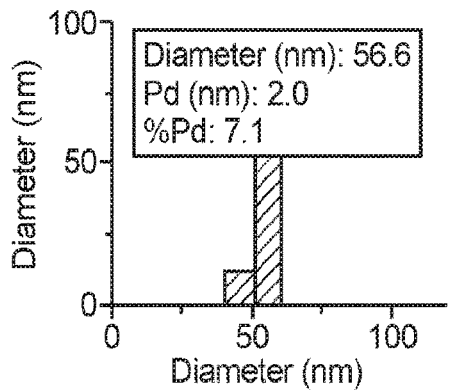
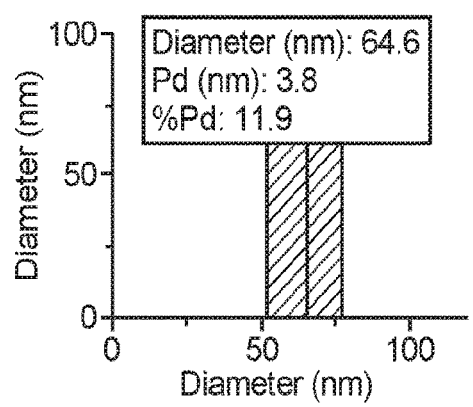
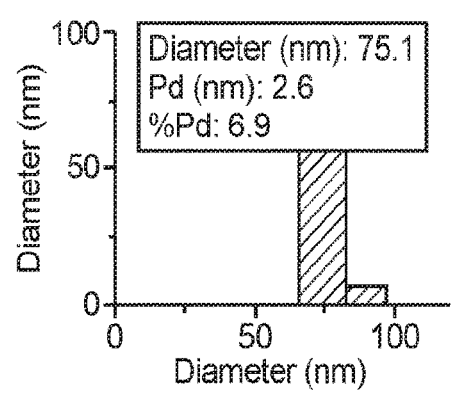
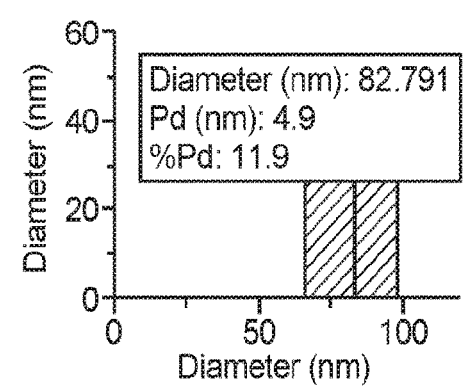

FIG. 6
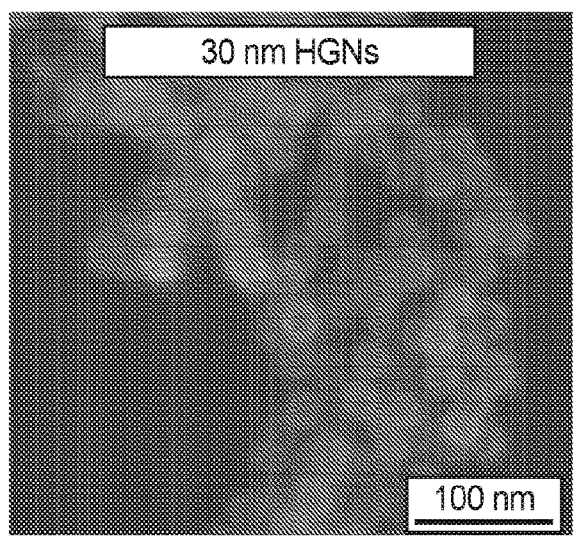
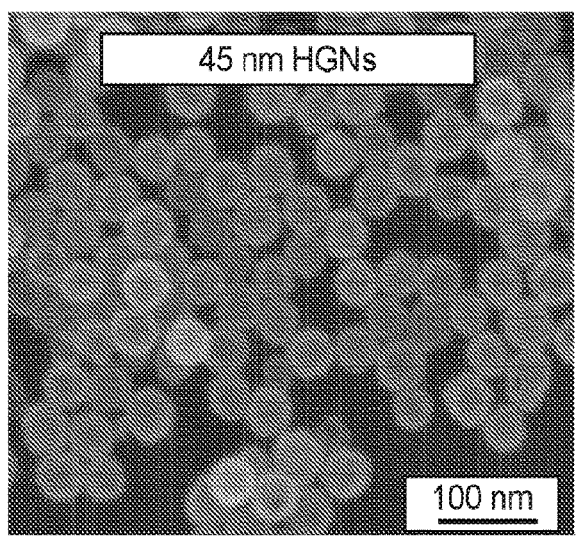
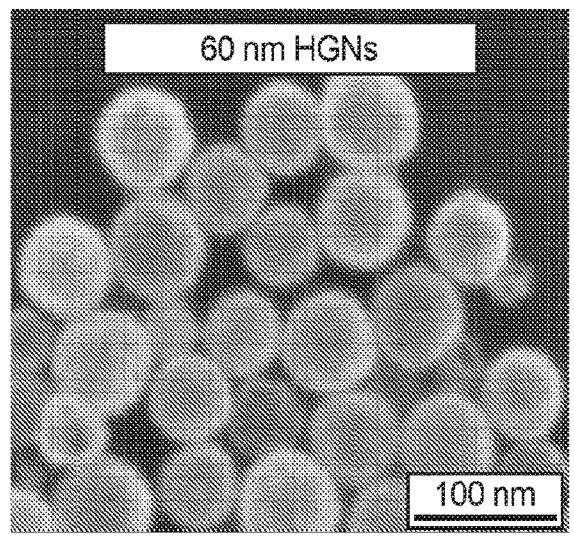

FIG. 8
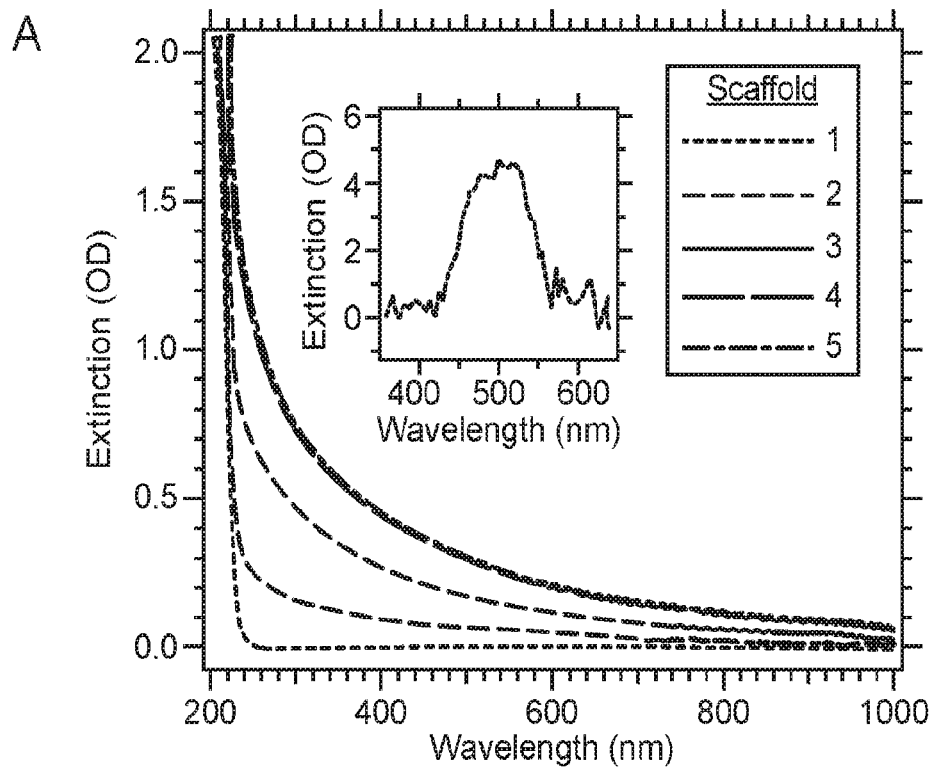
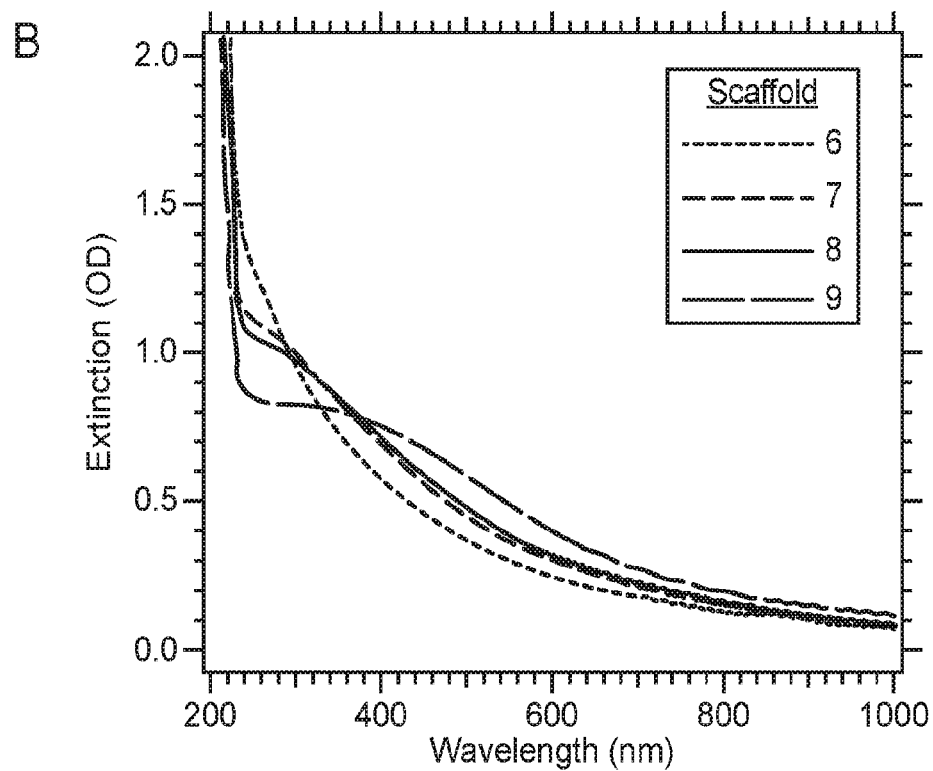

FIG. 9
Scaffold 5: 23 ± 3 nm
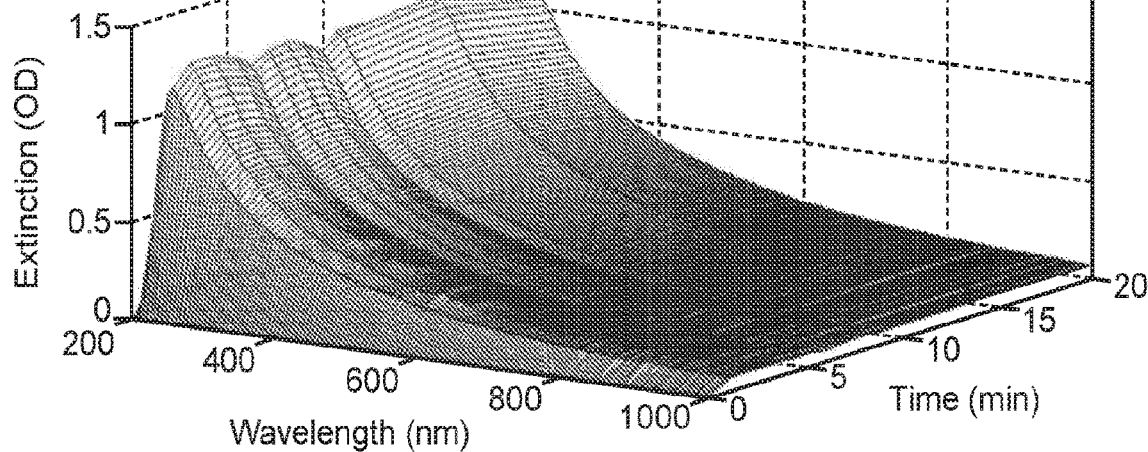
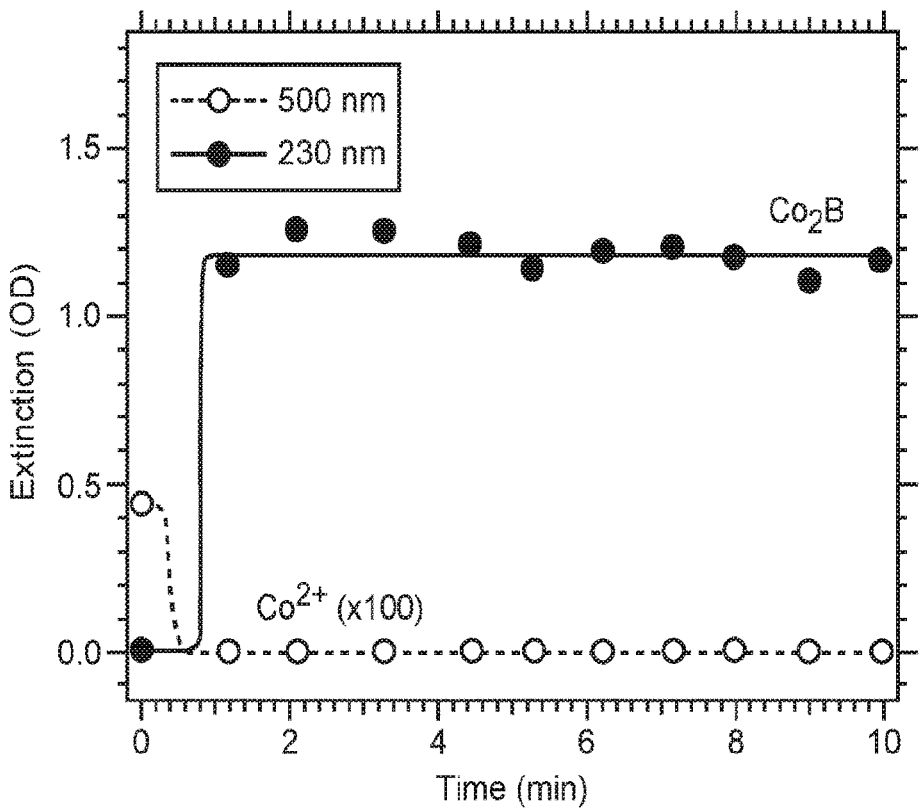

FIG. 9 (Cont.)
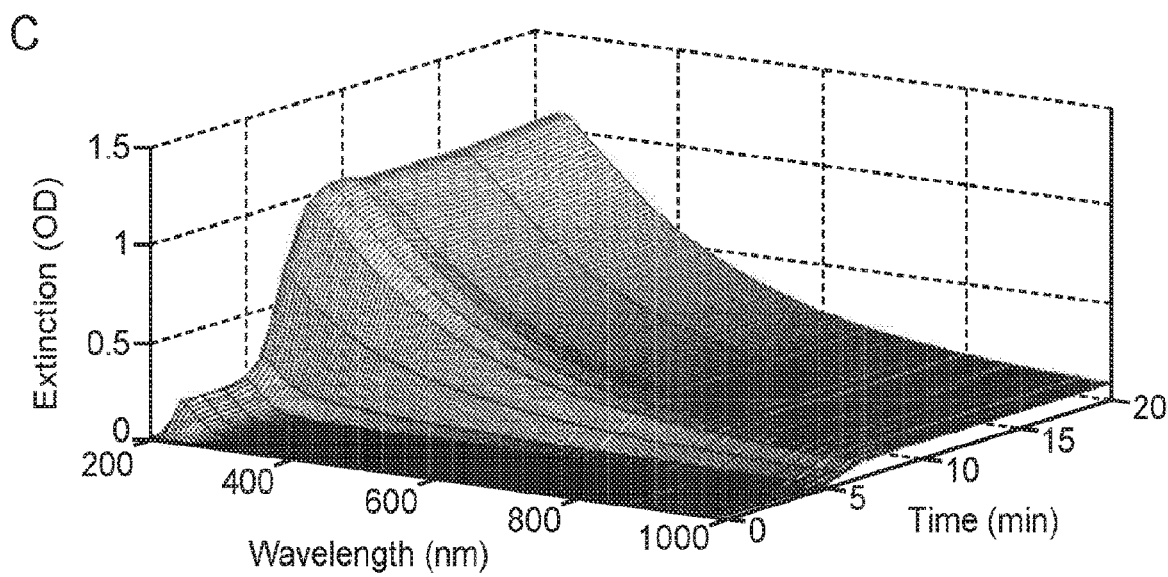
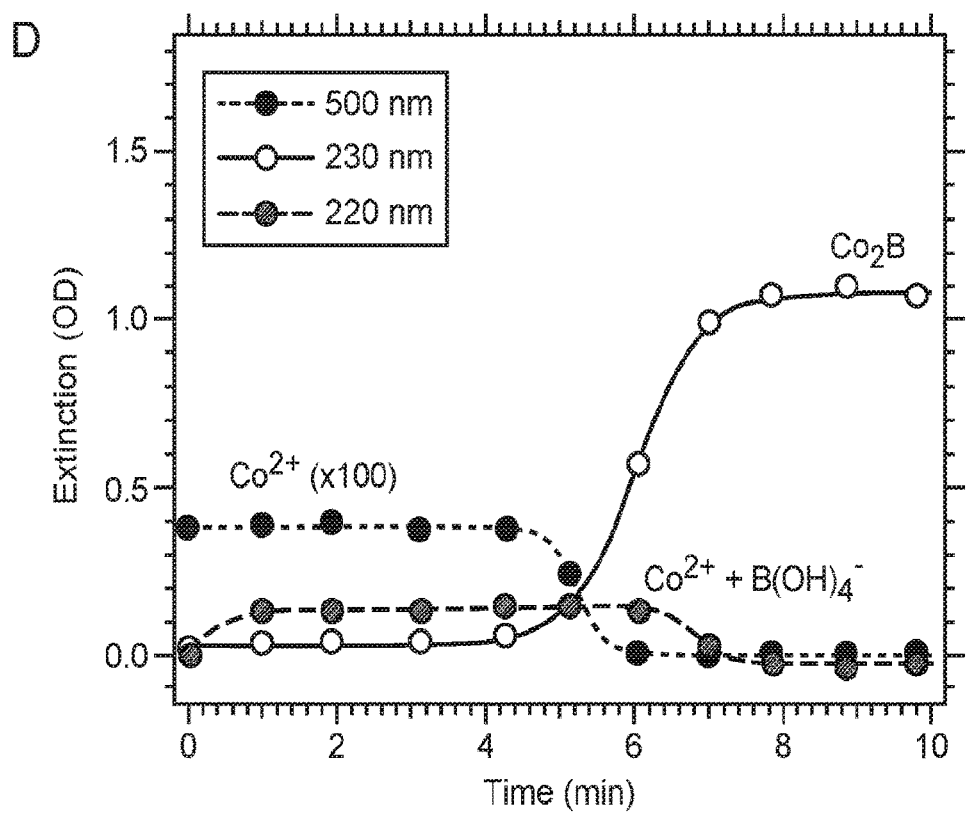

FIG. 13 (Cont.)
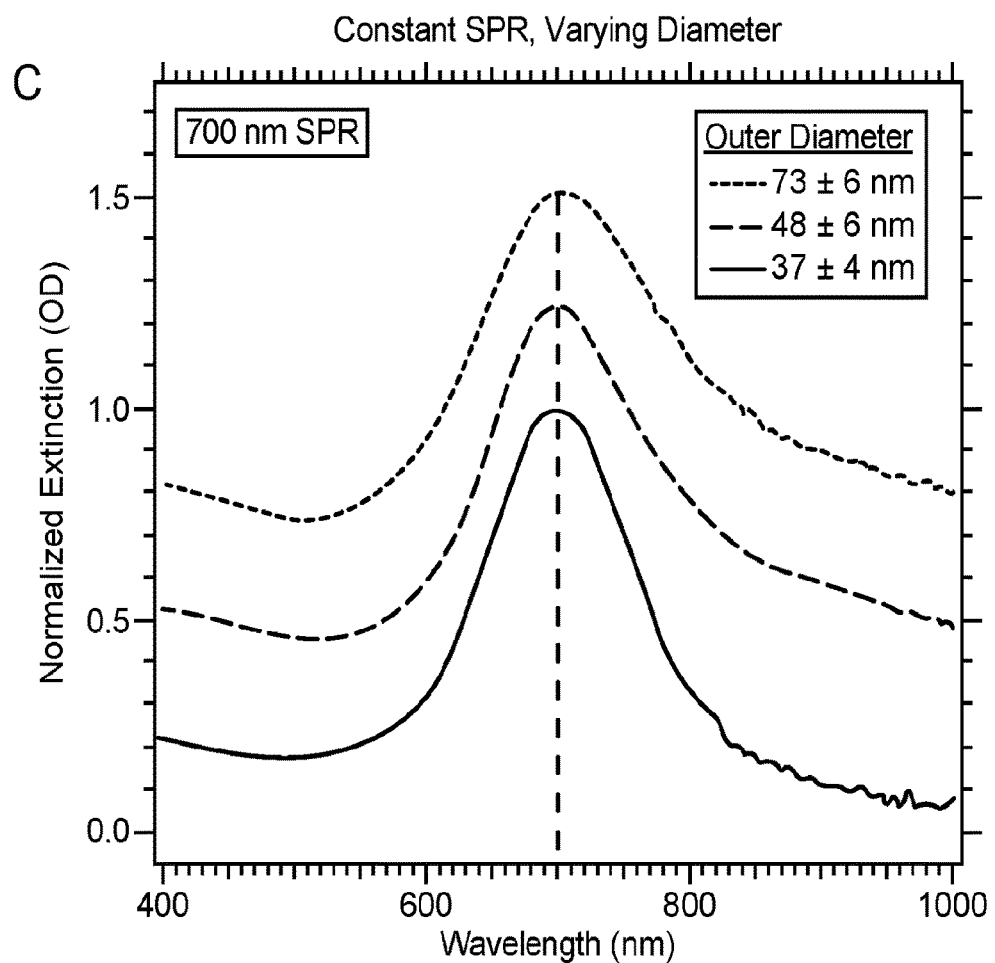
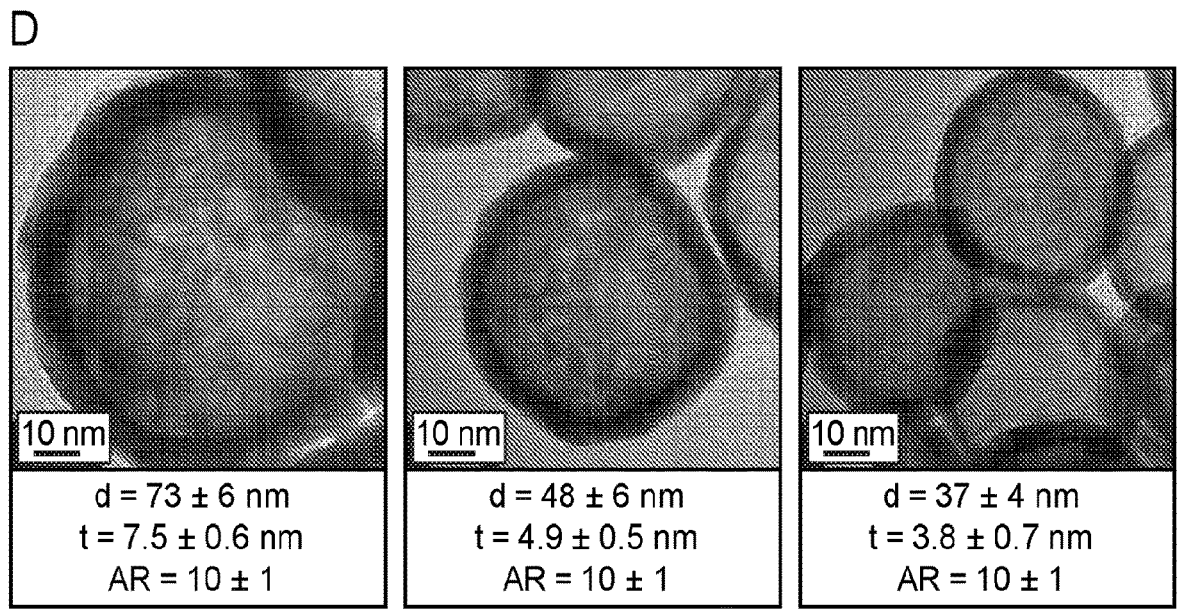

FIG. 14
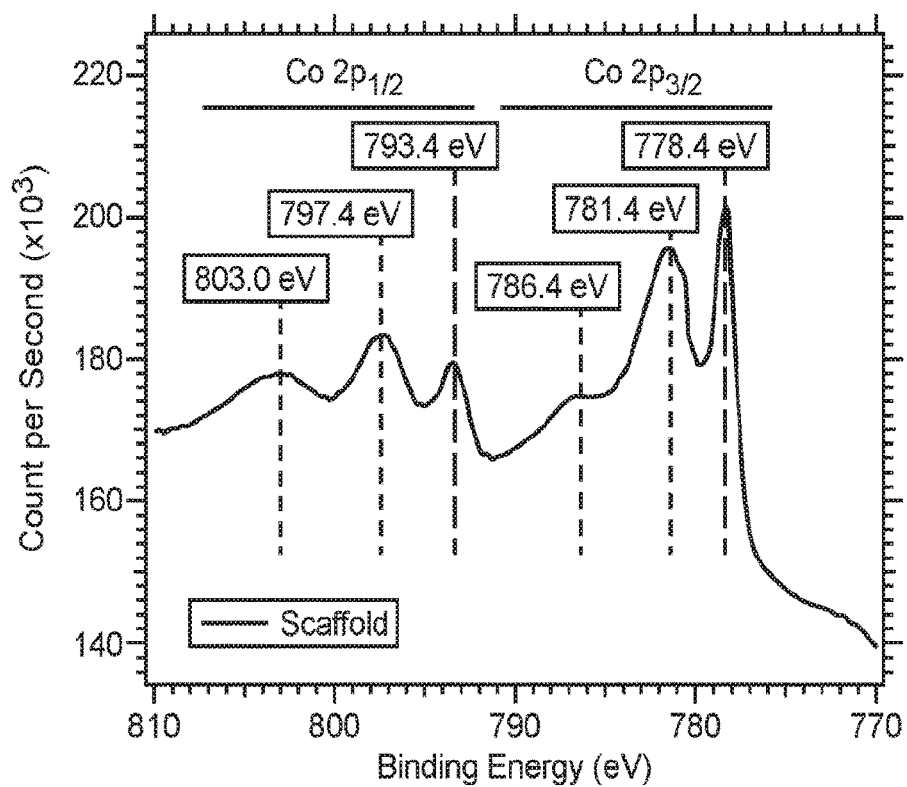
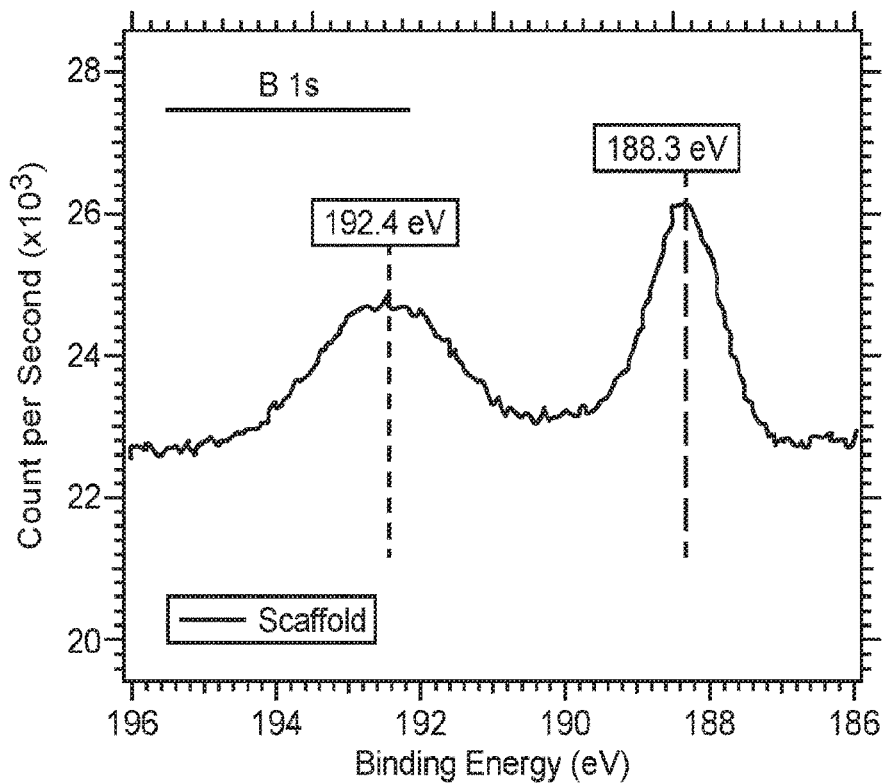

FIG. 15
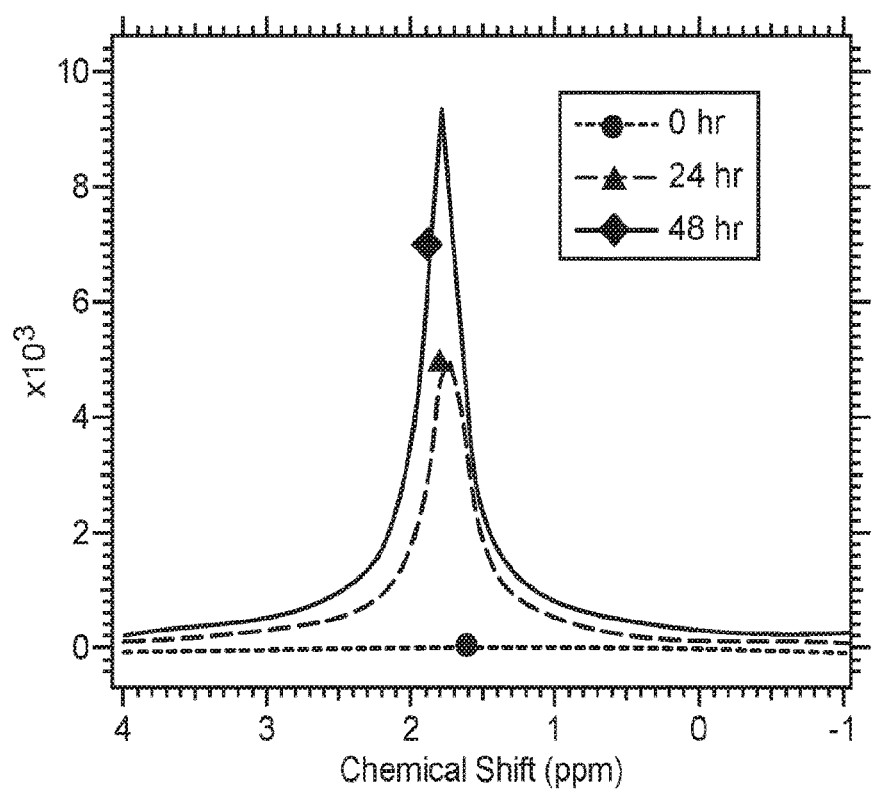
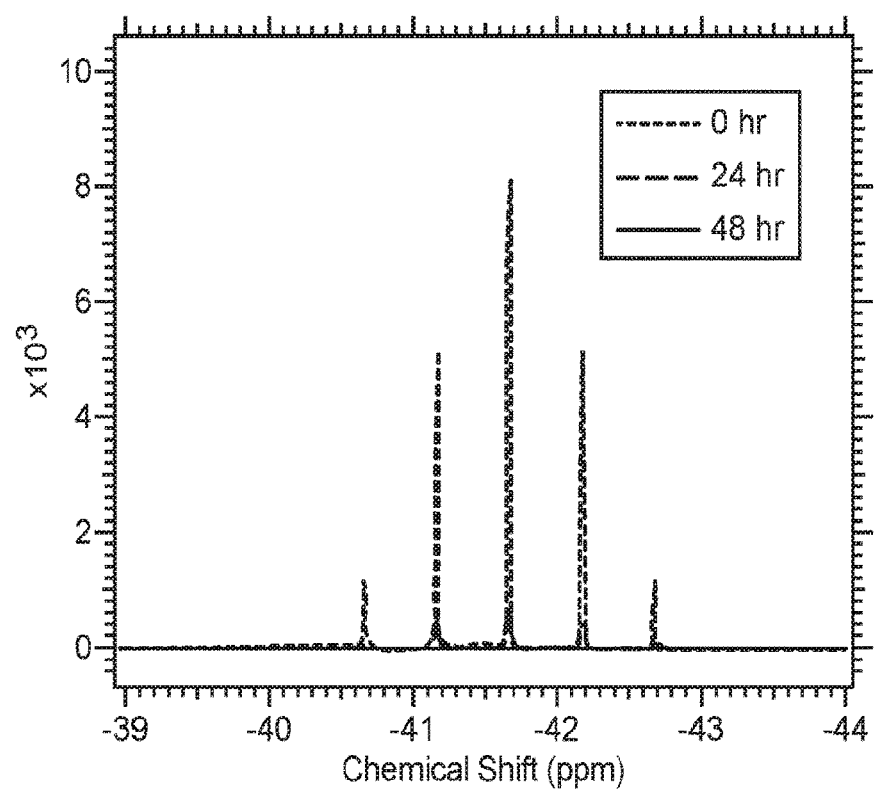

FIG. 15 (Cont.)
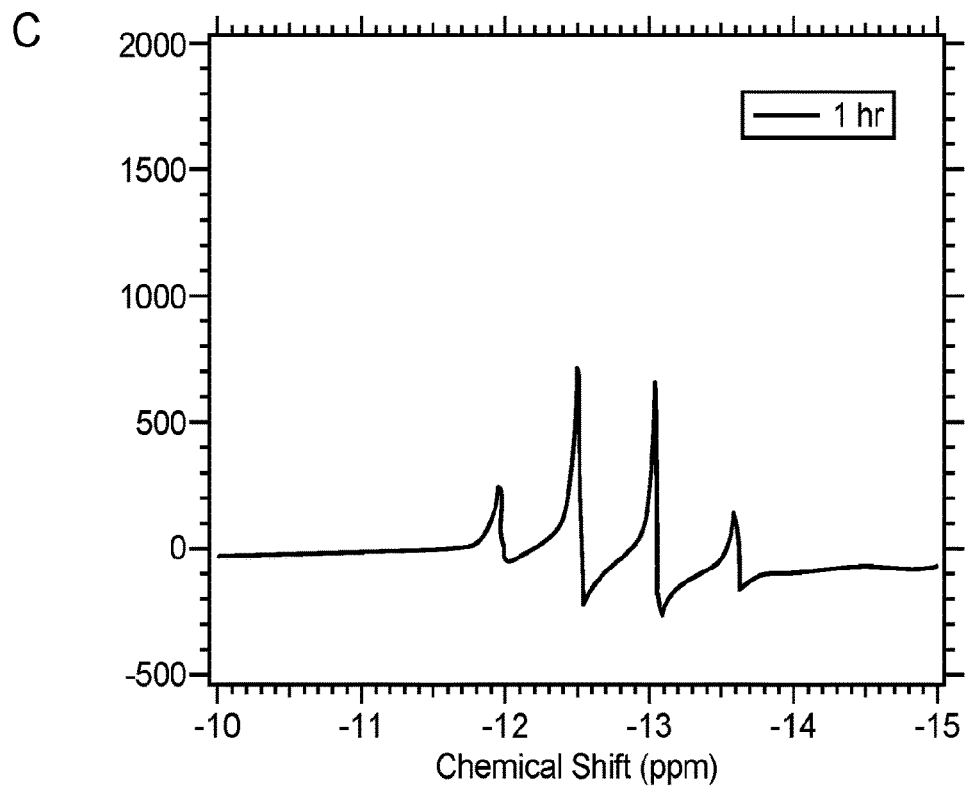
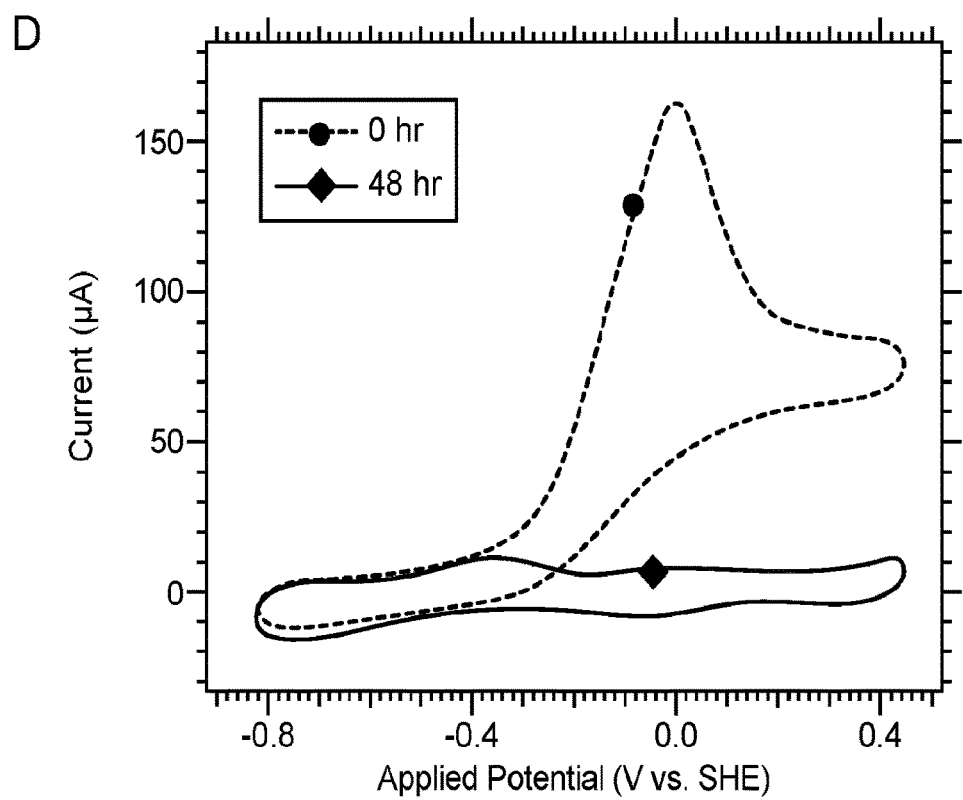

FIG. 16
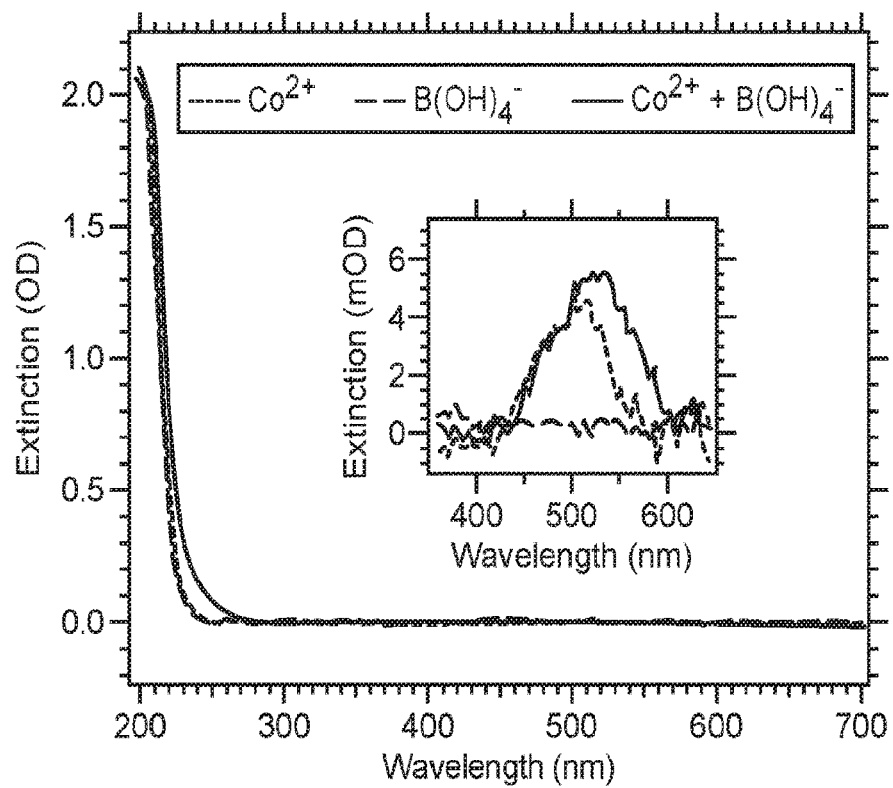
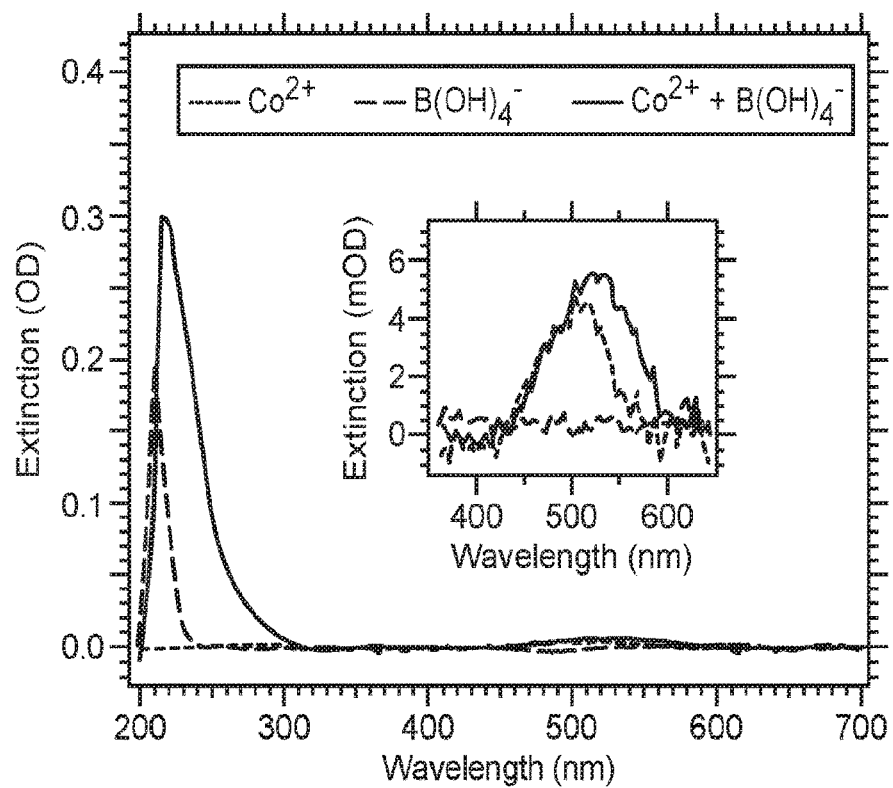

FIG. 17
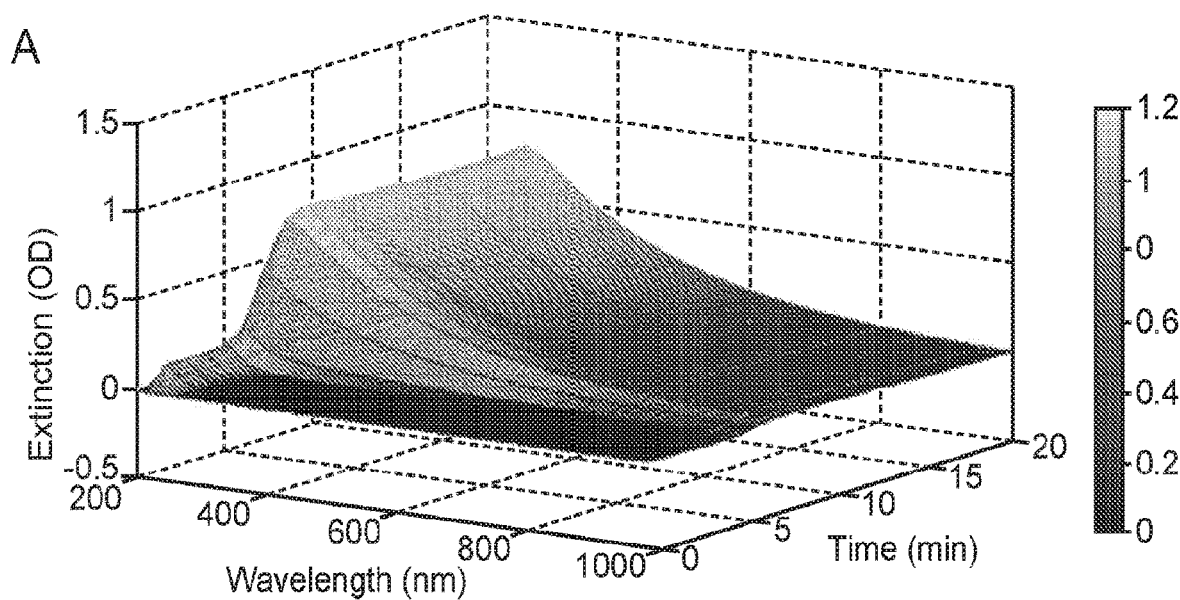
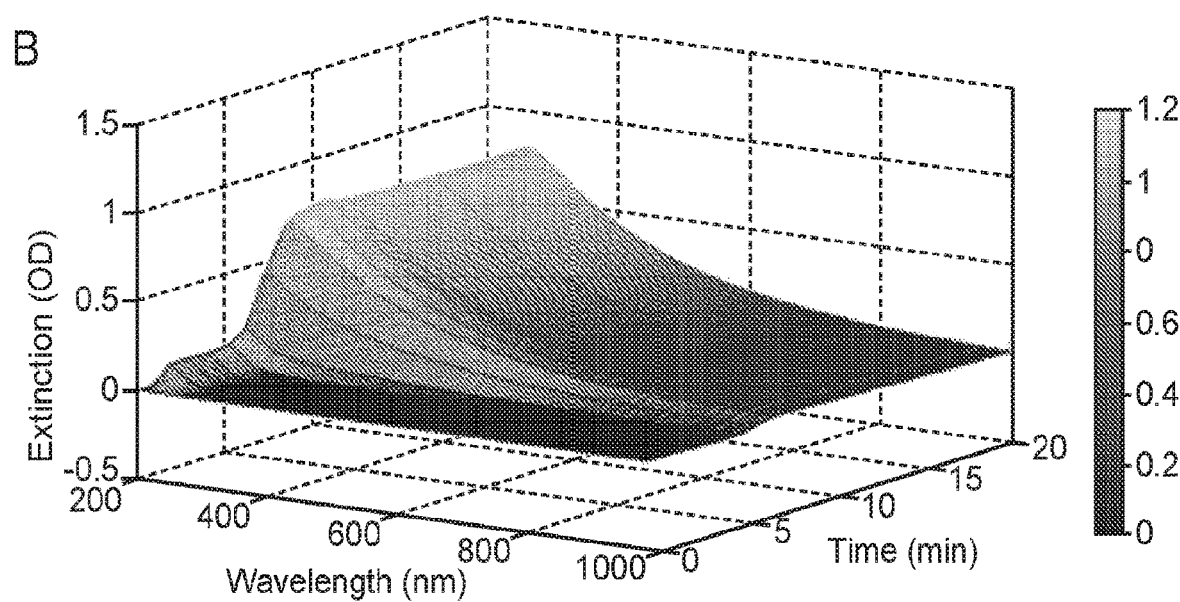

FIG. 17(Cont.)
C
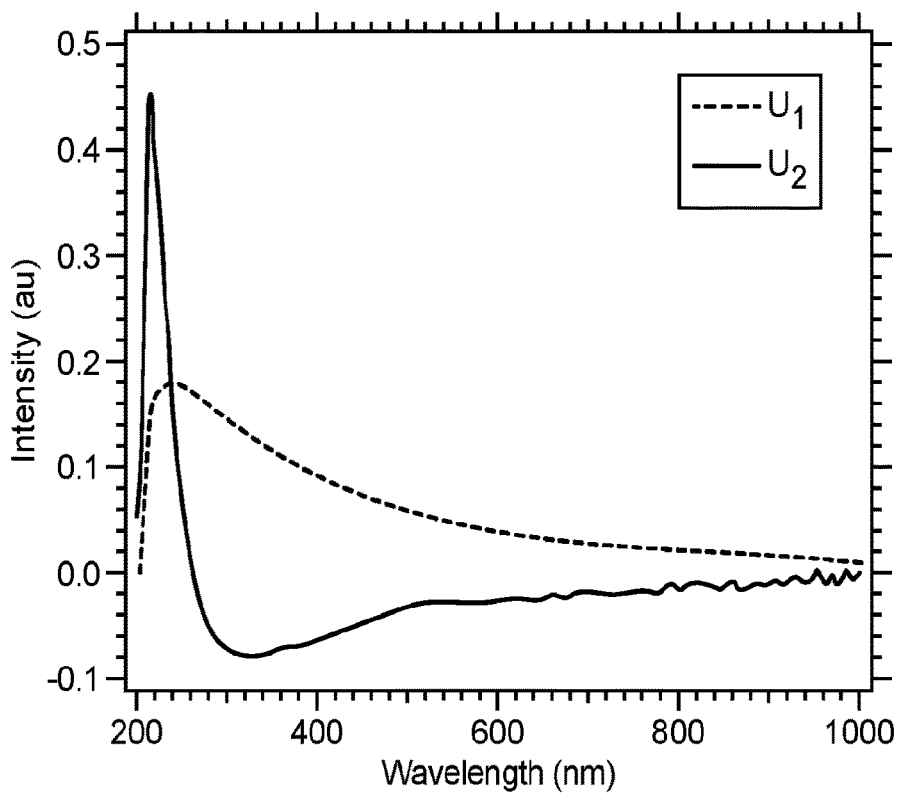
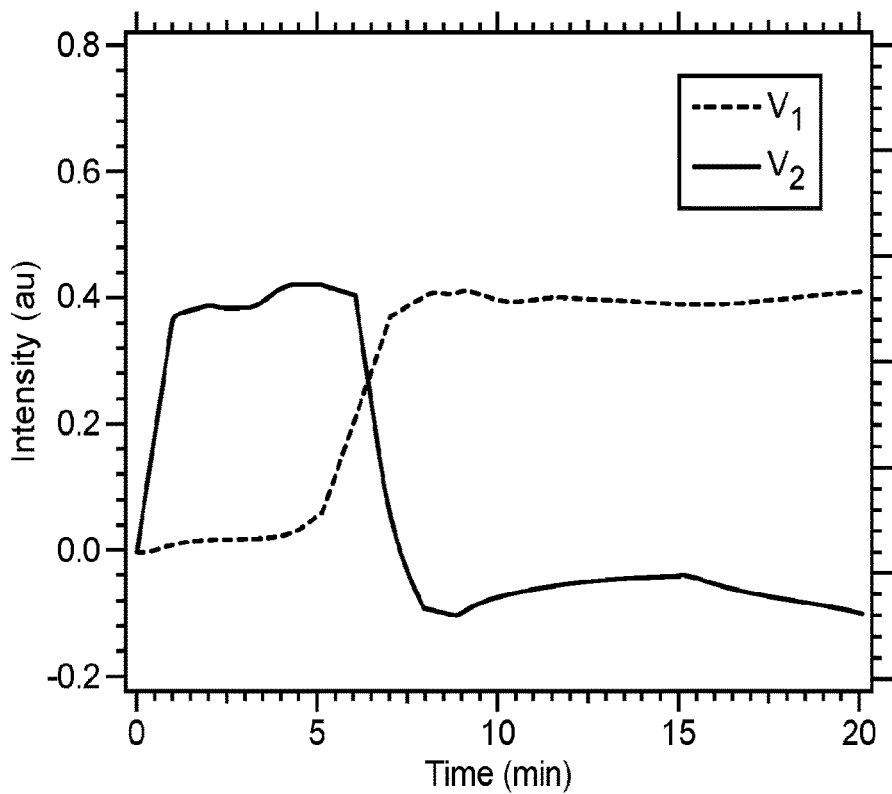

FIG. 18
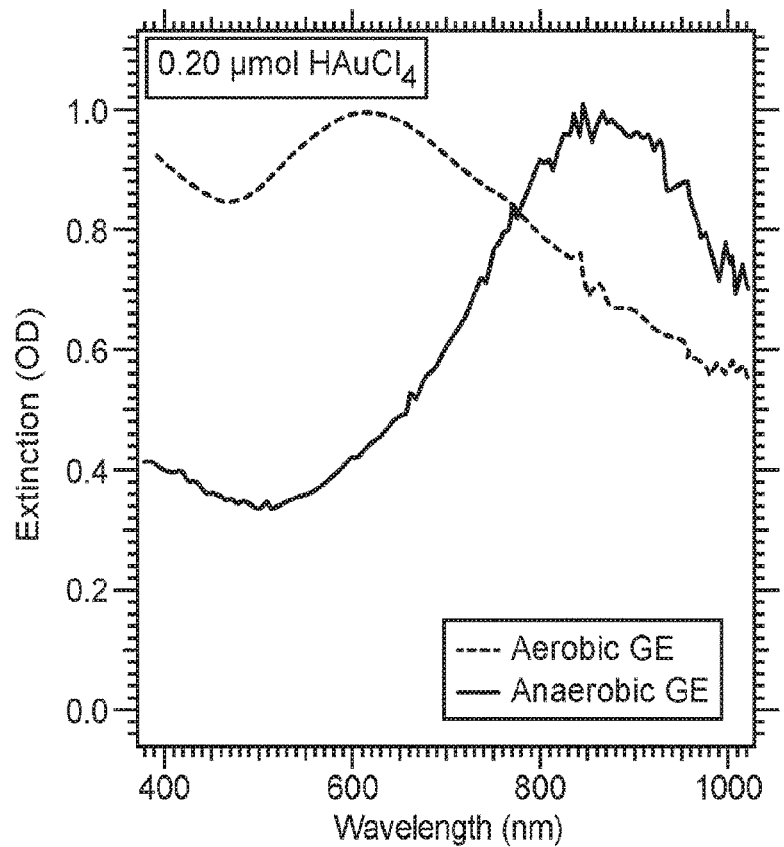
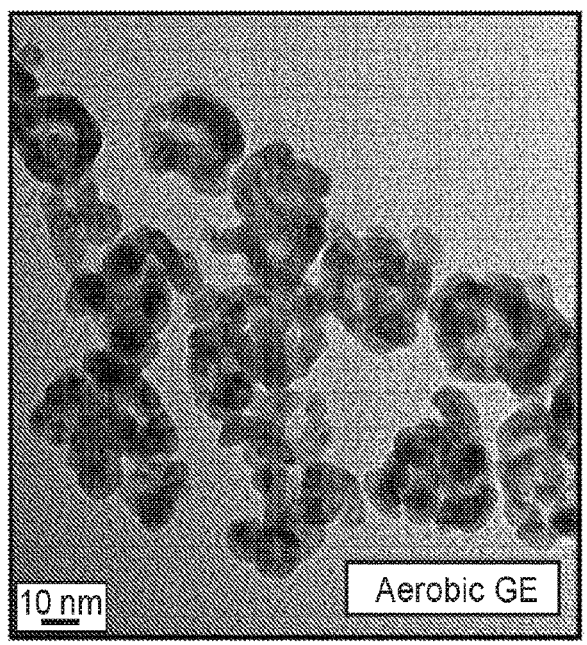
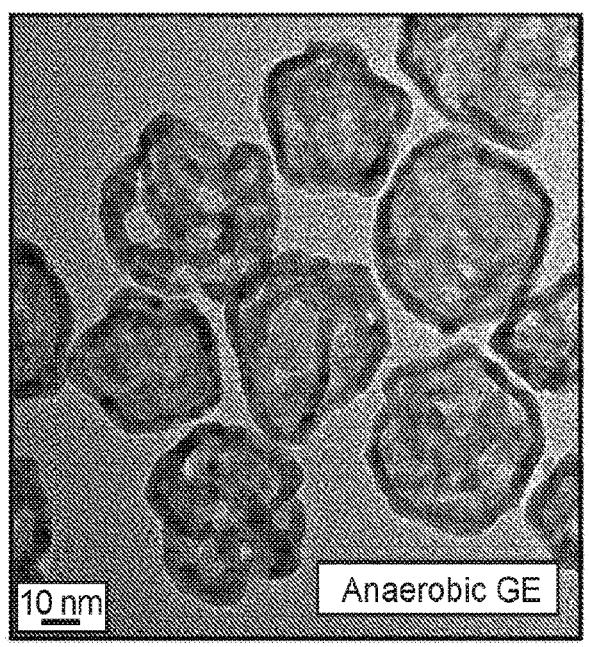

FIG. 18 (Cont.)
B
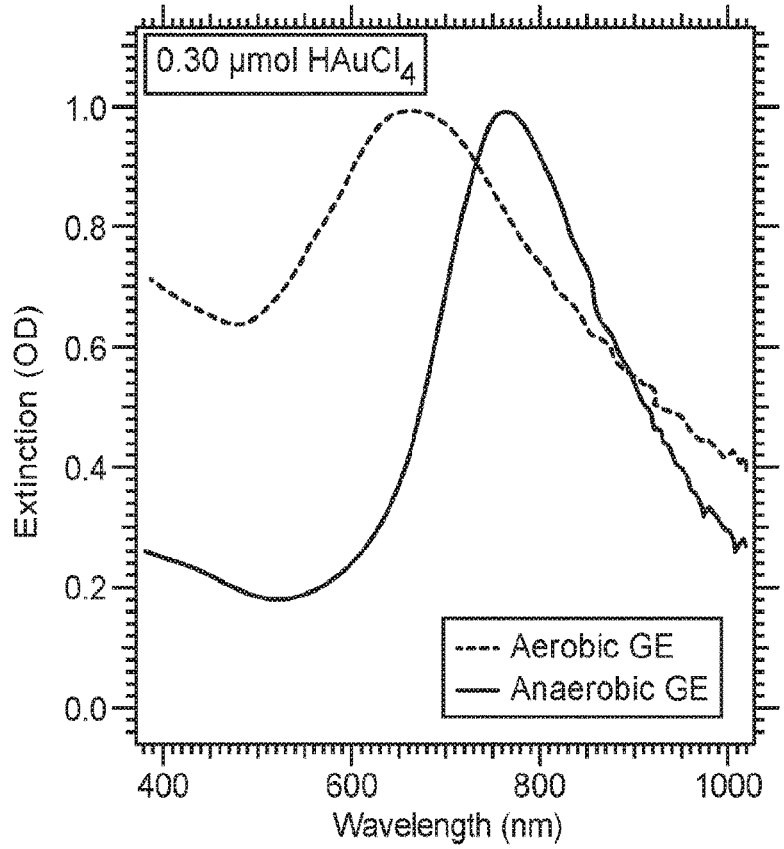
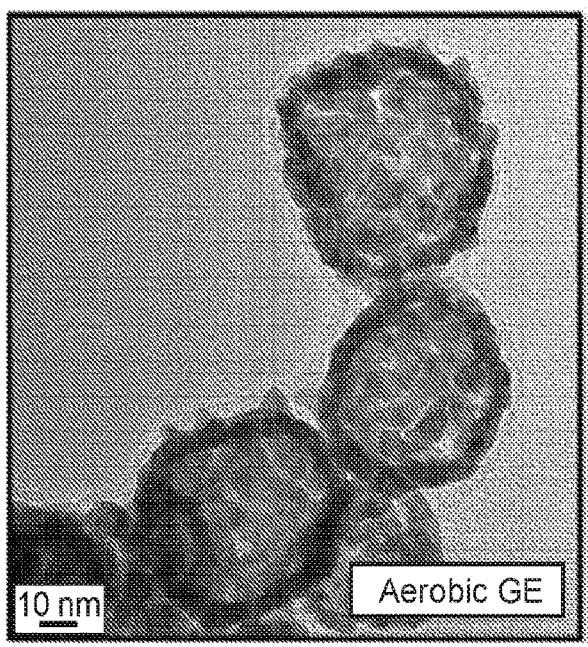
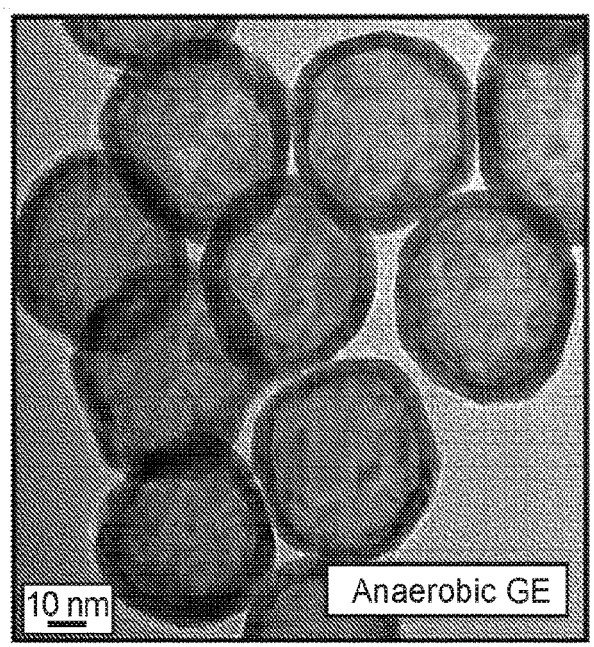

FIG. 18 (Cont.)
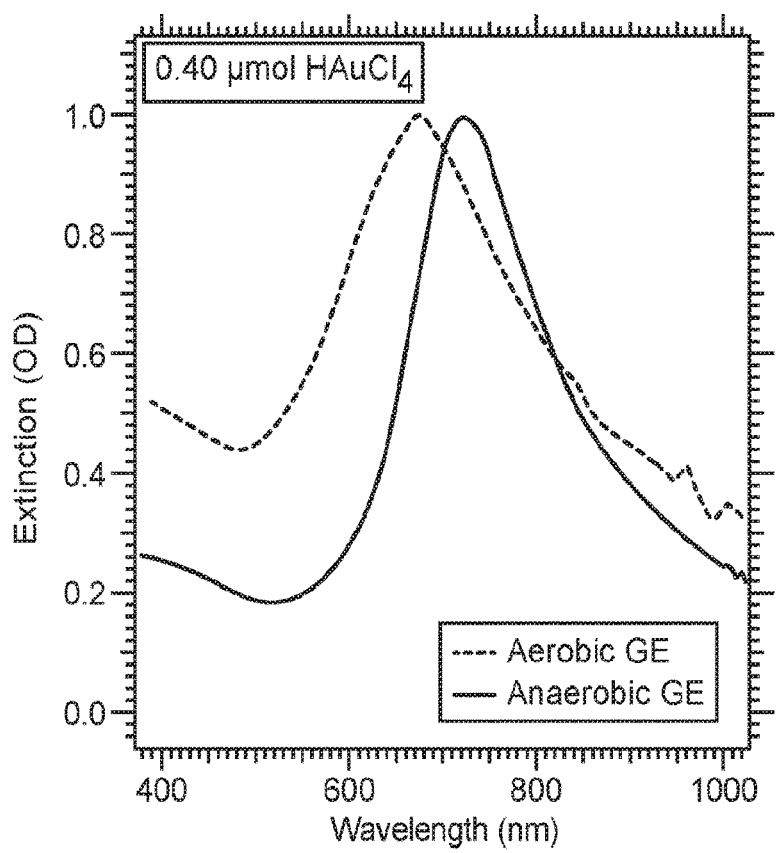
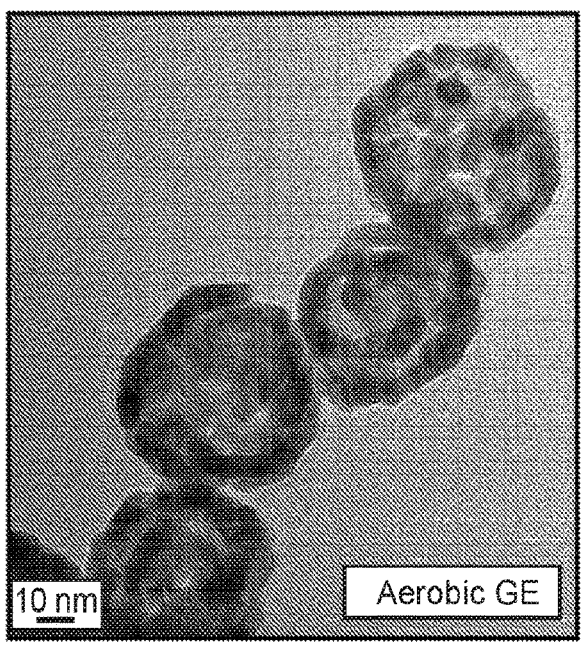
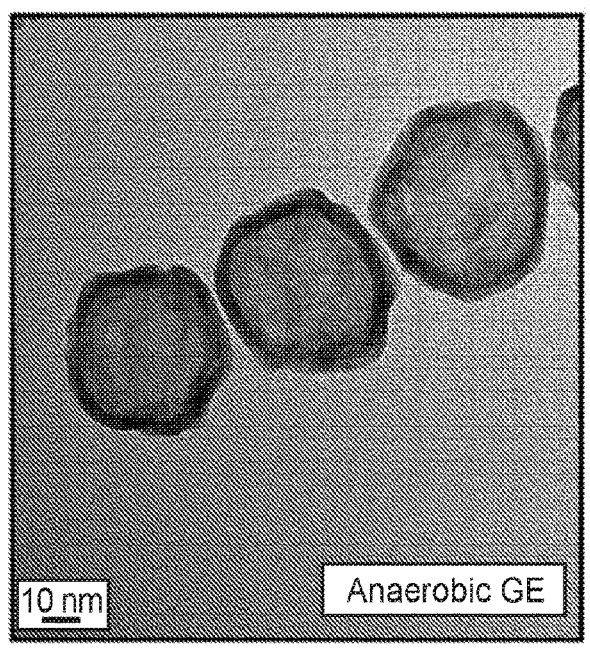

FIG. 18 (Cont.)
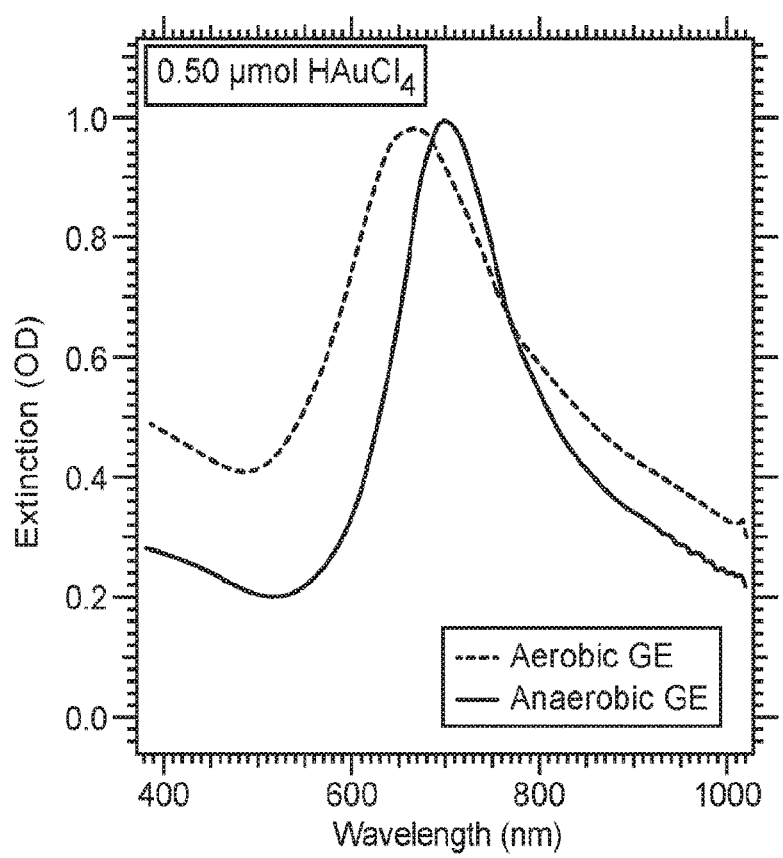
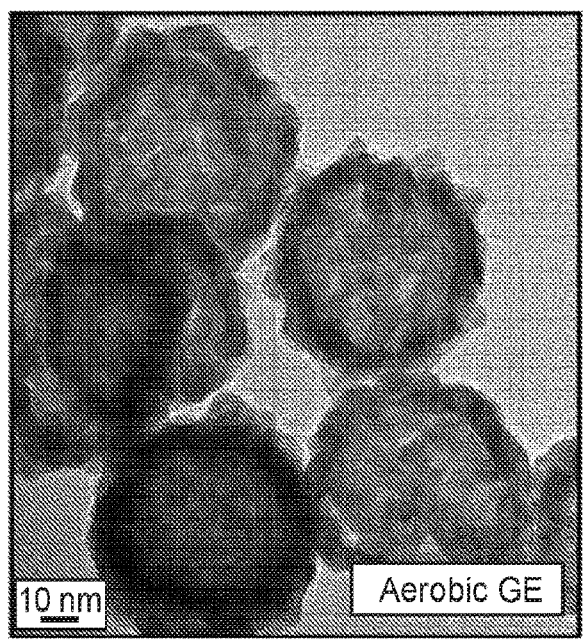
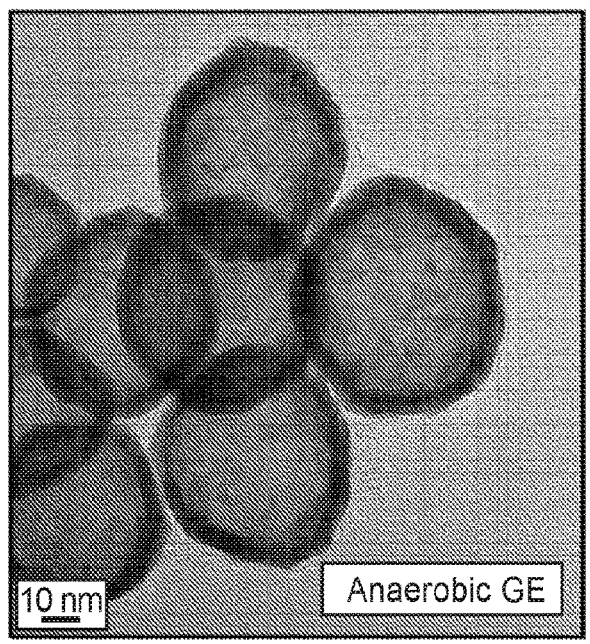

FIG. 18 (Cont.)
E
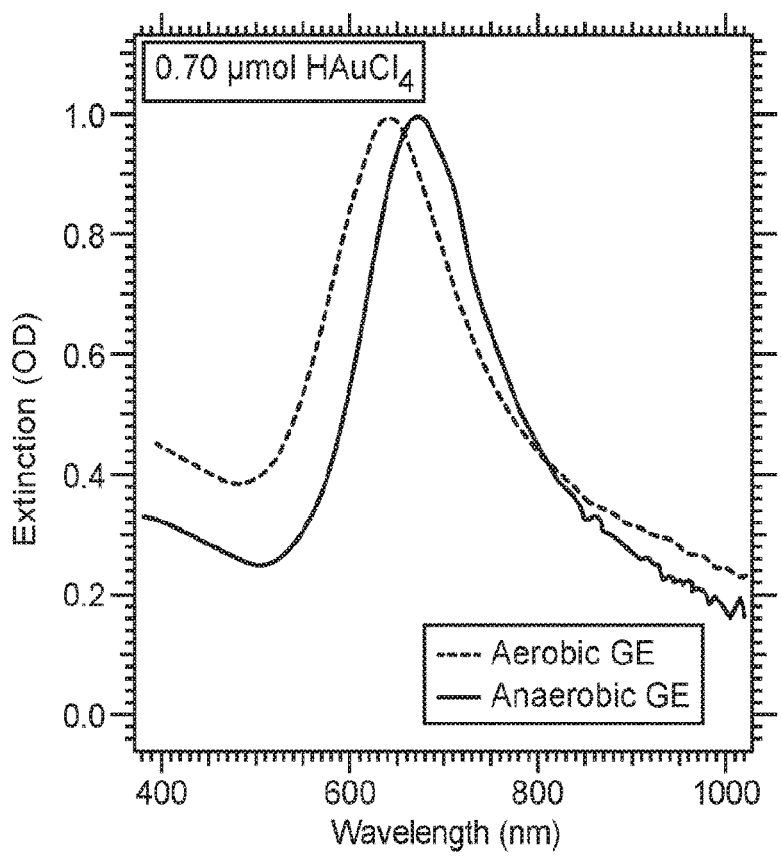
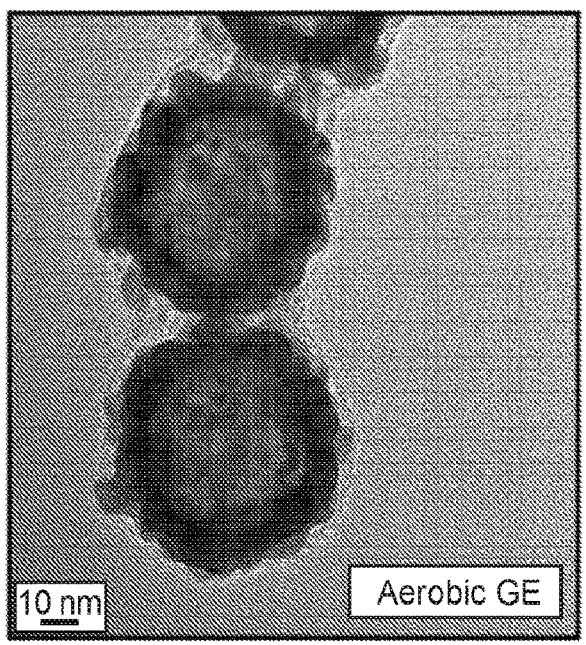
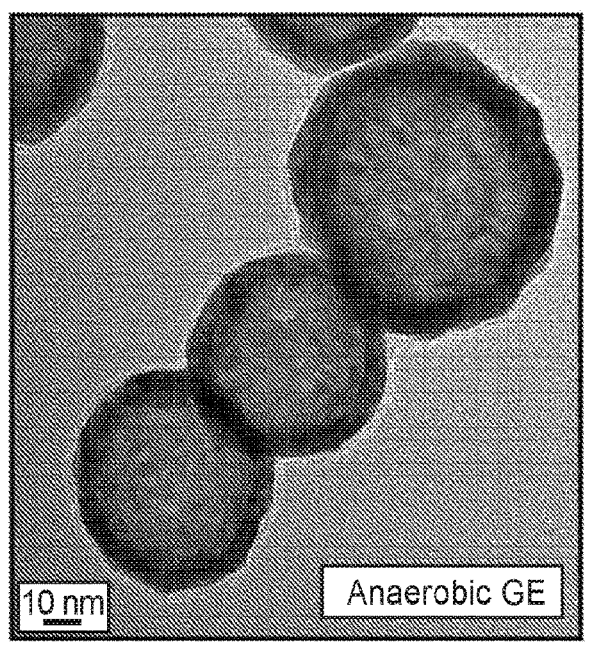

FIG. 18 (Cont.)
F
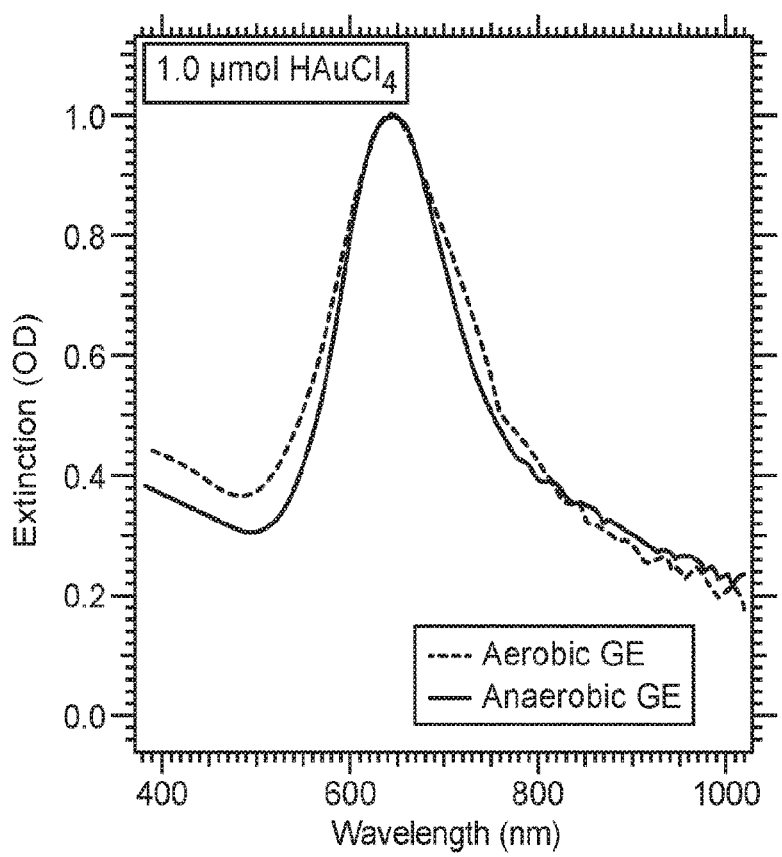
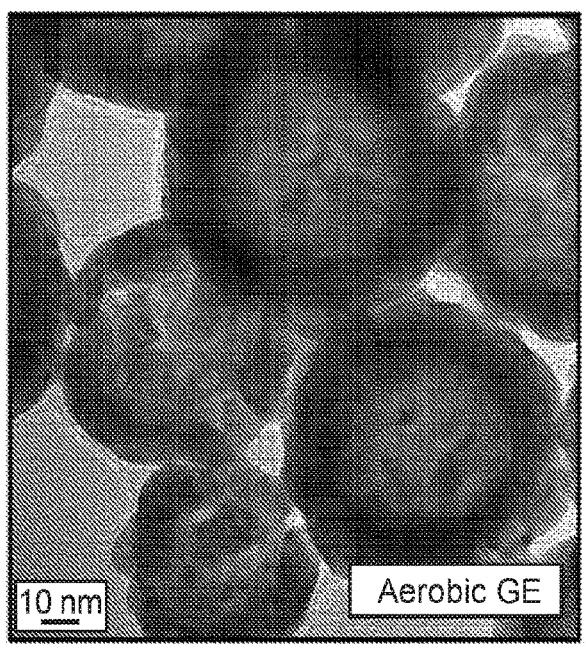
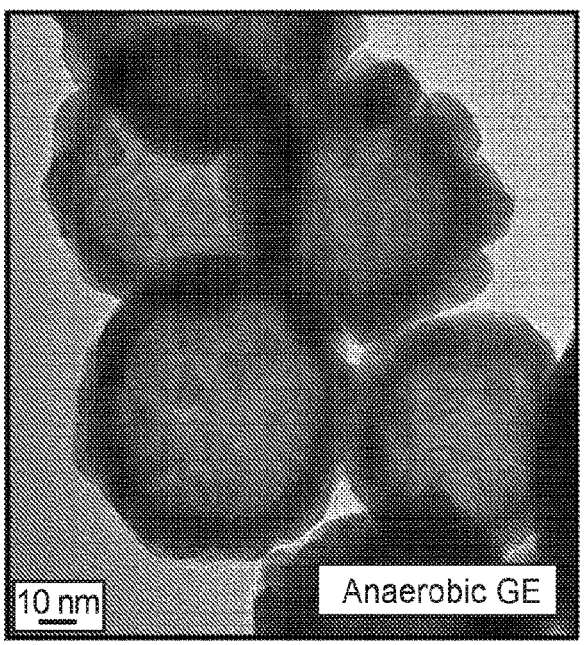

FIG. 20
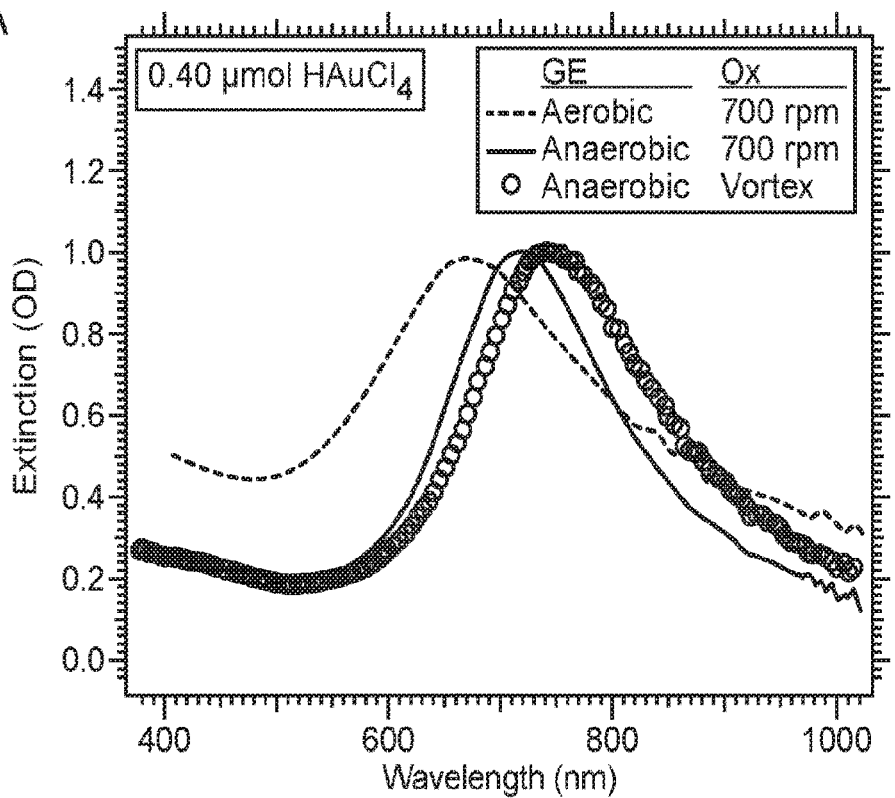
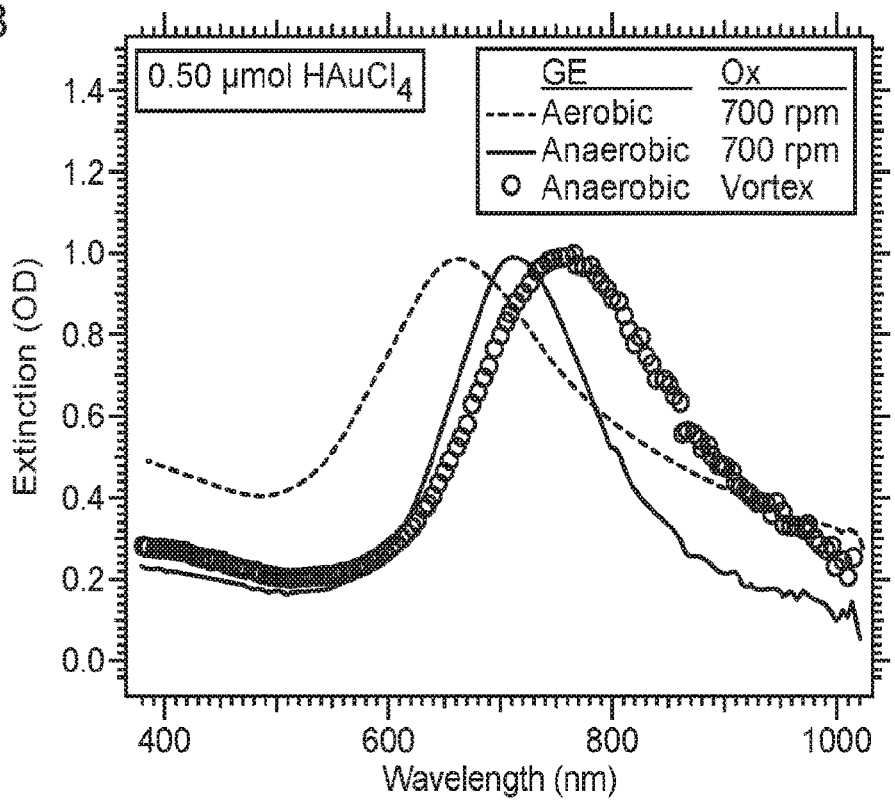

FIG. 20 (Cont.)
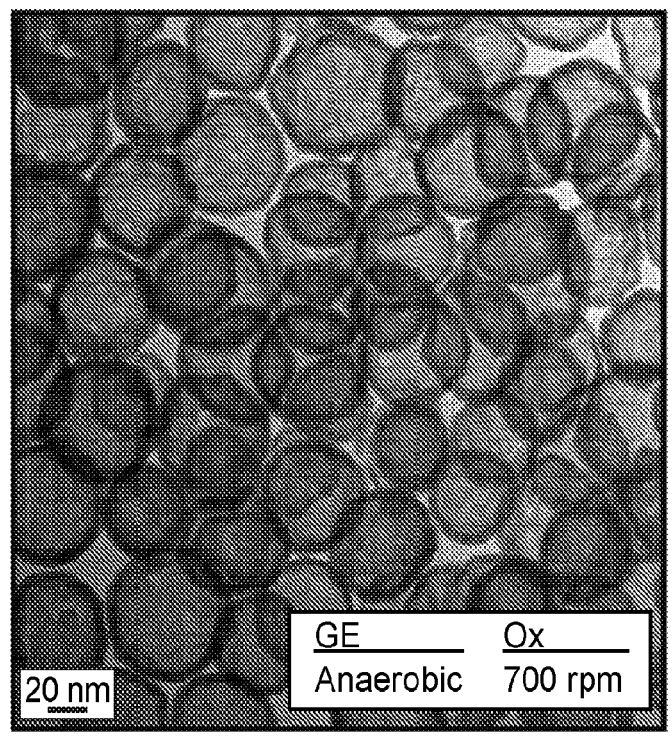
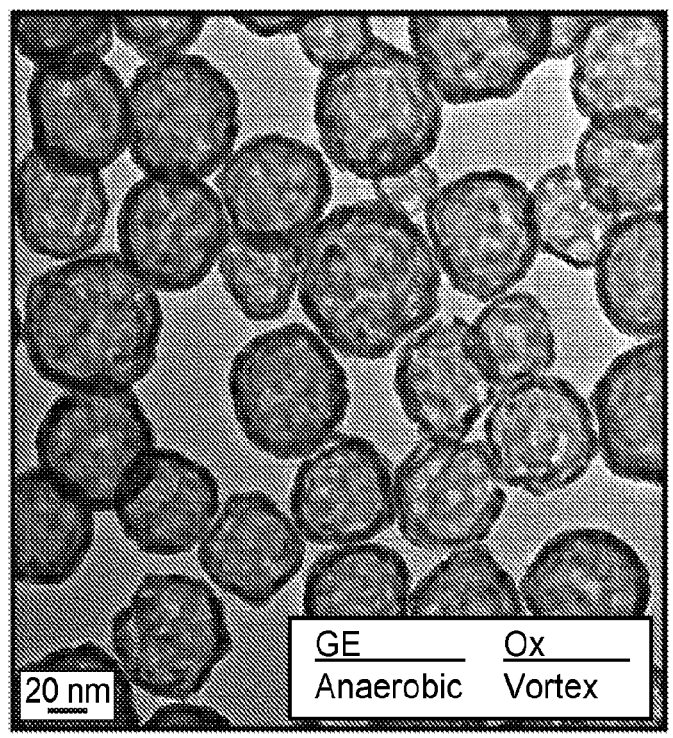

FIG. 23
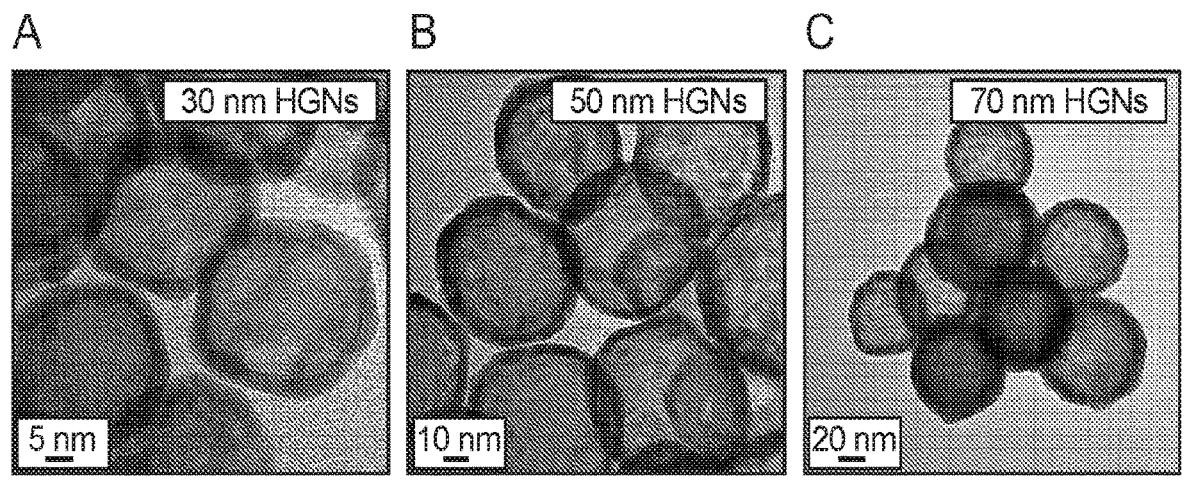
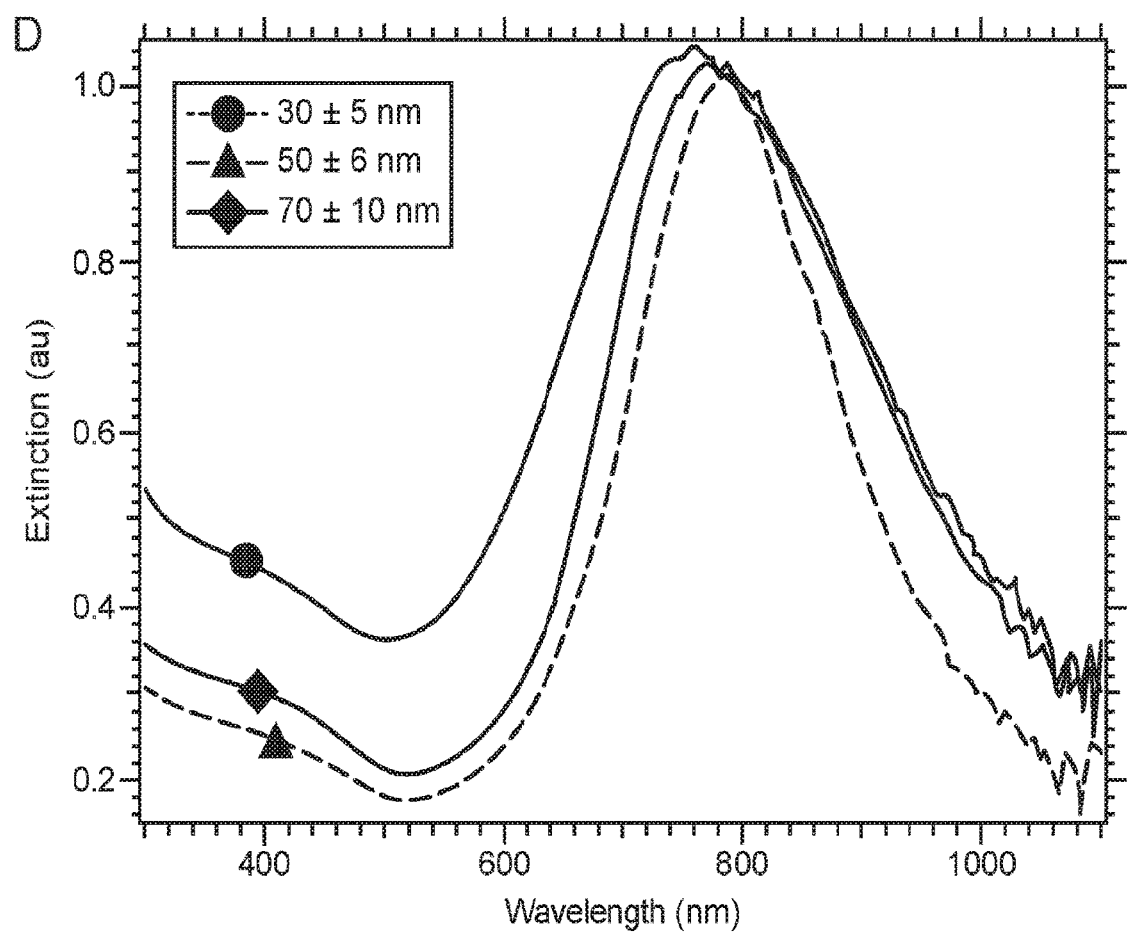

METHODS OF PRODUCING COBALT NANOPARTICLES AND HOLLOW METAL NANOSPHERES

CROSS-REFERENCE TO RELATED APPLICATIONS

This application claims the benefit of U.S. Provisional Patent Application No. 62/636,824, filed Feb. 28, 2018, and U.S. Provisional Patent Application No. 62/471,401, filed Mar. 15, 2017, which applications are incorporated herein by reference in their entireties.

STATEMENT REGARDING FEDERALLY SPONSORED RESEARCH

This invention was made with Government support under contract number NNX15AQ01A awarded by the National Aeronautics and Space Administration. The Government has certain rights in the invention.

INTRODUCTION

Plasmonic metal nanostructures exhibit beneficial optical properties owing to their surface plasmon resonance (SPR), the collective oscillation of conduction band electrons that manifests as strong absorption and/or scattering at the oscillation frequency.[1,2] As oscillation frequency is structure dependent, the SPR may be tuned by changing the size or shape of the nanoparticle.[3-5] This tunability positions plasmonic metal nanoparticles as highly attractive components in nanomedicine,[6-12] optoelectronics,[13-18] and solar energy conversion.[19-23] In these applications, hollow metal nanostructures have distinct advantages over their solid metal counterparts, including lower mass per particle for reduced material costs, higher surface-area-to-volume ratio for increased density of loading or catalytic sites, and enhanced plasmonic performance in applications like SERS, drug delivery, and catalysis.[24-28] Furthermore, the SPR of hollow structures are more tunable as the hollow core provides an additional parameter to modify the overall electronic structure. For one structure of note, the hollow gold nanosphere (HGN), the SPR may be tuned across the visible wavelengths and into the near-infrared by adjusting the ratio of outer diameter to shell thickness (the aspect ratio).[29] Increasing the aspect ratio, effectively red-shifting the SPR, may be accomplished by either increasing the diameter or thinning the shell. Because of this twofold tunability, the diameter and SPR frequency can in principle be independently adjusted, allowing for the formation of targeted photoactivated structures of specific size and optical functionality. As such, HGNs could therefore become a powerful platform for a variety of nano-enabled applications.

Since the introduction of HGNs in 2005, much work has been done to elucidate their structure-dependent optical properties,[29-32] gain reproducibility of synthesis,[33,34] and demonstrate their use in a variety of applications.[35-38] However, their formation mechanism has not yet been controlled to the point of achieving independent selection of both size and SPR. To this end, the synthesis must be investigated and improved to enable a high degree of control over diameter and shell thickness.

HGN diameters are determined by those of their cobalt-based nanoparticle scaffolds, sacrificial templates onto which shells of gold are formed through galvanic exchange.[29,39] These scaffolds are commonly made through sodium borohydride nucleation of aqueous cobalt salt. Although this reaction is often studied, it is not yet well understood. Disagreement exists in the literature over the identity of the main product (e.g., various cobalt-boron alloys have been reported) and size control methods remain elusive. In 2006, Schwartzberg et al. reported that small adjustments in overall scaffold diameter may be made by changes to the volume of both the sodium borohydride reducing agent and sodium citrate capping ligand used in scaffold synthesis, but larger sizes proved difficult to achieve reproducibly.[29] In 2009, a combination of alcohol solvents and triblock copolymer surfactant were used to synthesize Co nanoparticles from 3.2 to 171.4 nm, but the larger size regime was plagued by broad size dispersion and precipitation, and analysis of the mid-range size regime reveals large relative standard deviations.[40] In 2011, silica-coated Co—B nanoparticles were synthesized from 50 to 250 nm in diameter with improved relative standard deviation (15-19%) by adjusting the ratio of surfactant to cobalt salt precursor, but silica coating was required for particle stability and small size regimes were not demonstrated.[41] Recently, Pu et al. showed that reaction temperature may be used to slow nucleation and promote growth from 24 to 122 nm in diameter, but resultant particles were polydisperse and exact sizes difficult to control.[42] Although progress has been made, size control methods for cobalt-based nanoparticle systems remain limited and fine adjustments over a large size range have not been realized experimentally.

While the HGN diameter is determined by that of its scaffold, the SPR frequency and full width at half maximum (FWHM) are determined by shell thickness and uniformity, structural parameters that are governed by the galvanic exchange process. Previously, Schwartzberg et al. showed that shell thickness could be increased simply by providing more gold during galvanic exchange,[29] but other factors affecting shell structure and uniformity have not been explored. One such factor is environmental oxygen. Galvanic exchange in HGN synthesis has traditionally been performed in aerobic conditions[29-34,38-39] with cobalt as a starting template because of its favorable reduction potential and ease of oxidation in air.[43-46] This ease of oxidation allows facile removal of residual core material after shell formation without relying on post processing techniques like wet chemical etching.

SUMMARY

Provided are methods of producing cobalt-based nanoparticles ($Co_xB_y$ NPs) of a pre-selected diameter. The methods include nucleating $Co^{2+}$ ions with a sodium borohydride ($NaBH_4$) solution having a selected ratio of tetrahydroxyborate ($B(OH)_4^-$) to tetrahydroborate ($BH_4^-$) based on the pre-selected diameter, where the ratio of $B(OH)_4^-$ to $BH_4^-$ is positively correlated with the pre-selected diameter. Also provided are methods of using the $Co_xB_y$ NPs to produce hollow metal nanospheres (HMNs). Methods of producing $Co_xB_y$ NP core/metal shell structures are also provided, such methods including combining in an anaerobic galvanic exchange reaction a deaerated solution including $Co_xB_y$ NP scaffolds and a deaerated solution including a metal. Also provided are methods of producing HMNs from the $Co_xB_y$ NP core/metal shell structures. Compositions and kits that find use in practicing the methods of the present disclosure and using HMNs produced in accordance with the methods of the present disclosure, are also provided.

BRIEF DESCRIPTION OF THE FIGURES

Some of the figures are better understood when provided in color. Applicant submits that the color versions of the figures are part of the original disclosure and reserves the right to provide color versions of the figures in later proceedings.

FIG. 1 Panel A: XPS of the $Co_xB_y$ NP scaffold as compared to cobalt ions from common cobalt compounds. Panel B: XPS of the $Co_xB_y$ NP scaffold as compared to a linear combination of ~70% cobalt boride compound and ~30% unreacted $CoCl_2$ precursor.

FIG. 4 Dynamic light scattering (DLS) of $Co_xB_y$ NP scaffolds made with 250 μl of total $BH_4^-$ comprising varying ratios of fresh:aged $BH_4^-$. Aged $BH_4^-$ is 1M $NaBH_4$ that was aged in water for 24 hours.

FIG. 5 DLS examples showing fine control of $Co_xB_y$ NP diameter (measured as hydrodynamic diameter) while maintaining monodispersity. Fine control is possible by adjusting both the amount of borohydride in the synthesis as well as the ratio of fresh:aged $BH_4^-$.

FIG. 6 Scanning electron microscope (SEM) images of 30 nm, 45 nm, and 60 nm HGNs with 800 nm SPR.

FIG. 8 Panel A: Extinction spectra for $Co_xB_y$ NPs made with $BH_4^-$:$Co^{2+}$ molar ratios ranging from 0 to 5.00 (Scaffolds 1-5). With no reducing agent, Scaffold 1 represents only aqueous citrate and $CoCl_2$. As such, an extinction feature for hydrated $Co^{2+}$ ions can be seen at 500 nm, as highlighted in the inset. Panel B: $Co_xB_y$ NP extinction for scaffolds made with $B(OH)_4^-$:$BH_4^-$ ratios of 0.500 and 1.00 (Scaffolds 6-9). Associated synthetic parameters are reported in Table 1.

FIG. 9 Panel A: Time-resolved extinction spectra for the formation of Scaffold 5: 23±3 nm $Co_xB_y$ NPs over the course of 20 min. Panel B: Two wavelengths of interest are monitored for the first 10 min: 500 nm to highlight disappearance of hydrated $Co^{2+}$ ions and 230 nm to highlight formation of $Co_xB_y$ NPs. Panel C: Time-resolved extinction spectra for the formation of Scaffold 7: 56±1 nm $Co_xB_y$ NPs over the course of 20 min. Panel D: Three wavelengths of interest are monitored for the first 10 min: 500 nm to highlight disappearance of hydrated $Co^{2+}$ ions, 230 nm to highlight formation of $Co_xB_y$ NPs, and 220 nm to highlight interaction of $Co^{2+}$ with $B(OH)_4^-$ in the presence of citrate. The 220 and 230 nm spectral contributions were deconvolved using singular value decomposition. For all spectra, the citrate contribution has been subtracted to better reveal the appearance of extinction below 300 nm.

FIG. 15 Low-field $^{11}B$ NMR (Panel A) and high-field proton-coupled $^{11}B$ NMR (Panel B) spectra of aqueous $NaBH_4$ after hydrolyzing for 0 hr, 24 hr, and 48 hr. Panel C: Proton-coupled $^{11}B$ NMR of aqueous $NaBH_4$ after hydrolyzing for 1 hr showing an intermediate quartet attributed to $BH_3OH^-$. Panel D: Cyclic voltammogram of aqueous $NaBH_4$ after hydrolyzing for 0 hr and 48 hr, 2500 mV/s sweep rate.

FIG. 18 Optical and structural effects of environmental oxygen during galvanic exchange (GE). Extinction spectra are displayed for HGNs made via galvanic exchange between $Co_xB_y$ Scaffold 7 (56±1 nm) and 0.20 (Panel A), 0.30 (Panel B), 0.40 (Panel C), 0.50 (Panel D), 0.70 (Panel E), and 1.0 (Panel F) μmol $HAuCl_4$. Results for aerobic (dashed line) and anaerobic (solid line) GE protocols are shown, as well as corresponding HRTEM images, scale bars 10 nm.

FIG. 20 Optical and structural effects of rate of oxygenation after GE. Extinction spectrum for HGNs made from Scaffold 7 and 0.40 (Panel A) and 0.50 (Panel B) μmol $HAuCl_4$ with anaerobic GE with subsequent vortex oxidation (open circles) and anaerobic GE with subsequent stirring at 700 rpm (solid line). Aerobic GE with subsequent stirring at 700 rpm (dashed line) is also provided for comparison. Panels C and D: Corresponding HRTEM images for 0.40 μmol $HAuCl_4$ results in Panel A, scale bar 10 nm.

FIG. 23 Structural and optical characterization of HGNs. HRTEM images of (a) 30±5, (b) 50±6, and (c) 70±10 nm HGN and (d) extinction spectra confirming ~795 nm SPR for each size.

DETAILED DESCRIPTION

Figure 2:
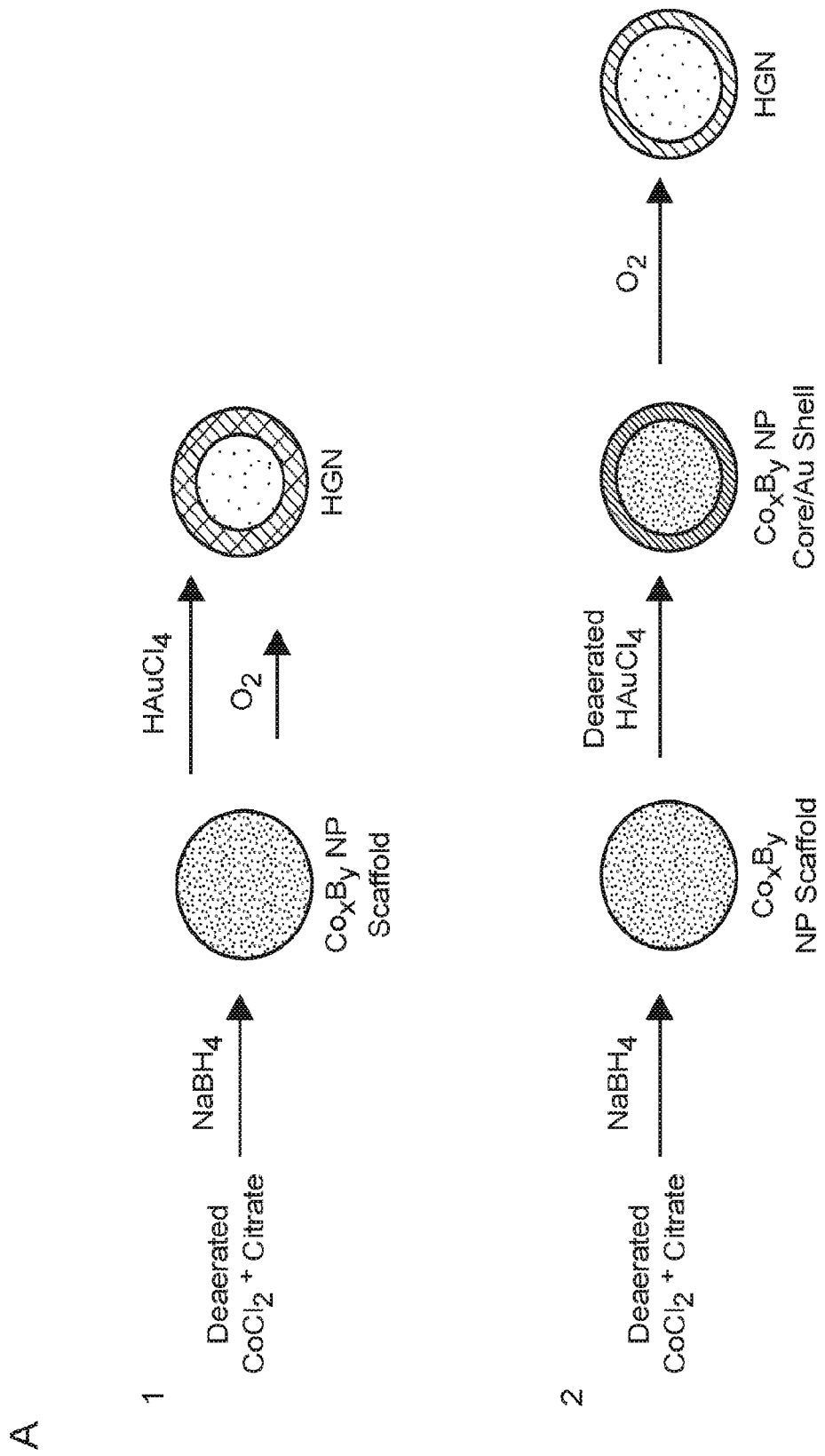
FIG. 2 Panel A: Comparison of previous approach (1) with an example HGN synthesis of the present disclosure (2) in regard to introduction of oxygen. In process 2, the galvanic exchange is allowed to occur in the absence of oxygen. Panel B: UV-Vis of resultant HGNs from processes 1 and 2, showing a large red-shift in SPR when the gold is deaerated and the two solutions are introduced in the absence of oxygen. SEM images are also shown for each process to depict the underlying physical difference in the gold shells.

Provided are methods of producing cobalt-based nanoparticles ($Co_xB_y$ NPs) of a pre-selected diameter. The methods include nucleating $Co^{2+}$ ions with a sodium borohydride ($NaBH_4$) solution having a selected ratio of tetrahydroxyborate ($B(OH)_4^-$) to tetrahydroborate ($BH_4^-$) based on the pre-selected diameter, where the ratio of $B(OH)_4^-$ to $BH_4^-$ is positively correlated with the pre-selected diameter. Also provided are methods of using the $Co_xB_y$ NPs to produce hollow metal nanospheres (HMNs). Methods of producing $Co_xB_y$ NP core/metal shell structures are also provided, such methods including combining in an anaerobic galvanic exchange reaction a deaerated solution including $Co_xB_y$ NP scaffolds and a deaerated solution including a metal. Also provided are methods of producing HMNs from the $Co_xB_y$ NP core/metal shell structures. Compositions and kits that find use in practicing the methods of the present disclosure and using HMNs produced in accordance with the methods of the present disclosure, are also provided.

Before the methods, compositions and kits of the present disclosure are described in greater detail, it is to be understood that the methods, compositions and kits are not limited to particular embodiments described, as such may, of course, vary. It is also to be understood that the terminology used herein is for the purpose of describing particular embodiments only, and is not intended to be limiting, since the scope of the methods, compositions and kits will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the methods, compositions and kits. The upper and lower limits of these smaller ranges may independently be included in the smaller ranges and are also encompassed within the methods, compositions and kits, subject to any specifically excluded limit in the stated range. Where the stated range includes one or both of the limits, ranges excluding either or both of those included limits are also included in the methods, compositions and kits.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which the methods, compositions and kits belong. Although any methods, compositions and kits similar or equivalent to those described herein can also be used in the practice or testing of the methods, compositions and kits, representative illustrative methods, compositions and kits are now described.

All publications and patents cited in this specification are herein incorporated by reference as if each individual publication or patent were specifically and individually indicated to be incorporated by reference and are incorporated herein by reference to disclose and describe the materials and/or methods in connection with which the publications are cited. The citation of any publication is for its disclosure prior to the filing date and should not be construed as an admission that the present methods, compositions and kits are not entitled to antedate such publication, as the date of publication provided may be different from the actual publication date which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the methods, compositions and kits, which are, for clarity, described in the context of separate embodiments, may also be provided in combination in a single embodiment. Conversely, various features of the methods, compositions and kits, which are, for brevity, described in the context of a single embodiment, may also be provided separately or in any suitable subcombination. All combinations of the embodiments are specifically embraced by the present disclosure and are disclosed herein just as if each and every combination was individually and explicitly disclosed, to the extent that such combinations embrace operable processes and/or compositions. In addition, all sub-combinations listed in the embodiments describing such variables are also specifically embraced by the present methods, compositions and kits and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present methods, compositions and kits. Any recited method can be carried out in the order of events recited or in any other order that is logically possible.

Methods

As summarized above, provided are methods of producing cobalt-based nanoparticles ($Co_xB_y$ NPs) of a pre-selected diameter. Such methods include nucleating $Co^{2+}$ ions with a sodium borohydride ($NaBH_4$) solution having a selected ratio of tetrahydroxyborate ($B(OH)_4^-$) to tetrahydroborate ($BH_4^-$) based on the pre-selected diameter, wherein the ratio of $B(OH)_4^-$ to $BH_4^-$ is positively correlated with the pre-selected diameter, to produce $Co_xB_y$ NPs of the pre-selected diameter. The methods are based on the inventors' surprising finding that by varying the relative amounts of $BH_4^-$ reducing agent and $B(OH)_4^-$ growth agent, high quality $Co_xB_y$ NPs ranging from ~17-85 nm in hydrodynamic diameter may be prepared, all with relative standard deviation (RSD) <3%. This is believed to be the first demonstration of fine control of $Co_xB_y$ NP diameter over a large size range while maintaining monodispersity.

By "pre-selected diameter" is meant a pre-selected average diameter of the population of $Co_xB_y$ NPs produced. By "pre-selected" is meant the practitioner of the subject methods selects a desired average diameter of the $Co_xB_y$ NPs prior to production of the $Co_xB_y$ NPs, where the desired average diameter of the $Co_xB_y$ NPs is achieved by using a $NaBH_4$ solution having a selected ratio of $B(OH)_4^-$ to $BH_4^-$ that determines the resulting average diameter of the $Co_xB_y$ NPs. The $B(OH)_4^-$:$BH_4^-$ ratio and the pre-selected diameter are positively correlated. Unless specified otherwise, the diameter of an individual $Co_xB_y$ NP is the hydrodynamic diameter of the individual $Co_xB_y$ NP, and the average diameter of a population of $Co_xB_y$ NPs is the average hydrodynamic diameter of $Co_xB_y$ NPs of the population.

The methods of the present disclosure are based in part on the inventors' unexpected findings that the size of $Co_xB_y$ NPs may be "tuned" based on a single parameter—the $B(OH)_4^-$:$BH_4^-$ ratio of the $NaBH_4$ reducing agent used to reduce the $Co^{2+}$ ions, where a $NaBH_4$ reducing agent having a greater $B(OH)_4^-$:$BH_4^-$ ratio produces $Co_xB_y$ NPs having a greater average diameter and a $NaBH_4$ reducing agent having a lower $B(OH)_4^-$:$BH_4^-$ ratio produces $Co_xB_y$ NPs having a lower average diameter. Based on the detailed guidance provided by the present disclosure, one may produce $Co_xB_y$ NPs of a pre-selected diameter by selecting a corresponding $NaBH_4$ reducing agent (having the selected $B(OH)_4^-$:$BH_4^-$ ratio) during $Co_xB_y$ NP synthesis.

In certain aspects, the pre-selected diameter of the $Co_xB_y$ NPs ranges from about 10 to about 200 nm, e.g., from about 17 to about 85 nm. For example, the pre-selected diameter of the $Co_xB_y$ NPs may be about 10 nm, 15 nm, 20 nm, 25 nm, 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, 150 nm, 155 nm, 160 nm, 165 nm, 170 nm, 175 nm, 180 nm, 185 nm, 190 nm, 195 nm, or about 200 nm. In some embodiments, the pre-selected diameter of the $Co_xB_y$ NPs ranges from about 10 to about 200 nm, 10 to 190 nm, 10 to 180 nm, 10 to 170 nm, 10 to 160 nm, 10 to 150 nm, 10 to 140 nm, 10 to 130 nm, 10 to 120 nm, 10 to 110 nm, 10 to 100 nm, 10 to 90 nm, 10 to 80 nm, 10 to 70 nm, 10 to 60 nm, 10 to 50 nm, 10 to 40 nm, 10 to 30 nm, or from about 10 to about 20 nm. In certain aspects, the pre-selected diameter of the $Co_xB_y$ NPs ranges from about 10 to about 200 nm, 20 to 200 nm, 30 to 200 nm, 40 to 200 nm, 50 to 200 nm, 60 to 200 nm, 70 to 200 nm, 80 to 200 nm, 90 to 200 nm, 100 to 200 nm, 110 to 200 nm, 120 to 200 nm, 130 to 200 nm, 140 to 200 nm, 150 to 200 nm, 160 to 200 nm, 170 to 200 nm, 180 to 200 nm, or from about 190 to about 200 nm. In some embodiments, the pre-selected diameter of the $Co_xB_y$ NPs ranges from about 10 to about 20 nm, 20 to 30 nm, 30 to 40 nm, 40 to 50 nm, 50 to 60 nm, 60 to 70 nm, 70 to 80 nm, 80 to 90 nm, 90 to 100 nm, 100 to 110 nm, 110 to 120 nm, 120 to 130 nm, 130 to 140 nm, 140 to 150 nm, 150 to 160 nm, 160 to 170 nm, 170 to 180 nm, 180 to 190 nm, or from about 190 to about 200 nm. In some embodiments, the pre-selected diameter of the $Co_xB_y$ NPs ranges from about 10 to about 20 nm, 20 to 30 nm, 30 to 40 nm, 40 to 50 nm, 45 to 55, 50 to 60 nm, 60 to 70 nm, 70 to 80 nm, 80 to 90 nm, 90 to 100 nm, 110 to 120 nm, 120 to 130 nm, 130 to 140 nm, 140 to 150 nm, 150 to 160 nm, 160 to 170 nm, 170 to 180 nm, 180 to 190 nm, or from about 190 to about 200 nm. In certain aspects, the pre-selected diameter of the $Co_xB_y$ NPs ranges from about 30 to about 230 nm, from 40 to 220 nm, from 50 to 210 nm, from 60 to 200 nm, from 70 to 190 nm, from 80 to 180 nm, from 90 to 170 nm, from 100 to 160 nm, from 110 to 150 nm, or from 120 to 140 nm. In some embodiments, the pre-selected diameter of the $Co_xB_y$ NPs ranges from about 110 nm to about 150 nm, e.g., about 115 nm to about 145 nm. In certain aspects, the pre-selected diameter of the $Co_xB_y$ NPs is 10 nm or more, 20 nm or more, 30 nm or more, 40 nm or more, 50 nm or more, 60 nm or more, 70 nm or more, 80 nm or more, 90 nm or more, 100 nm or more, 110 nm or more, 120 nm or more, 130 nm or more, 140 nm or more, 150 nm or more, 160 nm or more, 170 nm or more, 180 nm or more, 190 nm or more, or 200 nm or more. In some embodiments, the pre-selected diameter of the $Co_xB_y$ NPs is 200 nm or less, 190 nm or less, 180 nm or less, 170 nm or less, 160 nm or less, 150 nm or less, 140 nm or less, 130 nm or less, 120 nm or less, 110 nm or less, 100 nm or less, 90 nm or less, 80 nm or less, 70 nm or less, 60 nm or less, 50 nm or less, 40 nm or less, 30 nm or less, 20 nm or less, or 10 nm or less. In some embodiments, the pre-selected diameter of the $Co_xB_y$ NPs is from about 45 nm to about 55 nm, e.g., from about 46 nm to about 54 nm, from about 47 nm to about 53 nm, from about 48 to about 52 nm, from about 49 to about 51 nm, e.g., about 50 nm.

In some embodiments, the pre-selected diameter of the $Co_xB_y$ NPs is achieved by selecting a $B(OH)_4^-$:$BH_4^-$ ratio of from about 0.1 to about 4, such as from about 0.1 to 3.8, 0.1 to 3.6, 0.1 to 3.4, 0.1 to 3.2, 0.1 to 3.0, 0.1 to 2.8, 0.1 to 2.6, 0.1 to 2.4, 0.1 to 2.2, 0.1 to 2.0, 0.1 to 1.8, 0.1 to 1.6, 0.1 to 1.4, 0.1 to 1.2, 0.1 to 1.0, 0.1 to 0.8, 0.1 to 0.6, 0.1 to 0.4, or from about 0.1 to about 0.2. In certain aspects, the pre-selected diameter of the $Co_xB_y$ NPs is achieved using a $B(OH)_4^-$:$BH_4^-$ ratio of from about 0.1 to about 4, such as from about 0.2 to 4, 0.4 to 4, 0.6 to 4, 0.8 to 4, 1.0 to 4, 1.2 to 4, 1.4 to 4, 1.6 to 4, 1.8 to 4, 2.0 to 4, 2.2 to 4, 2.4 to 4, 2.6 to 4, 2.8 to 4, 3.0 to 4, 3.2 to 4, 3.4 to 4, 3.6 to 4, or about 3.8 to about 4. In certain aspects, the pre-selected diameter of the $Co_xB_y$ NPs is achieved using a $B(OH)_4^-:BH_4^-$ ratio of from about 0.5 to about 1.

In some embodiments, the pre-selected diameter of the $Co_xB_y$ NPs is from about 15 nm to about 25 nm, and the $B(OH)_4^-:BH_4^-$ ratio is 0, meaning that no or substantially no $B(OH)_4^-$ is present during the nucleating. In certain aspects, the pre-selected diameter of the $Co_xB_y$ NPs is from about 25 nm to about 45 nm, and the $B(OH)_4^-:BH_4^-$ ratio employed is 0.5 or less, e.g., from about 0.1 to about 0.5. In some embodiments, the pre-selected diameter of the $Co_xB_y$ NPs is from about 43 nm to about 56 nm, and the $B(OH)_4^-:BH_4^-$ ratio employed is from about 0.5 to about 1.0. In certain aspects, the pre-selected diameter of the $Co_xB_y$ NPs is from about 45 nm to about 65 nm, and the $B(OH)_4^-:BH_4^-$ ratio employed is from about 0.5 to about 1.5. In some embodiments, the pre-selected diameter of the $Co_xB_y$ NPs is from about 65 nm to about 100 nm, and the $B(OH)_4^-:BH_4^-$ ratio employed is from about 1.5 to about 5.0.

Any convenient approach may be implemented for producing the $NaBH_4$ solution having the selected ratio of $B(OH)_4^-$ to $BH_4^-$. $B(OH)_4^-$ is the final product of $NaBH_4$ hydrolysis. As such, one may produce $B(OH)_4^-$ by hydrolyzing $NaBH_4$ (e.g., completely), and then adding an appropriate amount of $B(OH)_4^-$ to an unhydrolyzed $NaBH_4$ solution (or an $NaBH_4$ solution having undergone a known extent of hydrolysis) used as the nucleating agent in a $Co_xB_y$ NP synthesis reaction, or adding an appropriate amount of $B(OH)_4^-$ to a $Co_xB_y$ NP synthesis reaction mixture to which an unhydrolyzed $NaBH_4$ solution (or an $NaBH_4$ solution having undergone a known extent of hydrolysis) has been or will be added. In certain aspects, a $NaBH_4$ solution having the selected ratio of $B(OH)_4^-$ to $BH_4^-$ is produced by hydrolyzing an unhydrolyzed or substantially unhydrolyzed $NaBH_4$ solution under conditions determined/known to produce a $NaBH_4$ solution having the selected ratio of $B(OH)_4^-$ to $BH_4^-$. Such conditions may include: no stirring, or stirring at a particular rate (e.g., using a stir bar at a particular rpm); a duration of the hydrolysis (e.g., about 2 hours, about 4 hours, about 6 hours, about 8 hours, about 10 hours, about 12 hours, about 14 hours, about 16 hours, about 18 hours, about 20 hours, about 22 hours, about 24 hours, about 26 hours, about 28 hours, about 30 hours, about 32 hours, about 34 hours, about 36 hours, about 38 hours, about 40 hours, about 42 hours, about 44 hours, about 46 hours, or about 48 hours); or any combination thereof.

In some embodiments, the pre-selected diameter of the $Co_xB_y$ NPs is achieved by selecting a $BH_4^-:Co^{2+}$ ratio. The $BH_4^-:Co^{2+}$ ratio may or may not be in combination with a selected $B(OH)_4^-:BH_4^-$ ratio, e.g., any of the $B(OH)_4^-:BH_4^-$ ratios recited in the preceding paragraph. In certain aspects, the pre-selected diameter of the $Co_xB_y$ NPs is achieved by selecting—optionally in combination with a selected $B(OH)_4^-:BH_4^-$ ratio—a $BH_4^-:Co^{2+}$ ratio of from about 0.1 to about 12, such as from about 0.1 to 11.6, 0.1 to 11.2, 0.1 to 10.8, 0.1 to 10.4, 0.1 to 10.0, 0.1 to 9.6, 0.1 to 9.2, 0.1 to 8.8, 0.1 to 8.4, 0.1 to 8.0, 0.1 to 7.6, 0.1 to 7.2, 0.1 to 6.8, 0.1 to 6.4, 0.1 to 6.0, 0.1 to 5.6, 0.1 to 5.2, 0.1 to 4.8, 0.1 to 4.4, 0.1 to 4.0, 0.1 to 3.6, 0.1 to 3.2, 0.1 to 2.8, 0.1 to 2.4, 0.1 to 2.0, 0.1 to 1.6, 0.1 to 1.2, 0.1 to 0.8, or from about 0.1 to about 0.4. In some embodiments, the pre-selected diameter of the $Co_xB_y$ NPs is achieved by selecting—optionally in combination with a selected $B(OH)_4^-:BH_4^-$ ratio—a $BH_4^-:Co^{2+}$ ratio of from about 0.1 to about 12, such as from about 0.4 to 12, 0.8 to 12, 1.2 to 12, 1.6 to 12, 2.0 to 12, 2.4 to 12, 2.8 to 12, 3.2 to 12, 3.6 to 12, 4.0 to 12, 4.4 to 12, 4.8 to 12, 5.2 to 12, 5.6 to 12, 6.0 to 12, 6.4 to 12, 6.8 to 12, 7.2 to 12, 7.6 to 12, 8.0 to 12, 8.4 to 12, 8.8 to 12, 9.2 to 12, 9.6 to 12, 10.0 to 12, 10.4 to 12, 10.8 to 12, 11.2 to 12, or from about 11.6 to about 12. In certain aspects, the pre-selected diameter of the $Co_xB_y$ NPs is achieved by selecting—optionally in combination with a selected $B(OH)_4^-:BH_4^-$ ratio—a $BH_4^-:Co^{2+}$ ratio of from about 0.5 to about 6.0, such as from about 2.0 to about 5.0, e.g., about 2.5 to about 5.0.

The $BH_4^-:Co^{2+}$ ratio in the nucleation reaction may be achieved using any convenient approach. For example, a desired $BH_4^-:Co^{2+}$ ratio may be achieved by adding an appropriate volume of an $NaBH_4$ solution (e.g., having a selected $B(OH)_4^-:BH_4^-$ ratio) to a solution comprising a known concentration of $Co^{2+}$ ions. Different $BH_4^-:Co^{2+}$ ratios may be achieved in separate $Co_xB_y$ NP synthesis reactions by, e.g., adding different appropriate volumes of an $NaBH_4$ solution (e.g., having a selected $B(OH)_4^-:BH_4^-$ ratio) to separate solutions comprising known concentrations of $Co^{2+}$ ions.

In some embodiments, the pre-selected diameter of the $Co_xB_y$ NPs is less than about 25 nm, the $B(OH)_4^-:BH_4^-$ ratio is 0, meaning that no or substantially no $B(OH)_4^-$ is present during the nucleating, and the $BH_4^-:Co^{2+}$ ratio is 12.5 or less. In certain aspects, the pre-selected diameter of the $Co_xB_y$ NPs is from about 25 nm to about 45 nm, the $B(OH)_4^-:BH_4^-$ ratio is 1.0 or less, and the $BH_4^-:Co^{2+}$ ratio is 12.5 or less. In some embodiments, the pre-selected diameter of the $Co_xB_y$ NPs is from about 45 nm to about 65 nm, the $B(OH)_4^-:BH_4^-$ ratio is from about 0.5 to about 2.0, and the $BH_4^-:Co^{2+}$ ratio is from about 2.5 to about 5. In certain aspects, the pre-selected diameter of the $Co_xB_y$ NPs is from about 65 nm to about 100 nm, the $B(OH)_4^-:BH_4^-$ ratio is from about 2.0 to about 5.0, and the $BH_4^-:Co^{2+}$ ratio is from about 1.0 to about 2.5.

As will be appreciated, the diameters of individual $Co_xB_y$ NPs produced according to subject methods will vary around the pre-selected diameter. In some embodiments, the diameters of the $Co_xB_y$ NPs produced will vary around the pre-selected diameter (e.g., any of the pre-selected diameters provided in the preceding paragraph) by 20% or less, 17.5% or less, 15% or less, 12.5% or less, 10% or less, 7.5% or less, 5% or less, 4% or less, 3% or less, 2.5% or less, 2% or less, 1.5% or less, or 1% or less.

As demonstrated in the Experimental section herein, the subject methods for producing $Co_xB_y$ NPs enable fine control of $Co_xB_y$ NP diameter over a large size range while maintaining monodispersity. "Dispersity" is a measure of the heterogeneity of sizes of particles in a mixture. By "monodisperse" is meant the particles are of uniform size in a dispersed phase. Monodispersity may be readily assessed using any convenient approach, a non-limiting example of which is Dynamic Light Scattering (DLS). As described in detail in the Experimental section herein, DLS may be performed to determine the mean hydrodynamic diameter of $Co_xB_y$ NPs synthesized in accordance with the subject methods. The reported ±values represent one standard deviation from the mean. Relative standard deviation (RSD) represents one standard deviation as a percentage of the mean, using unrounded values for calculation. The monodispersity of $Co_xB_y$ NPs produced according to the present methods may be expressed in terms of relative standard deviation (RSD). In some embodiments, the $Co_xB_y$ NPs produced exhibit an RSD of 5% or less, 4.5% or less, 4% or less, 3.5% or less, 3% or less, 2.5% or less, 2% or less, 1.5% or less, or 1% or less.

In certain aspects, the nucleating includes combining a cobalt salt including the $Co^{2+}$ ions, a capping agent (or "capping ligand"), and the NaBH$_4$ solution having the selected ratio of B(OH)$_4^-$ to BH$_4^-$. Example suitable conditions for the combining are described in detail in the Experimental section herein. In some embodiments, the combining includes combining a deaerated solution comprising the cobalt salt and the capping agent, and the NaBH$_4$ solution having the selected ratio of B(OH)$_4^-$ to BH$_4^-$. In certain aspects, each of the cobalt salt, capping agent and NaBH$_4$ solution are deaerated prior to and/or during the combining.

As used herein, "deaerated" means dissolved air or gas (e.g., oxygen) has been partially or completely removed from a liquid, e.g., a solution. For example, "deaerated" may mean that—as compared to the liquid prior to deaeration—dissolved air or gas in the liquid is reduced by about 50% or more, 60% or more, 70% or more, 80% or more, 90% or more, 95% or more, 98% or more, 99% or more, or by about 100%. Any suitable approaches for deaerating a liquid of interest may be employed. In one non-limiting example, deaeration is performed by bubbling the liquid with an inert gas (e.g., nitrogen, argon, helium, or the like) for a suitable period of time, e.g., 1 hour or more. A vacuum gas manifold, such as a Schlenk line, may be used to deaerate a liquid of interest.

The cobalt salt including the Co$^{2+}$ ions may be any cobalt salt suitable for synthesis of cobalt or cobalt-based nanoparticles, which salt may be selected based on the type of capping agent and/or any other reagents employed for Co-based NP synthesis. In some embodiments, the cobalt salt is an anhydrous cobalt salt. A non-limiting example of an anhydrous cobalt salt that may be employed when practicing the subject methods is CoCl$_2$. Other suitable cobalt salts include, but are not limited to, CoBr$_2$, CoI$_2$, Co(NO$_3$)$_2$, Co(acac)$_2$, Cobalt(II) acetate, etc.

The capping agent may be any capping agent suitable for synthesis of cobalt-based nanoparticles, which capping agent may be selected based on the type of cobalt salt, reducing agent, and/or any other reagents employed for Co-based NP synthesis. In some embodiments, the capping agent is a sodium salt of citrate. A non-limiting example of a capping agent that is a sodium salt of citrate is trisodium citrate. Other suitable capping agents include, but are not limited to, polyvinylpyrrolidone (PVP), polyethylene glycol (PEG), polyvinyl alcohol (PVA), polyethyleneimine (PEI), cetyltrimethyl ammonium bromide (CTA-Br), cetyltrimethyl ammonium chloride (CTA-Cl), etc.

In certain aspects, the nucleating is performed in an anaerobic environment. By "anaerobic environment" is meant that the reaction occurs in the absence or substantially in the absence of oxygen. For any of the reactions described herein, an anaerobic environment may be established by performing the reaction under the protection of an inert gas, such as nitrogen, argon, helium, or the like. Example approaches for performing various steps of the subject methods in an anaerobic environment are described in the Experimental section herein.

In some embodiments, the methods further include producing Co$_x$B$_y$ NPs of a different pre-selected diameter by nucleating Co$^{2+}$ ions with a sodium borohydride (NaBH$_4$) solution having a different selected ratio of tetrahydroxyborate (B(OH)$_4^-$) to tetrahydroborate (BH$_4^-$) based on the different pre-selected diameter, where the different ratio of (B(OH)$_4^-$) to BH$_4^-$ is positively correlated with the different pre-selected diameter, to produce Co$_x$B$_y$ NPs of the different pre-selected diameter.

In certain aspects, the methods further include, subsequent to producing the Co$_x$B$_y$ NPs, producing hollow metal nanospheres (HMNs) using the Co$_x$B$_y$ NPs as scaffolds. HMNs of interest include, but are not limited to, hollow gold nanospheres (HGNs), hollow silver nanospheres (HSNs), etc. Producing the HMNs may include producing Co$_x$B$_y$ NP core/metal shell structures via a galvanic exchange reaction. In some embodiments, the galvanic exchange reaction is performed in an anaerobic environment. When the methods include a galvanic exchange reaction, the galvanic exchange reaction may include combining a solution including the Co$_x$B$_y$ NPs of the pre-selected diameter, and a solution including a metal. In certain aspects, the solution including the metal is deaerated prior to the combining with the solution including the Co$_x$B$_y$ NPs of the pre-selected diameter. By way of example, if the HMNs to be produced are HGNs, the solution including a metal is a deaerated solution including gold, a non-limiting example of which is a deaerated HAuCl$_4$ solution.

Producing HMNs from the Co$_x$B$_y$ NPs of the pre-selected diameter may further include oxidizing the Co$_x$B$_y$ NP cores of the Co$_x$B$_y$ NP core/metal shell structures. The oxidizing may be by oxygenation. In certain aspects, the oxygenation is controlled oxygenation. Controlled oxygenation may include introducing air or pure oxygen into a previously anaerobic environment containing the Co$_x$B$_y$ NP core/metal shell structures produced by galvanic exchange. The rate of introduction may be controlled, e.g., by stirring a solution including the Co$_x$B$_y$ NP core/metal shell structures in an aerobic environment at a selected rate, such as by swirling or using a stir bar and stirring the solution at a selected rpm.

As demonstrated in the Experimental section below, HGNs produced from the Co$_x$B$_y$ NP scaffolds will have a diameter primarily determined by the pre-selected diameter of the Co$_x$B$_y$ NPs. In this way, the present disclosure provides the size-tunable synthesis of HMNs by controlling the ratio of B(OH)$_4^-$ to BH$_4^-$ during Co$_x$B$_y$ NP synthesis. In other words, the HMN diameter may be pre-selected based on the pre-selected diameter of the Co$_x$B$_y$ NPs achieved by appropriate selection of the ratio of B(OH)$_4^-$ to BH$_4^-$ during Co$_x$B$_y$ NP synthesis. Accordingly, in some embodiments, the methods of the present disclosure are methods of tuning HMNs (e.g., HGNs) to have a particular property (e.g., spectral property, photothermal property, and/or the like) where the property is based at least in part on the average diameters of the HMNs as determined by the pre-selected diameter of the Co$_x$B$_y$ NPs, which pre-selected diameter is achieved by the selected ratio of B(OH)$_4^-$ to BH$_4^-$ during Co$_x$B$_y$ NP synthesis. Unless specified otherwise, the diameter of an individual HGN is the largest linear dimension of the individual HGN (rather than the hydrodynamic diameter of the individual HGN), and the average diameter of a population of HGNs is the average of the largest linear dimension of HGNs of the population (rather than the average hydrodynamic diameter of HGNs of the population).

In some embodiments, HMNs (e.g., HGNs) produced in accordance with the methods of the present disclosure have an average diameter of from about 10 to about 200 nm (e.g., from about 20 to about 150 nm), where the average HMN (e.g., HGN) diameter is determined by the pre-selected diameter of the Co$_x$B$_y$ NPs. For example, the average HMN diameter may be about 10 nm, 15 nm, 20 nm, 25 nm, 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, 150 nm, 155 nm, 160 nm, 170 nm, 180 nm, 190 nm, or about 200 nm. In some embodiments, the average HMN diameter ranges from about 10 to about 20 nm, 20 to 30 nm, 30 to 40 nm, 40 to 50 nm, 50 to 60 nm, 60 to 70 nm, 70 to 80 nm, 80 to 90 nm, 90 to 100 nm, 100 to 105 nm, 105 to 110 nm, 110 to 115 nm, 115 to 120 nm, 120 to 125 nm, 125 to 130 nm, 130 to 135 nm, 135 to 140 nm, 140 to 145 nm, 145 to 150 nm, 150 to 155 nm, 155 to 160 nm, 160 to 165 nm, 165 to 170 nm, 170 to 175 nm, 175 to 180 nm, 180 to 185 nm, 185 to 190 nm, 190 to 195 nm, or about 195 to about 200 nm. In certain aspects, the average HMN diameter is from about 50 to about 170 nm, from 60 to 160 nm, from 70 to 150 nm, from 80 to 140 nm, from 90 to 130 nm, or from about 100 to about 120 nm. In some embodiments, the average HMN diameter is 10 nm or more, 20 nm or more, 30 nm or more, 40 nm or more, 50 nm or more, 60 nm or more, 70 nm or more, 80 nm or more, 90 nm or more, 100 nm or more, 110 nm or more, 120 nm or more, 130 nm or more, 140 nm or more, 150 nm or more, 160 nm or more, 170 nm or more, 180 nm or more, 190 nm or more, or 200 nm or more. In certain aspects, the average HMN diameter is 200 nm or less, 190 nm or less, 180 nm or less, 170 nm or less, 160 nm or less, 150 nm or less, 140 nm or less, 130 nm or less, 120 nm or less, 110 nm or less, 100 nm or less, 90 nm or less, 80 nm or less, 70 nm or less, 60 nm or less, 50 nm or less, 40 nm or less, 30 nm or less, 20 nm or less, or 10 nm or less. In some embodiments, the average HMN (e.g., HGN) diameter is from about 45 nm to about 55 nm, e.g., from about 46 nm to about 54 nm, from about 47 nm to about 53 nm, from about 48 to about 52 nm, or from about 49 to about 51 nm, e.g., about 50 nm.

As will be appreciated, the diameters of individual HMNs produced according to subject methods will vary around the average diameter. In some embodiments, the diameters of the HMNs produced will vary around the average diameter (e.g., any of the average diameters provided in the preceding paragraph) by 20% or less, 17.5% or less, 15% or less, 12.5% or less, 10% or less, 7.5% or less, 5% or less, 2.5% or less, 2.0% or less, 1.5% or less, or 1% or less.

The monodispersity of HMNs produced according to the present methods may be expressed in terms of relative standard deviation (RSD). In some embodiments, the HMNs produced exhibit an RSD of 5% or less, 4.5% or less, 4% or less, 3.5% or less, 3% or less, 2.5% or less, 2% or less, 1.5% or less, or 1% or less.

HMNs (e.g., HGNs) produced according to the methods of the present disclosure may exhibit optical properties, photothermal properties, and/or the like determined by their average diameter and/or aspect ratio, which in turn is determined by the pre-selected diameter of the $Co_xB_y$ NPs produced using the selected ratio of $B(OH)_4^-$ to $BH_4^-$. In certain aspects, the produced HMNs exhibit a surface plasmon resonance (SPR) absorption with a maximum peak position in the visible range, e.g., from about 400 to about 700 nm. In some embodiments, the produced HMNs (e.g., HGNs) exhibit an SPR absorption with a maximum peak position in the infrared range (which is 700 nm to 1 mm), e.g., from about 700 nm to about 1 µm. In certain aspects, the produced HMNs (e.g., HGNs) exhibit an SPR absorption with a maximum peak position in the near-infrared (near-IR) range, e.g., from about 700 nm to about 2500 nm. In some embodiments, the produced HMNs (e.g., HGNs) exhibit an SPR absorption with a maximum peak position of from about 400 to about 1200 nm (e.g., from about 565 to about 850 nm), such as from 420 to 1180 nm, from 440 to 1160 nm, from 460 to 1140 nm, from 480 to 1120 nm, from 500 to 1100 nm, from 520 to 1080 nm, from 540 to 1060 nm, from 560 to 1040 nm, from 580 to 1020 nm, from 600 to 1000 nm, from 620 to 980 nm, from 640 to 960 nm, from 660 to 940 nm, from 680 to 920 nm, from 700 to 900 nm, from 720 to 880 nm, from 740 to 860 nm, from 760 to 840 nm, from 780 to 820 nm, from 785 to 815 nm, from 790 to 810 nm, or from about 795 to about 805 nm, e.g., about 800 nm.

In some embodiments, methods that include producing HMNs using the $Co_xB_y$ NPs as scaffolds may further include attaching a moiety (e.g., a targeting moiety) to the surface of the HMNs. In certain aspects, a targeting moiety selected from an antibody, a ligand, an aptamer, a nucleic acid, and a small molecule, is attached to the surface of the HMNs. By "targeting moiety" is meant a moiety that directly or indirectly binds to a target. Targets of interest include analytes (e.g., proteins, nucleic acids, small molecules, or the like), cells (e.g., cells in an in vitro or in vivo environment), and the like.

In certain aspects, the HMNs include a targeting moiety (e.g., an antibody, cell surface receptor ligand, or the like) that binds to a molecule on the surface of a target cell in vitro or in vivo. Such HMNs find use in research, diagnostic, and/or therapeutic applications. In some embodiments, the target cell is a cancer cell. By "cancer cell" is meant a cell exhibiting a neoplastic cellular phenotype, which may be characterized by one or more of, for example, abnormal cell growth, abnormal cellular proliferation, loss of density dependent growth inhibition, anchorage-independent growth potential, ability to promote tumor growth and/or development in an immunocompromised non-human animal model, and/or any appropriate indicator of cellular transformation. "Cancer cell" may be used interchangeably herein with "tumor cell", "malignant cell" or "cancerous cell", and encompasses cancer cells of a solid tumor, a semi-solid tumor, a primary tumor, a metastatic tumor, and the like. In some embodiments, the HMNs include a targeting moiety (e.g., an antibody, cell surface receptor ligand, or the like) that binds to a tumor-associated or tumor-specific cell surface molecule, e.g., cell surface receptor, membrane protease, and the like. By "tumor-associated cell surface molecule" is meant a cell surface molecule expressed on malignant cells with limited expression on cells of normal tissues, a cell surface molecule expressed at much higher density on malignant versus normal cells, or a cell surface molecule that is developmentally expressed.

Any tumor-associated cell surface molecule or tumor-specific cell surface molecule may be targeted by the HMNs of the present disclosure. In certain aspects, the target on the cancer cell surface to which the targeting moiety of the HMNs binds is EGFR, HER2, CD19, CD22, CD30, CD33, CD56, CD66/CEACAM5, CD70, CD74, CD79b, CD138, Nectin-4, Mesothelin, Transmembrane glycoprotein NMB (GPNMB), Prostate-Specific Membrane Antigen (PSMA), SLC44A4, CA6, CA-IX, $\alpha v \beta 1$ integrin, $\alpha v \beta 3$ integrin, $\alpha v \beta 5$ integrin, $\alpha v \beta 6$ integrin, $\alpha 5 \beta 1$ integrin, C-X-C chemokine receptor type 4 (CXCR4), cytotoxic T-lymphocyte-associated protein 4 (CTLA-4), neuropilin-1 (NRP1), matriptase, or any other tumor-associated or tumor-specific cell surface molecule of interest.

A variety of suitable approaches exist for attaching a targeting moiety to HMNs. In one non-limiting example, thiol-based surface functionalization of the HMNs may be employed. For example, bifunctional SH-PEG-COOH linkers have been employed to conjugate antibodies to HMNs, the details of which may be found, e.g., in Liu et al. (2015) *Nanoscale Res. Lett.* 10:218. Briefly, the SH-PEG-COOH linker may be reacted with the HMNs, followed by addition of N-(3-dimethylaminopropyl)-N-ethylcarbodiimidehydrochloride (EDC) and N-hydroxy succinimide (NHS) to activate the carboxyl terminal of PEG, followed by combining the PEGylated HMNs with the antibody of interest. In some embodiments, an orthopyridyl disulfides-poly(ethylene) glycol-succinimidyl valerate (OPSS-PEG-SVA) linker is used to attach a targeting moiety to HMNs.

Also provided are HMNs (e.g., HGNs) produced according to any of the methods of the present disclosure. The HMNs may be present in a container, such as a vial, tube, plate (e.g., 96-well or other plate), flask, or the like. In some embodiments, the HMNs are present in a liquid medium, e.g., water or other suitable liquid storage medium. In certain aspects, the HMNs are present in a lyophilized form.

The present disclosure also provides methods of using the produced HMNs (e.g., HGNs) in a variety of applications. Non-limiting examples of such applications include surface-enhanced Raman scattering (SERS),[5-6] photothermal therapy (PTT),[7-8] plasmonic enhanced photoelectric conversion, chemical catalysis[9] and biosensors.[10-15]

In one example, HMNs (e.g., HGNs) produced according to the methods of the present disclosure are used for photothermal therapy (PTT). PTT involves embedding nanoparticles within tumors, which nanoparticles generate heat in response to exogenously applied laser light, thereby killing tumor cells in the vicinity of the nanoparticles. The preferred mediators of PTT are gold-based nanoparticles because they offer: (1) simple gold-thiol bioconjugation chemistry for the attachment of desired targeting molecules; (2) biocompatibility, (3) efficient light-to-heat conversion; (4) small diameters that enable tumor penetration upon systemic delivery, and (5) the ability to be tuned to absorb near-infrared light, which penetrates tissue more deeply than other wavelengths of light. PTT may be used in combination with other therapies, such as chemotherapy, gene regulation, and immunotherapy, for enhanced anti-tumor effects. Details regarding PTT approaches that may be practiced employing HMNs produced according to methods of the present disclosure may be found, e.g., in Riley R. S. & Day, E. S. (2017) *Wiley Interdiscip. Rev. Nanomed. Nanobiotechnol.* 2017 9(4); Melancon et al. (2008) *Mol. Cancer Ther.* 7:1730; and Lu et al. (2009) *Clin. Cancer Res.* 15:876.

Accordingly, provided are methods that include administering HMNs (e.g., HGNs) produced according to the methods of the present disclosure to an individual in need thereof. In some embodiments, the individual in need thereof is in need of photothermal therapy (PTT), e.g., an individual having cancer. In certain aspects, the HMNs (e.g., HGNs) include a targeting moiety that binds to a molecule on the surface of a target cell (e.g., a cancer cell) of the individual.

Compositions

Also provided are compositions that include the $Co_xB_y$ NPs or HMNs (e.g., HGNs) of the present disclosure. The compositions may include any of the $Co_xB_y$ NPs or HMNs described herein. In certain aspects, the compositions include the $Co_xB_y$ NPs or HMNs present in a liquid medium. The liquid medium may be an aqueous liquid medium, such as water, a buffered solution, and the like. One or more additives such as a salt (e.g., NaCl, MgCl2, KCl, MgSO4), a buffering agent (a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino) propanesulfonic acid (MOPS), N-tris[Hydroxymethyl] methyl-3-aminopropanesulfonic acid (TAPS), etc.), a solubilizing agent, a detergent (e.g., a non-ionic detergent such as Tween-20, etc.), glycerol, a chelating agent, and the like may be present in such compositions.

Pharmaceutical compositions are also provided. The pharmaceutical compositions include any of the HMNs (e.g., HGNs) of the present disclosure, and a pharmaceutically acceptable carrier. The pharmaceutical compositions generally include a therapeutically effective amount of the HMNs, e.g., for use in photothermal therapy. By "therapeutically effective amount" is meant a dosage sufficient to produce a desired result, e.g., an amount sufficient to effect beneficial or desired therapeutic (including preventative) results, such as a reduction in a symptom of a disease or disorder (e.g., a cell proliferative disorder such as cancer), as compared to a control. An effective amount can be administered in one or more administrations.

The HMNs of the present disclosure can be incorporated into a variety of formulations for therapeutic administration, e.g., oral, parenteral, or other routes of administration. More particularly, the HMNs can be formulated into pharmaceutical compositions by combination with appropriate, pharmaceutically acceptable excipients or diluents, and may be formulated into preparations in solid, semi-solid, liquid or gaseous forms, such as tablets, capsules, powders, granules, ointments, solutions, injections, inhalants and aerosols.

Formulations of the HMNs suitable for administration to a patient (e.g., suitable for human administration) are generally sterile and may further be free of detectable pyrogens or other contaminants contraindicated for administration to a patient according to a selected route of administration.

The HMNs can be formulated into preparations for injection by dissolving, suspending or emulsifying them in an aqueous or non-aqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Pharmaceutical compositions that include the HMNs may be prepared by mixing the HMNs having the desired degree of purity with optional physiologically acceptable carriers, excipients, stabilizers, surfactants, buffers and/or tonicity agents. Acceptable carriers, excipients and/or stabilizers are nontoxic to recipients at the dosages and concentrations employed, and include buffers such as phosphate, citrate, and other organic acids; antioxidants including ascorbic acid, glutathione, cysteine, methionine and citric acid; preservatives (such as ethanol, benzyl alcohol, phenol, m-cresol, p-chlor-m-cresol, methyl or propyl parabens, benzalkonium chloride, or combinations thereof); amino acids such as arginine, glycine, ornithine, lysine, histidine, glutamic acid, aspartic acid, isoleucine, leucine, alanine, phenylalanine, tyrosine, tryptophan, methionine, serine, proline and combinations thereof; monosaccharides, disaccharides and other carbohydrates; low molecular weight (less than about 10 residues) polypeptides; proteins, such as gelatin or serum albumin; chelating agents such as EDTA; sugars such as trehalose, sucrose, lactose, glucose, mannose, maltose, galactose, fructose, sorbose, raffinose, glucosamine, N-methylglucosamine, galactosamine, and neuraminic acid; and/or non-ionic surfactants such as Tween, Brij Pluronics, Triton-X, or polyethylene glycol (PEG).

The pharmaceutical composition may be in a liquid form, a lyophilized form or a liquid form reconstituted from a lyophilized form, wherein the lyophilized preparation is to be reconstituted with a sterile solution prior to administration. The standard procedure for reconstituting a lyophilized composition is to add back a volume of pure water (typically equivalent to the volume removed during lyophilization); however solutions comprising antibacterial agents may be used for the production of pharmaceutical compositions for parenteral administration.

Kits

As summarized above, the present disclosure provides kits. In certain aspects, provided are kits that include cobalt-based nanoparticles ($Co_xB_y$ NPs) of a selected diameter produced according to any of the methods of the present disclosure. The kits may further include instructions for using the $Co_xB_y$ NPs to produce hollow metal nanospheres (HMNs, such as HGNs), e.g., via a galvanic exchange reaction or other suitable reaction for producing HMNs from $Co_xB_y$ NPs. In some embodiments, such kits include two or more populations of $Co_xB_y$ NPs (provided in the same container or separate containers) each having different average diameters and produced using different selected ratios of $B(OH)_4^-$ to $BH_4^-$ according to any of the methods of the present disclosure. The kits that include $Co_xB_y$ NPs may further include one or more reagents for producing HMNs from the $Co_xB_y$ NPs. As just one example, such kits may include one or more reagents for producing HMNs by galvanic exchange. In certain aspects, the one or more reagents for producing HMNs by galvanic exchange includes $HAuCl_4$. The kits may further include one or more reagents and accompanying instructions for functionalizing the surface of the HMNs, e.g., by attaching a linker and/or moiety (e.g., a targeting moiety such as an antibody, or the like) to the surface of the HMNs. In one example, the kits include a thiol-based surface functionalization reagent, e.g., a bifunctional thiol-based linker, such as an SH-PEG-COOH linker. In some embodiments, the kits include a orthopyridyl disulfides poly(ethylene) glycolsuccinimidyl valerate (OPSS-PEG-SVA) functionalization reagent. In some embodiments, the targeting moiety is one that binds to a molecule on the surface of a target cell (e.g., a cancer cell) in vitro or within an individual.

In some embodiments, provided are kits that include hollow metal nanospheres (HMNs, such as HGNs) produced according to the methods of the present disclosure, or a pharmaceutical composition including such HMNs. Such kits may include instructions for employing the HMNs in a variety of research, diagnostic and/or therapeutic applications. In certain aspects, the kits include instructions for using the HMNs to detect an analyte in vitro (e.g., biosensing, such as in vitro analyte detection, or the like) or in vivo (e.g., in vivo imaging, such as in vivo tumor imaging, or the like). Alternatively, or additionally, the kits may include instructions for administering the HMNs to an individual in need thereof, e.g., an individual in need of photothermal therapy (PTT), such as an individual having cancer. Kits that include HMNs for therapeutic applications may include the HMNs present in one or more (e.g., two or more) unit dosages.

Kits that include HMNs may further include one or more reagents and accompanying instructions for functionalizing the surface of the HGNs, e.g., by attaching a linker and/or moiety (e.g., a targeting moiety such as an antibody, or the like) to the surface of the HMNs. In one example, the kits include a thiol-based surface functionalization reagent, e.g., a bifunctional thiol-based linker, such as an SH-PEG-COOH linker. In some embodiments, the targeting moiety is one that binds to a molecule on the surface of a target cell (e.g., a cancer cell) in vitro or within an individual.

In some embodiments, provided are kits that include any of the HMNs, compositions, or pharmaceutical compositions of the present disclosure, and instructions for using the HMNs to detect an analyte in vitro or in vivo. In certain aspects, provided are kits that include any of the HMNs, compositions, or pharmaceutical compositions of the present disclosure, and instructions for administering the HMNs to an individual in need thereof.

Components of the kits may be present in separate containers, or multiple components may be present in a single container. For example, in a kit that includes reagents for producing $Co_xB_y$ NPs and/or reagents for producing HMNs, two or more of such reagents may be provided in the same tube, or may be provided in different tubes.

In addition to the above-mentioned components, and as described above, a subject kit may further include instructions for using the components of the kit, e.g., to practice the methods of the present disclosure. The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, Hard Disk Drive (HDD) etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

The following examples are offered by way of illustration and not by way of limitation.

EXPERIMENTAL

Example 1—Hollow Gold Nanosphere (HGN) Synthesis with Deaeration of Gold and Anaerobic Galvanic Exchange Described in this example is an approach for synthesizing hollow gold nanospheres (HGNs) which differs from previous approaches in several ways, primarily in the deaeration of gold and anaerobic galvanic exchange. The approach described herein provides for improved monodisperity and minimizes aberrant particle formation.

I. General Description

The synthesis reported herein comprises four main steps: (1) $Co_xB_y$ scaffold preparation; (2) gold salt preparation; (3) galvanic exchange; and (4) $Co_xB_y$ core oxidation. Details regarding these steps are described below.

(1) Cobalt Scaffold Preparation

Cobalt nanoparticle ($Co_xB_y$ NP) scaffolds were prepared via nucleation of aqueous cobalt (II) chloride with sodium borohydride as the reducing agent and sodium citrate as a capping ligand. First, a solution of cobalt (II) chloride and sodium citrate was stirred (with a magnetic stir bar) and deaerated by bubbling with nitrogen gas. Argon gas may also be used. After deaeration, the gas needle was suspended above the solution and aqueous sodium borohydride was injected into the flask. The solution continues to stir for two minutes after borohydride addition and then the stir bar was magnetically suspended above the solution.[a] During this time, the solution turned from pale pink to brown or grey[b,c], indicating the formation of $Co_xB_y$ NPs. X-ray photoelectron spectroscopy (XPS) was used to measure the CoNP scaffold and compare it to cobalt ions from common cobalt compounds. As seen in FIG. 1 (panel A), the CoNP spectrum cannot be explained by that of elemental cobalt (cobalt foil).

In fact, as seen in FIG. 1 (panel B), a linear combination of ~70% cobalt boride compound (a commercially available mixture of $Co_2B$ and $Co_3B$) and 30% $CoCl_2$ precursor produces a fit that is in better agreement with the data.

The resultant $Co_xB_y$ NP solution sat under nitrogen protection for 1 hour (allowing all $H_2$ to evolve) until being used in galvanic exchange (Step 3).

[a] A previous publication by Schwartzberg et al. (2007) *J. Phys. Chem. C* 111(44): 16080-16082 reported that magnetic stirring leads to formation of gold nanotubes due to alignment of the cobalt scaffold particles. This alignment does not occur in the synthesis reported herein. The difference in these results may be due to suspension of the stir bar after two minutes of $Co_xB_y$ NP formation. In this case, the stir bar helps with homogeneous mixing of starting reagents and reducing agent (thereby lowering resultant $Co_xB_y$ NP polydispersity) but is not left in solution long enough to cause chain formation of $Co_xB_y$ NPs.

[b] The color of the $Co_xB_y$ NP solution can be used as a general indicator of $Co_xB_y$ NP size. A darker brown color indicates formation of relatively small $Co_xB_y$ NPs (<50 nm diameter) while a lighter grey color indicates formation of relatively large $Co_xB_y$ NPs (>70 nm diameter). A brownish grey color indicates formation of mid-range $Co_xB_y$ particles (50-70 nm diameter). The exact $Co_xB_y$ NP size may be determined by extracting a small amount of solution (in an air-free manner via syringe) and using dynamic light scattering (DLS) to obtain the hydrodynamic diameter. This measurement should be taken immediately upon extracting the sample as the $Co_xB_y$ NPs are air-sensitive and will begin to oxidize and decrease in diameter.

[c] The diameter of the $Co_xB_y$ NP scaffold may be controlled by controlling both the age and amount of sodium borohydride used in synthesis (less reactive sodium borohydride and smaller volumes of borohydride result in larger $Co_xB_y$ NP diameters).

(2) Gold Salt Preparation

Chlorauric acid ($HAuCl_4$) was diluted with water to the desired concentration and volume[d], stirred with a magnetic stir bar, and deaerated by bubbling with nitrogen gas[e] for one hour. Argon gas may also be used. After deaeration, the gas needle was suspended above the solution.

[d] Once the $Co_xB_y$ scaffold is made, the HGN shell thickness (and thus the aspect ratio and corresponding SPR) for any size can be tuned simply by adjusting the volume of gold used in Step 2. More gold will result in a thicker shell and blue-shifted SPR. Less gold will result in a thinner shell and red-shifted SPR.

[e] The improvement resulting from deaeration of the gold salt over previous approaches is depicted in FIG. 2 (panel A). In the previous approaches (1), the $Co_xB_y$ NP is oxidized by gold at the same time as it is being oxidized by atmospheric oxygen, which may reduce resultant HGN homogeneity and affect formation of the gold shell. These two reactions are separated in the synthesis reported herein (2); the galvanic exchange is allowed to occur before the system is exposed to oxygen. For this to be possible, the gold solution must also be deaerated and the two solutions must be introduced in the absence of oxygen.

(3) Galvanic Exchange

Once the $Co_xB_y$ NP scaffolds and gold salt were prepared, galvanic exchange was carried out. The $Co_xB_y$ NP solution was transferred to the stirring gold solution via air-free cannula transfer. Galvanic exchange occurred spontaneously due to the difference in reduction potential of the metals. The volume of $HAuCl_4$ controls the resultant gold shell thickness and associated SPR (more gold available for galvanic exchange results in a thicker HGN shell and blue-shifted SPR). The transfer flow rate may also affect the gold shell thickness and associated SPR (a slow transfer would effectively result in fewer cobalt particles available to participate in galvanic exchange). The $Co_xB_y$ NP+Au solution continued to stir for two minutes.

As shown in FIG. 2, panel B, deaeration of the gold red-shifts the resultant particles and produces a more even shell, all other things being equal. The non-deaerated version produces a blue-shifted and more patchy shell. Thus, it is apparent that oxygen is a factor in shell formation, and higher quality shells are produced when galvanic exchange is carried out in the absence of oxygen.

(4) $Co_xB_y$ Core Oxidation

Finally, oxygen may be introduced to the $Co_xB_y$ NP+Au solution by removing the septa and swirling the flask by hand or continuing to stir with a magnetic stir bar. An oxygen bubbler may also be used. The residual $Co_xB_y$ cores are fully oxidized by this exposure to oxygen, leaving behind solvent-filled gold shells. The way oxygen is introduced to the $Co_xB_y$ NP+Au solution can affect resultant SPR.[f]

[f] When oxygen is allowed to reach all parts of the solution evenly, the resultant SPR is red-shifted. When the solution-air interface is significantly reduced (for example, when the solution is hand-swirled), the resultant SPR is blue-shifted.

II. Size and SPR Control

HGN size is primarily dictated by the size of the $Co_xB_y$ scaffold—that is, larger $Co_xB_y$ templates will create larger HGNs. Described herein is a new method for size control in HGN synthesis that allows size selection without loss of monodispersity.

Figure 3:
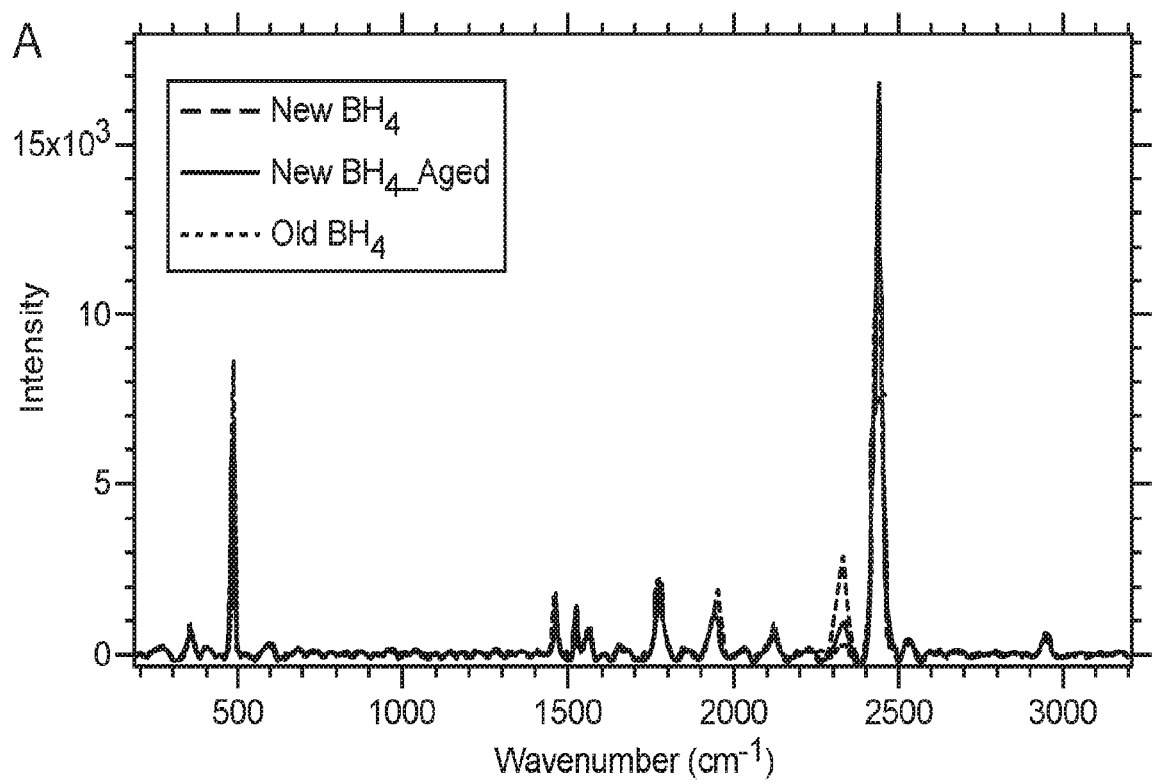
FIG. 3 Panel A: Raman spectroscopy of new, 1 hour aged, and old $NaBH_4$ showing a difference in the peak intensities at 2439 and 2340 $cm^{-1}$. Panel B: The general trend of increased 2439:2340 $cm^{-1}$ peak ratio resulting in increased HGN diameter.

In attempting to control the size and monodispersity of HGNs, the size and monodispersity of the cobalt scaffold should first be addressed. To this end, specific attention was paid to the borohydride reducing agent. $NaBH_4$ undergoes a chemical change as it ages, which the inventors determined to be most apparent in the ratio of the 2439 and 2340 $cm^{-1}$ Raman peaks associated with B—H stretching (FIG. 3, panel A). As this ratio grows larger, larger HGNs are accessible through synthesis, all other things being equal. This general trend is tabulated in FIG. 3, panel B. Fresh $BH_4$ was aged by exposure to air while stirring for one hour.

The reason for the trend shown in FIG. 3 lies in a change in reduction potential. Fresh borohydride is potent. It will reduce the aqueous cobalt ions quickly, creating many cobalt nucleation centers. This results in a larger number of small nanoparticles. As borohydride ages, it reacts with moisture in the air, becoming effectively less potent. Aged borohydride will reduce the cobalt more slowly, creating fewer nucleation centers. This results in a smaller number of larger nanoparticles.

After confirming that the age of borohydride (and thus the reactivity of borohydride) affects the size of the $Co_xB_y$ NP scaffold (and ultimately the resultant HGNs), new $BH_4$ was reacted with water for a given amount of time to mimic the aging process. Indeed, the aged $BH_4$ generated larger particles than the fresh $BH_4$. Different ratios of fresh and aged $BH_4$ affected both resultant $Co_xB_y$ NP size and polydispersity, as confirmed with dynamic light scattering (DLS) measurements shown in FIG. 4. A similar study addresses size control of silver nanoparticles made from reduction of $AgClO_4$ with $NaBH_4$.

As the percentage of aged borohydride increases, the size of the $Co_xB_y$ scaffold also increases. With too much aged borohydride, the scaffolds are very large, but very polydisperse (as seen in the 10/90 ratio example). This method has been expanded upon by making fine adjustments to both the total volume of sodium borohydride and also the ratio of fresh:aged and shown that a wide range of $Co_xB_y$ NP scaffold sizes can be created with a high degree of monodispersity. The DLS in FIG. 5 are provided as examples, showing synthesis of $Co_xB_y$ NP scaffolds from less than 20 nm to greater than 80 nm in small increments with high monodispersity for each size. An example protocol is presented below.

Size Control Synthesis Protocol

Store borohydride in an oxygen and moisture free environment.

Step 1. Prepare 1M $BH_4$ 48 hours before use. This will serve as the aged solution.

Step 2. Prepare cobalt precursor as described in Section I of this Example.

Step 3. Prepare 1M fresh $BH_4$ as needed. Mix desired fresh:aged $BH_4$ ratio immediately before injection into cobalt solution.

Step 4. Continue HGN synthesis as previously described.

This method allows selection of a desired $Co_xB_y$ NP scaffold size. The desired shell thickness (and resultant SPR) may be obtained by simply controlling the amount of gold added for galvanic exchange. Because this method allows you to select both the diameter and the shell thickness, the SPR can be tuned across the visible and into the NIR for any size HGN. For instance, FIG. 6 shows 30 nm, 45 nm, and 70 nm HGNs produced with this method with shell thickness selected for 800 nm SPR. The high monodispersity is evident.

Having control over both the outer diameter and SPR is important. Even small changes in size can have a dramatic effect on the photophysical properties of these nanostructures. For instance, the inventors' heat generation studies have shown that 50 nm HGNs with 800 nm SPR generate more than two times the amount of heat per µg of gold than 70 nm HGNs with 800 nm SPR.

Example 2—$Co_xB_y$ Nanoparticle Size Control and Galvanic Exchange for the Formation of Highly Tunable Hollow Metal Nanospheres Introduction To gain independent control over both the diameter and SPR of hollow gold nanospheres (HGNs), the work reported herein is twofold. First, the formation of $Co_xB_y$ nanoparticle ($Co_xB_y$ NP) scaffolds made from sodium borohydride reduction of aqueous cobalt chloride was investigated. In pursuit of size control, $B(OH)_4^-$ (the final product of $BH_4^-$ hydrolysis) was introduced as a growth agent, capable of slowing nucleation of cobalt ions and inducing coalescence, thereby increasing the final size of the particles. Using this new approach, the synthesis of highly monodisperse scaffolds with incremental increase in diameter over a ~17-85 nm hydrodynamic diameter range was demonstrated. This is believed to be the first demonstration of fine control of $Co_xB_y$ NP diameter over a large size range while maintaining monodispersity. Second, the role of environmental oxygen in the galvanic exchange process was investigated and parameters identified for the formation of uniform gold shells. Finally, combining insight from all results, a well-controlled synthesis of HGNs, from cobalt scaffold formation to galvanic exchange and subsequent core oxidation is demonstrated, enabling high quality, monodisperse HGNs over a range of diameter and SPR combinations.

Shown in the present example is that by varying the relative amounts of $BH_4^-$ reducing agent and $B(OH)_4^-$ growth agent, high quality $Co_xB_y$ NPs ranging from ~17-85 nm in hydrodynamic diameter may be prepared, all with relative standard deviation (RSD)<3%. When converting a cobalt-based scaffold to an HGN, oxygen must be regarded as a reactant. To that end, the quality of the resultant shell may be controlled not only by size and shape of the starting scaffold or amount of metal provided for galvanic exchange, but also by controlled oxygenation. This finding provides important considerations for preparing HGNs of various SPRs and is applicable to other structures made from analogous galvanic replacement reactions with easily oxidized starting materials. Finally, with this level of synthetic control, high quality HGNs over a range of desired size and SPR combinations can be realized, an achievement critical to many applications that require specific particle size or SPR wavelength.

This achievement has broad implication for the growing field of conversion chemistry, and more specifically for hollow metal nanoparticle synthesis utilizing galvanic exchange with cobalt or other air-sensitive materials.

Materials and Methods

Synthesis of $Co_xB_y$ NP Scaffolds

Cobalt(II) chloride hexahydrate ($CoCl_2 \cdot 6H_2O$) was purchased from Sigma-Aldrich, trisodium citrate dihydrate ($Na_3C_6H_5O_7 \cdot 2H_2O$) was purchased from VWR International, and sodium borohydride ($NaBH_4$) was purchased from Fisher Scientific. All water used in synthesis was ultrapure in quality, with a resistivity of 18.3 MO.

$Co_xB_y$ NP scaffolds were synthesized via the well-established reduction of $Co^{2+}$ ions with $NaBH_4$, using citrate as a capping ligand. Briefly, a 100 mL solution of 0.40 mM $CoCl_2 \cdot 6H_2O$ and 4.0 mM $Na_3C_6H_5O_7$ was prepared in a 500 mL round bottom flask and deaerated by bubbling with nitrogen for 1 hour. During this time, the solution was stirred at 700 RPM with a magnetic stir bar. Then, a given volume of freshly prepared aqueous 1 M $NaBH_4$ (25-200 µL) was injected while the solution continued to stir under nitrogen protection. After addition of $NaBH_4$, the solution turned from pale pink to brown, indicating the reduction of $Co^{2+}$ ions and the formation of the $Co_xB_y$ NP scaffold. After 2 minutes, the stir bar was magnetically suspended above the solution and the $Co_xB_y$ NPs were subsequently allowed to stand under constant nitrogen flow for 2 hours to ensure complete hydrolysis of the borohydride reducing agent.

Control of the $Co_xB_y$ NP Diameter

To synthesize larger $Co_xB_y$ NPs, a given volume of $B(OH)_4^-$ (20-200 µL) was added to the freshly prepared aqueous 1 M $NaBH_4$ and quickly mixed before injection into the cobalt salt solutions. The presence of $B(OH)_4^-$ prolonged the onset of color change from pale pink to brown/grey. To obtain $B(OH)_4^-$, a 1.0 mL aliquot of aqueous 1.0 M $NaBH_4$ was prepared and allowed to hydrolyze in ambient conditions for 48 hr.

Co K-Edge XANES

The Co K-edge XANES spectra were collected at the Stanford Synchrotron Radiation Lightsource (SSRL) on beamline 7-3 with an average current of 300 mA at an electron energy of 3.0 GeV. The radiation was monochromatized using a Si (220) double crystal monochromator, which was detuned to 50% of its maximum at the Co K-edge. The intensity of the incident X-rays ($I_0$) was monitored by a $N_2$-filled ion chamber in front of the sample. The monochromator energy was calibrated by using the first peak maximum of the first derivative of the Co foil spectrum (7,709.5 eV). The solution based samples were collected using a sealed glass cell with a silicon nitride window covering a hole in the glass cell through which the X-rays were incident into the solution. The sample was placed in a $N_2$-purged box fitted with kapton tape windows. The sample fluorescence signal was recorded using a 30-element Ge detector (Canberra) with the samples at 45° to the incident beam. Co K-edge data were collected for solutions of 0.4 M $CoCl_2$, 0.4 M $CoCl_2$+0.8 M $NaBH_4$. A powdered reference sample of commercially available $Co(OH)_2$ was collect without further purification by dilution in boron nitride (~1% w/w) and then packed into 0.5 mm-thick aluminum sample holders using kapton film windows on both sides. Data reduction of the XAS spectra was performed using SamView (SixPack software, Samuel M. Webb, SSRL). Athena software (IFEFFIT package) was used to subtract the pre-edge and post-edge contributions, and the results were normalized with respect to the edge jump.

XPS Spectroscopy

XPS was performed using a monochromatized Al Kα source (hv=1486.6 eV), operated at 225 W, on a Kratos Axis Ultra DLD system at a takeoff angle of 0° relative to the surface normal, and pass energy for narrow scan core level and valence band spectra of 20 eV. A tungsten filament charge neutralizer was utilized for the powered samples. Spectral fitting was done using Casa XPS analysis software. Spectral positions were corrected using adventitious carbon by shifting the C 1s core level position to 284.8 eV and curves were fit with quasi-Voigt lines following Shirley background subtraction. The samples were prepared in a nitrogen glove box.

UV-Vis Spectroscopy

UV-Vis spectra were recorded with an Agilent Technologies Cary 60 UV-Vis spectrophotometer using a 700 μL quartz cuvette with standard 10 mm optical path length. For measurement, 500 μL aliquots were extracted from the solutions under nitrogen protection and immediately transferred to the spectrophotometer.

Dynamic Light Scattering (DLS)

DLS was performed on a Dyna Pro NanoStar from Wyatt Technology using Dynamics software version 7.1.7. Data acquisition parameters were set to water solvent, spherical radius of gyration (Rg) model, temperature of 20.000 C, and 30 acquisitions. The reported ±values represent one standard deviation from the mean. Relative standard deviation (RSD) represents one standard deviation as a percentage of the mean, using unrounded values for calculation. For measurement, 200 μL aliquots were extracted from the solutions under nitrogen protection and immediately transferred to the DLS instrument.

Cyclic Voltammetry

Cyclic voltammograms (CVs) of $NaBH_4$ were taken on a Pine potentiostat (Model AFCBP1) using an Au wire working electrode, a Pt coil counter electrode, and an Hg/HgO (1.0 M KOH) reference electrode. To hydrolyze the sample, 1.0 mL of 1.0 M aqueous $NaBH_4$ was prepared and left sitting in ambient conditions. At each timepoint, a 100 μL aliquot was transferred to 9.90 mL of 0.10 M KOH to suppress continued hydrolysis during measurement. CVs were taken at three timepoints (0 hr, 24 hr, and 48 hr) and a 2.500 V/s sweep rate.

$^{11}$B NMR

Proton-coupled $^{11}$B NMR was performed on a Bruker 500 MHz NMR using 5 mm thin wall Quartz NMR tubes (Wilmad, 528-PP-7QTZ) to eliminate extraneous boron signal. At each timepoint, an 80 μL aliquot of the 1.0 M aqueous $NaBH_4$ was transferred to 720 μL of 0.10 M KOH to create a 0.10 M $NaBH_4$ solution. A 720 μL aliquot of this solution was added to 80 μL $D_2O$ to make a final 10% v/v deuterated solution for frequency locking.

Synthesis of Hollow Gold Nanospheres

Chloroauric acid ($HAuCl_4$) was purchased from Fisher Scientific. All water used in synthesis was ultrapure in quality, with a resistivity of 18.3 MΩ. For anaerobic galvanic exchange, a given volume (1.00-10.0 μL) of 0.10 M $HAuCl_4$ was added to 15 mL ultrapure water and deaerated by bubbling with nitrogen gas for one hour under magnetic stirring at 700 RPM. Once deaerated, galvanic exchange was initiated by transferring 15 mL of the $Co_xB_y$ NP solution to the stirring gold solution via air-free cannula transfer. The resultant core/shell Co NP/Au particles were stirred for two minutes under nitrogen protection at 700 rpm before final oxidation of the remaining $Co_xB_y$ NP cores. The residual cobalt cores were fully oxidized either by removing the septa and stirring at 700 rpm for three minutes under ambient conditions or transferring a 3.0 mL aliquot to a vial and vortexing for 10 seconds. For aerobic GE, a given volume (1.00-10.0 μL) of 0.10 M $HAuCl_4$ was added to 15 mL ultrapure water and stirred for 60 min (for consistency with the anaerobic protocol) in ambient conditions. GE was initiated by transferring 15 mL of the $Co_xB_y$ NP solution to the stirring gold solution via cannula transfer in air. The resultant $Co_xB_y$ NP/Au core/shell particles were stirred for five minutes at 700 rpm under ambient conditions to ensure complete oxidation of the residual $Co_xB_y$ NP cores.

Electron Microscopy

SEM was performed at the W.M. Keck Center for Optofluidics at the University of California Santa Cruz on an FEI Quanta 3D field emission microscope operated at 5.00 kV acceleration voltage. Since the Co NP scaffolds are air-sensitive, great care was taken in preparing them for SEM. The as-formed Co NP scaffolds, synthesized under nitrogen protection, were transferred into an air-free glove box where they were centrifuged at 5,000 RPM for 15 minutes. After removing the supernatant, the concentrated solution was dropped onto a hexagonal, 400 mesh copper grid with carbon support film of standard 5-6 nm thickness (Electron Microscopy Sciences, CF400H-Cu-50) and allowed to dry in the glove box under vacuum and nitrogen protection. When dry, the grid was immediately transferred to the microscope. HGN solutions were centrifuged twice in ambient conditions at 13,000 RPM for 2 minutes and resuspended in ultrapure water. HRTEM was performed at the National Center for Electron Microscopy (NCEM) at the Lawrence Berkeley National Laboratory Molecular Foundry on an FEI UT Tecnai microscope operated at 200 kV acceleration voltage. Diameter measurements were taken directly from HRTEM images using ImageJ software. For each sample, at least 50 HGNs were used to calculate the average diameter±one standard deviation. Additionally, 12 shell thickness measurements were taken for each HGN measured. Individual HGNs were matched with their associated shell thickness measurements to determine aspect ratio.

Results

Optical and Structural Characterization of $Co_xB_y$ NP Scaffolds Made with $BH_4$ Reducing Agent $Co_xB_y$ NPs were synthesized through the well-established reaction between aqueous cobalt chloride and sodium borohydride in the presence of a citrate capping ligand.[29,39] Although the NPs produced by this method have often been described as elemental cobalt, various cobalt borides have been experimentally identified as the main products.[47-49] In agreement with these reports, in-situ X-ray absorption spectroscopy (XAS) collected at the Co K-edge before and after the addition of borohydride confirm that $Co^0$ is not produced. X-ray photoelectron spectroscopy (XPS) collected on the isolated brown cobalt-based product confirms the lack of metallic character. Taken together, these results are in better agreement with what has been reported in the literature for $Co_2B$, as detailed in Supporting Information Discussion S1. A commonly accepted reaction mechanism with $Co_2B$ as the final product is shown in Equation 1.[47]

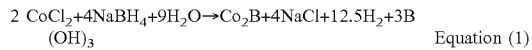

$$2\ CoCl_2 + 4NaBH_4 + 9H_2O \rightarrow Co_2B + 4NaCl + 12.5H_2 + 3B(OH)_3 \quad \text{Equation (1)}$$

To control the size of nanoparticles, an understanding of their nucleation and growth processes is essential. In classical nucleation theory as set forth by LaMer in the 1950s, particle diameter is said to be governed by the extent of initial nucleation.[50,51] To investigate the effect of initial nucleation on final $Co_xB_y$ NP diameter, syntheses were carried out with $BH_4^-:Co^{2+}$ molar ratios ranging from 0 to 5.00. According to Equation 1, two moles of $BH_4^-$ are needed to reduce every one mole of $Co^{2+}$, so only $BH_4^-:Co^{2+}$ mole ratios greater than 2.00 will provide $BH_4^-$ in excess of what is required for full reduction of cobalt ions.

The resultant scaffolds were monitored by their extinction spectra, as shown in FIG. 8, Panel A. In absence of reducing agent, the extinction spectrum consisted only of a large signal at ultraviolet (UV) wavelengths due to citrate and a small peak ~500 nm due to the $^4T_{1g}(f) \rightarrow ^4T_{1g}(p)$ d electron transition of hydrated $Co^{2+}$ ions (red curve).[52] When reducing agent was provided, the cobalt solution turned from pale pink to brown and the extinction spectrum gained low signal throughout the visible range, indicating formation of $Co_xB_y$ NPs (Scaffold 2-5). The increasing extent of nucleation with increasing $BH_4^-:Co^{2+}$ mole ratio is apparent by the gradual increase of the Co-related extinction. Saturation is observed between 1.25 and 2.50 $BH_4^-:Co^{2+}$, consistent with Equation 1. Resultant hydrodynamic diameters were then assessed with dynamic light scattering (DLS), as tabulated in Table 1. Importantly, the hydrodynamic diameters of all $Co_xB_y$ NPs agree to within one standard deviation. Because the reaction between $BH_4^-$ and $CoCl_2$ is fast, nucleation occurs rapidly but growth cannot proceed due to the lack of additional reactant after the initial injection. Thus, simply increasing or decreasing the amount of sodium borohydride may affect extent of nucleation, but is not enough to appreciably control the resultant nanoparticle size for this system.

TABLE 1

Synthetic parameters and resultant hydrodynamic diameter (mean ± one standard deviation) for $Co_xB_y$ NP scaffolds.

| Scaffold | $BH_4^-:Co^{2+}$ | $B(OH)_4^-:BH_4^-$ | Hydrodynamic Diameter (nm) |
|---|---|---|---|
| 1 | 0 | 0 | NA |
| 2 | 0.625 | 0 | 19 ± 3 |
| 3 | 1.25 | 0 | 21 ± 2 |
| 4 | 2.50 | 0 | 19 ± 2 |
| 5 | 5.00 | 0 | 23 ± 3 |
| 6 | 5.00 | 0.500 | 43 ± 2 |
| 7 | 5.00 | 1.00 | 56 ± 1 |
| 8 | 2.50 | 1.00 | 61 ± 1 |
| 9 | 2.50 | 2.00 | 76 ± 2 |

Many recent studies into the formation mechanism of colloidal metal NPs from wet chemical reduction of metal salt precursors have reported mechanisms that deviate from classical nucleation theory.[53-59] For instance, for the reduction of $HAuCl_4$ with $NaBH_4$, a two-step mechanism has been described: metal ions are swiftly reduced to small clusters that then rapidly coalesce to form the final particles. A similar mechanism was reported for the reduction of $AgClO_4$ with $NaBH_4$ and it was found that clusters aggregate and coalesce until reaching a size at which there is sufficient stability to halt the process. In both reports, the extent of aggregation and coalescence, as opposed to the extent of initial nucleation, was determined to be the controlling factor in final nanoparticle size. Interestingly, in the case of $AgClO_4$ reduction, the onset of aggregation and coalescence was shown to arise from a destabilization of colloidal stability correlated to the hydrolysis of excess $BH_4^-$ to $B(OH)_4^-$. In contrast, for our cobalt system, the conversion of residual $BH_4^-$ to $B(OH)_4^-$ does not promote additional coalescence; the resultant scaffold size is the same whether $BH_4^-$ is in excess or not. However, the presence of $B(OH)_4^-$ during initial nucleation may indeed affect the formation of Co NPs. It has been recently shown that decomposition of sodium borohydride during storage leads to significant changes in the resulting $Co_xB_y$ particles.[60] As $B(OH)_4^-$ is the final decomposition product, its role in $Co_xB_y$ formation and its effect on the final particle diameter was investigated.

Optical and Structural Characterization of $Co_xB_y$ NP Scaffolds Made with $B(OH)_4^-$ Growth Agent To investigate the potential effect of $B(OH)_4^-$ on $Co_xB_y$ NP formation, syntheses were repeated with $B(OH)_4^-$ provided alongside the $BH_4^-$ reducing agent. To obtain $B(OH)_4^-$, aqueous 1.0 M $NaBH_4$ was hydrolyzed for 48 hr. The product was characterized and identified with proton-coupled $^{11}B$ NMR and cyclic voltammetry, as detailed in Supporting Information Discussion S2. Table 1 displays DLS results for $Co_xB_y$ NPs made with $B(OH)_4^-:BH_4^-$ molar ratios of 0.500 and 1.00 and a molar excess of $BH_4^-$ (Scaffolds 6-9). In all cases, the addition of $B(OH)_4^-$ during initial nucleation of cobalt ions resulted in an increase in scaffold diameter. In fact, the resultant scaffold is largest for large $B(OH)_4:BH_4^-$ ratios and small $BH_4^-:Co^{2+}$ ratios (Scaffold 9). Importantly, the extinction spectrum can be used as an indicator of scaffold size. The extinction spectra for ~20 nm scaffolds followed normal exponential decay (FIG. 8, Panel A), but an inflection ~240 nm was apparent in the extinction spectrum for the 43±2 nm scaffold (FIG. 8, Panel B, Scaffold 6). For larger sizes, the inflection grew into a small extinction feature that broadened and red shifted with increasing diameter (FIG. 8, Panel B, Scaffolds 7-9). This is the first experimental evidence of a size-dependent extinction feature in $Co_xB_y$ NPs.

Elucidating the Role of $B(OH)_4^-$ in the Co NP Growth Mechanism

To better understand the role of $B(OH)_4^-$ as a growth agent, $Co_xB_y$ NP formation was investigated by time-resolved UV-Vis for Scaffolds 5 and 7. These scaffolds had equivalent amount of $BH_4^-$ (5.00 $BH_4^-:Co^{2+}$) but varying amounts of $B(OH)_4^-$ (0 and 1.00 $B(OH)_4^-:BH_4^-$, respectively). Three dimensional extinction spectra are displayed in FIG. 9, Panels A and C for the first 20 minutes of scaffold formation. In these figures, the spectral contribution of citrate has been subtracted to better highlight the appearance of features below 300 nm.

The growth processes are visibly different with and without addition of $B(OH)_4^-$. When no $B(OH)_4^-$ was added during nucleation, the absorption related to $Co_xB_y$ formation formed in less than 1 minute and remained unchanged for the length of the observation (FIG. 9, Panel A, Scaffold 5: 23±3 nm). No appreciable broadening of this signal occurred, suggesting the reaction was complete within the first minute. When the same synthesis was performed with a $B(OH)_4^-:BH_4^-$ ratio of 1.00, the scaffold formation was significantly delayed (FIG. 9, Panel C, Scaffold 7: 56±1 nm).

Instead, almost immediately, a small absorption edge appeared at 220 nm and remained stable until minute 4. This edge then broadened and increased in intensity through minute 8 after which time the spectrum remained relatively unchanged for the remainder of the observation.

A similar intermediate 220 nm feature was previously reported in the formation of silver nanoparticles and was hypothesized as arising from the association of borohydride with the surface of primary monomers. However, in the present system, the edge near 220 nm cannot be due to borohydride. Instead, it was identified as being related to an interaction between $B(OH)_4^-$ and hydrated $Co^{2+}$ ions. In a separate experiment, when $B(OH)_4^-$ and $Co^{2+}$ ions were combined in the presence of citrate, the hydrated $Co^{2+}$ feature red-shifted from ~500 to 520 nm and the UV absorption of $B(OH)_4^-$ also red-shifted, increasing the signal around 220 nm. Extinction spectra and further discussion are provided in Supporting Information Discussion S3. Importantly, this data suggests a complex between $B(OH)_4^-$ and $Co^{2+}$ ions with citrate are formed in solution. The formation of this complex can be used to explain the growth process of larger $Co_xB_y$ NPs.

To better understand the growth process and the significance of the 220 nm signal, three wavelengths of interest are monitored over time in FIG. 9 Panels B and D: 500 nm to probe the disappearance of hydrated $Co^{2+}$ ions, 230 nm to probe the appearance of the $Co_xB_y$ NP scaffold, and 220 nm to probe the proposed $Co^{2+}+B(OH)_4^-$ complex. The 220 and 230 nm spectral contributions were deconvolved with singular-value decomposition (SVD), as detailed in Supporting Information Discussion S3. In the case of Scaffold 5, when no $B(OH)_4^-$ is present, FIG. 9 Panel B confirms that the reaction between $BH_4^-$ and $CoCl_2$ is rapid; hydrated $Co^{2+}$ were no longer discernible in the spectrum within the first minute. In the case of Scaffold 7, the presence of $B(OH)_4^-$ hindered the borohydride from reacting with cobalt ions as quickly and spectral contribution from hydrated $Co^{2+}$ was still clearly visible until minute 6. When the $Co_xB_y$ NP scaffold did begin to form, it did so at a slower rate, requiring almost 4 minutes for full growth. For both scaffolds, spectral contribution from the $Co_xB_y$ NPs began to appear only when the cobalt ions began to be consumed. SVD results also support the classification of the 220 nm edge as arising from interaction between $Co^{2+}$ and $B(OH)_4^-$ as its appearance is strongly correlated with the presence of hydrated $Co^{2+}$ and its depletion with the appearance of the $Co_xB_y$ scaffold.

In summary, the growth of $Co_xB_y$ NP scaffolds may be promoted by addition of $B(OH)_4^-$ alongside $BH_4^-$. While $B(OH)_4^-$ is not a reducing agent, it does indeed affect the initial nucleation of cobalt ions, simply by slowing the process. When $B(OH)_4^-$ is present, a complex is formed with the hydrated cobalt ions which hinders the $BH_4^-$ from normal nucleation. In addition to slowing the initial reduction, $B(OH)_4^-$ aids particle growth, likely through destabilization of primary clusters and promotion of coalescence processes. It has been well-established that $BH_4^-$ serves as a stabilizing agent for nanoparticles through electrostatic adsorption onto the particle surface.[44-46] If $BH_4^-$ access is hindered, the stabilization of as-formed clusters could also be hindered. The less-stable clusters are more likely to aggregate and coalesce, resulting in the formation of larger particles. While beyond the remit of this primarily synthetic investigation, further studies are needed to add insight to the $Co_xB_y$ NP growth mechanism, particularly to separate growth by coalescence of as-formed clusters from growth by additional reduction of ions in the electronical double layer.

Figure 10:
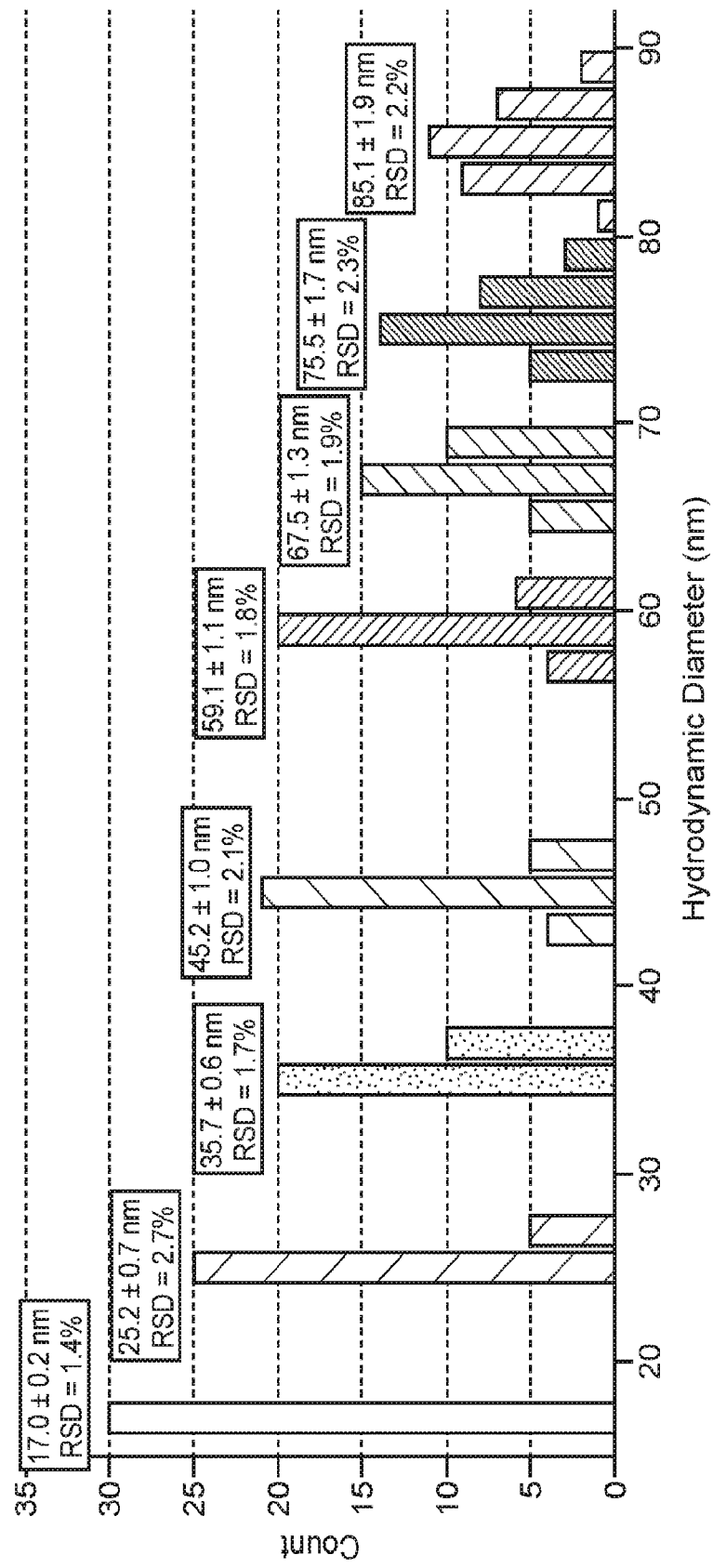
FIG. 10 Fine control of $Co_xB_y$ NP diameter over a large size range achieved with different $BH_4^-$:$B(OH)_4^-$ nucleation agent:growth agent ratios. Generally, smaller $BH_4^-$:$Co^{2+}$ ratios and larger $B(OH)_4^-$:$BH_4^-$ ratios produce larger $Co_xB_y$ diameters. Here, the $B(OH)_4^-$:$BH_4^-$ ratio ranges from 0 (red histogram) to 4 (neon green histogram) while the $BH_4^-$:$Co^{2+}$ ratio ranges from 5 to 1, respectively. Hydrodynamic diameter is reported with one standard deviation. RSD values are all under 3%, indicating high monodispersity of resultant scaffolds.

Demonstrating Fine Control of $Co_xB_y$ NP Diameter while Maintaining Monodispersity Shown here is that $B(OH)_4^-$ may be employed as a growth agent in the synthesis of $Co_xB_y$ NPs. As demonstrated in FIG. 10, high quality $Co_xB_y$ NPs ranging from ~17-85 nm in diameter may be prepared with this method, all with relative standard deviation (RSD)<3% and many with RSD<2%. In general, a greater $B(OH)_4^-$:$BH_4^-$ ratio results in larger $Co_xB_y$ NP diameters. However, this process is not without limit. There exists a threshold after which size can no longer be increased by increasing $B(OH)_4^-$ alone. At this point, larger sizes may be accessed by a reduction in $BH_4^-$. In this way, resultant $Co_xB_y$ NP size represents a delicate interplay between extent of nucleation and amount of growth agent. In FIG. 10, the $B(OH)_4^-$:$BH_4^-$ ratio ranges from 0 (red histogram) to 4 (neon green histogram) while the $BH_4^-$:$Co^{2+}$ ratio ranges from 5 to 1, respectively.

Figure 11:
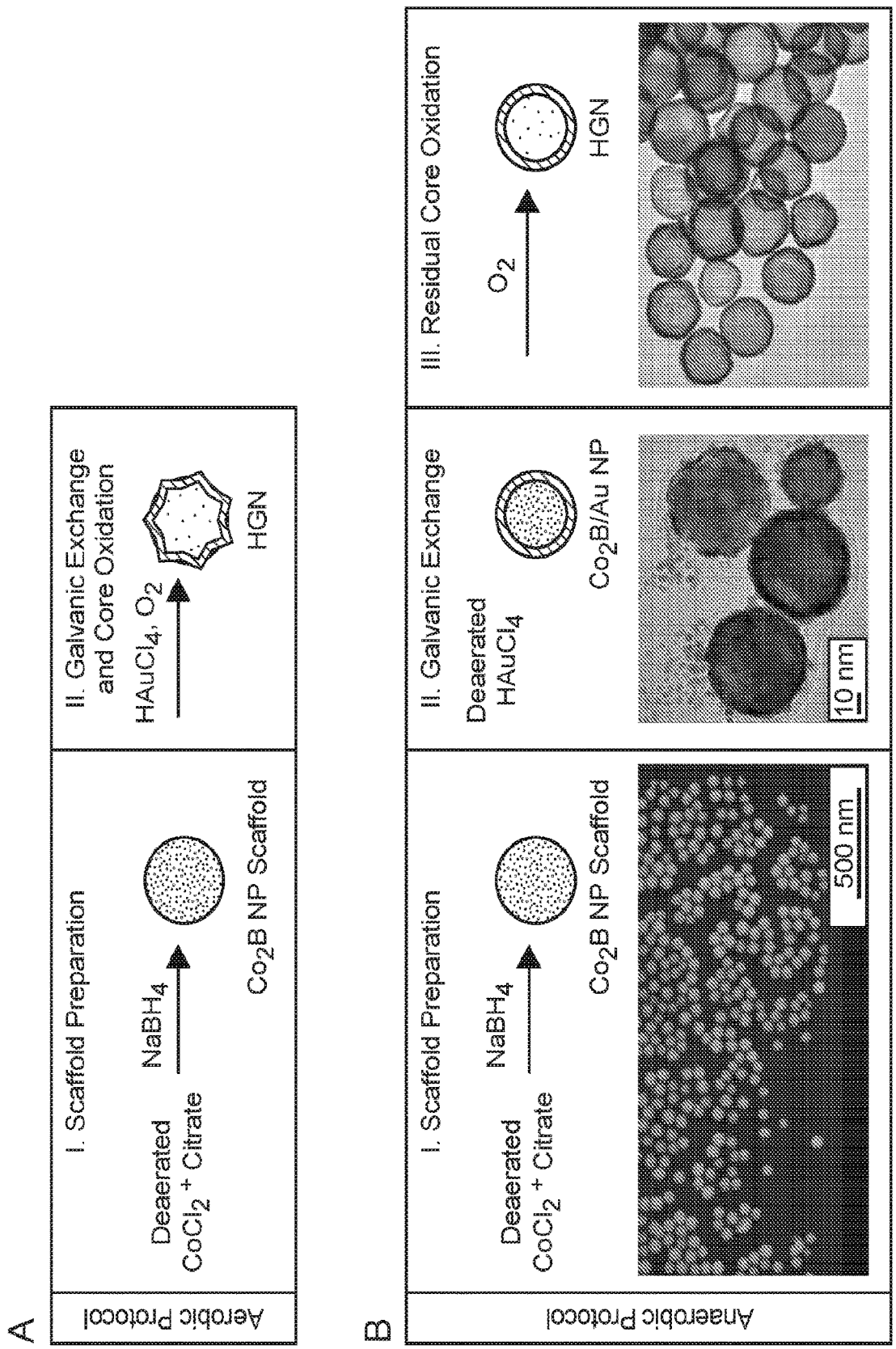
FIG. 11 Galvanic exchange protocols for HGN synthesis. Panel A: (Aerobic protocol) $Co_xB_y$ NP scaffolds are prepared by wet chemical reaction between cobalt ions and sodium borohydride, galvanic exchange is carried out by introduction of $Co_xB_y$ NP scaffolds to aqueous gold ions, and the $Co_xB_y$ NP core is simultaneously oxidized out of the shell by interaction with environmental oxygen. Panel B: (Anaerobic protocol) the galvanic exchange and oxygenation steps are separated and the gold salt deaerated so galvanic exchange may be carried out in absence of environmental oxygen. A representative SEM image is provided for the $Co_xB_y$ NPs formed in Step 1 and representative HRTEM images are provided for the $Co_xB_y$ NP/Au core/shell structures and resultant HGNs formed in Steps 2 and 3, respectively.

Synthesis of HGNs: Galvanic Exchange and Controlled Oxidation of $Co_xB_y$ NP Scaffolds When using $Co_xB_y$ NP scaffolds for the formation of HGNs, the present findings reveal that the shell structure may be dictated not only by the starting scaffold (to control the overall size and shape) and amount of metal provided for galvanic exchange (to control the shell thickness), but also by the extent of competing oxidation reactions due to the presence of environmental oxygen. To demonstrate this, two protocols for HGN synthesis are illustrated in FIG. 11. Both protocols involve the same steps: $Co_xB_y$ NPs are prepared as previously described, galvanic exchange is carried out between the $Co_xB_y$ NP scaffold and chloroauric acid, and the residual $Co_xB_y$ NP cores are oxidized into solution by exposure to environmental oxygen to leave behind solvent-filled shells of gold. However, the protocols differ in the timing of oxygen introduction. In the aerobic protocol, galvanic exchange and environmental oxygen exposure occur simultaneously. In the anaerobic protocol, these are separated into independent steps. In this way, a $Co_xB_y$/Au core/shell NP is allowed to form before interaction of $Co_xB_y$ with environmental oxygen. A scanning electron microscopy (SEM) image is provided for the $Co_xB_y$ NP scaffolds and a high-resolution transmission electron microscopy (HRTEM) image is provided for the $Co_xB_y$/Au core/shell NPs formed after galvanic exchange as well as the HGNs formed after oxidation of the residual $Co_xB_y$ cores.

Figure 12:
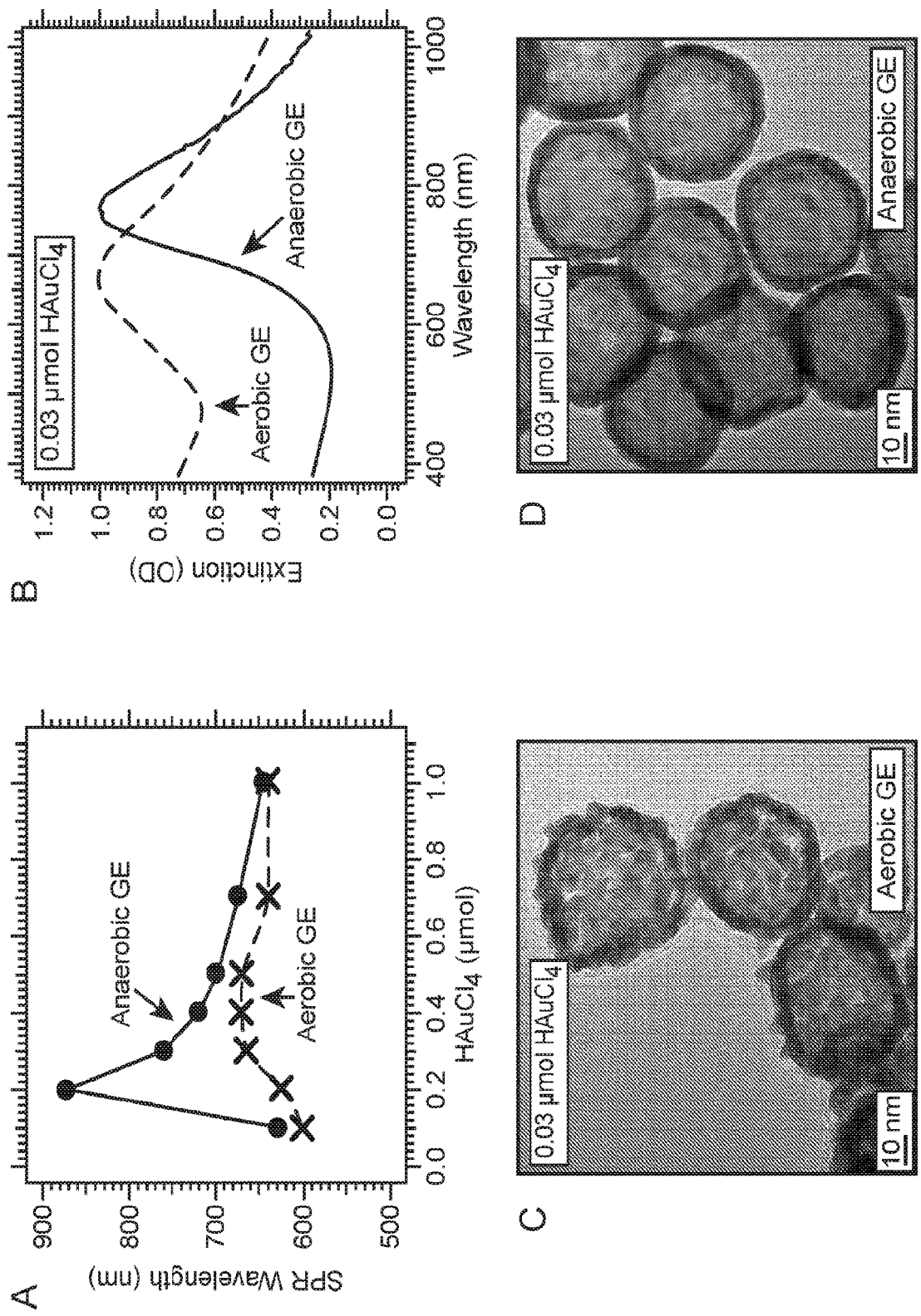
FIG. 12 Optical and structural effects of oxygen during galvanic exchange (GE) with Scaffold 7. Panel A: SPR peak wavelengths of HGNs made via aerobic (dashed line) and anaerobic (solid line) GE protocols using 0.10-1.0 μmol $HAuCl_4$. Panel B: Example extinction spectra for HGNs made with 0.30 μmol $HAuCl_4$ using aerobic (dashed line) and anaerobic (solid line) protocols. Panels C and D: Corresponding HRTEM images, scale bar 10 nm.

To assess the effect of environmental oxygen on shell formation, Scaffold 7 was taken through galvanic exchange with 0.10-1.0 μmol $HAuCl_4$ using aerobic and anaerobic protocols. The optical and structural properties of the resultant HGNs were characterized with UV-Vis and HRTEM, as shown in FIG. 12. In FIG. 12 Panel A, the wavelength of SPR maximum is plotted as a function of gold amount for each protocol. As expected, regardless of protocol, when less gold was provided for galvanic exchange, the SPR was red-shifted, due to the formation of thinner shells. However, for given amounts of $HAuCl_4$, the anaerobic protocol produced a redder SPR than the aerobic protocol. The extinction spectra for HGNs made with 0.30 μmol $HAuCl_4$ is provided as a representative example in FIG. 12 Panel B. When oxygen was present during galvanic exchange, the SPR was centered at 665 nm (dashed line). When galvanic exchange was instead carried out in absence of oxygen, the SPR was stronger and relatively red-shifted, centered at 760 nm (solid line). HRTEM reveals that these optical differences arise from structural ones. The aerobic shells are not continuous, but resemble a patchwork collection of smaller gold particle domains (FIG. 12 Panel C). The anaerobic shells, on the other hand, are smoother and more intact (FIG. 12 Panel D).

Extinction spectra and HRTEM images for HGNs made with the other amounts of $HAuCl_4$ are provided in Supporting Discussion, under "The Effect of Environmental Oxygen during Galvanic Exchange for the Formation of HGNs from $Co_xB_y$ NP Scaffolds."

Although the red-shift between protocols was observed for the majority of $HAuCl_4$ amounts investigated, it is not without limit. The SPR of HGNs for both protocols are in close agreement for the high and low $HAuCl_4$ amounts, which can also be explained from a structural standpoint. At high gold volumes, the anaerobic shell thickens and becomes more irregular, resembling the structure of the thick aerobic shell (e.g., the results for 1.0 μmol $HAuCl_4$ in FIG. 12 Panel A and FIG. 18 Panel F). On the other hand, if the volume of gold is too low, the shell begins to resemble a cage structure, with missing portions of the shell wall. When the gold volume is lowered even further, there is not sufficient material for the shell to retain structural integrity once the residual $Co_xB_y$ NP core is oxidized out. In this case, only large gold fragments remain and the SPR blue shifts to ~600 nm for both protocols (e.g., the results for 0.10 μmol $HAuCl_4$ in FIG. 12 Panel A).

Figure 19:
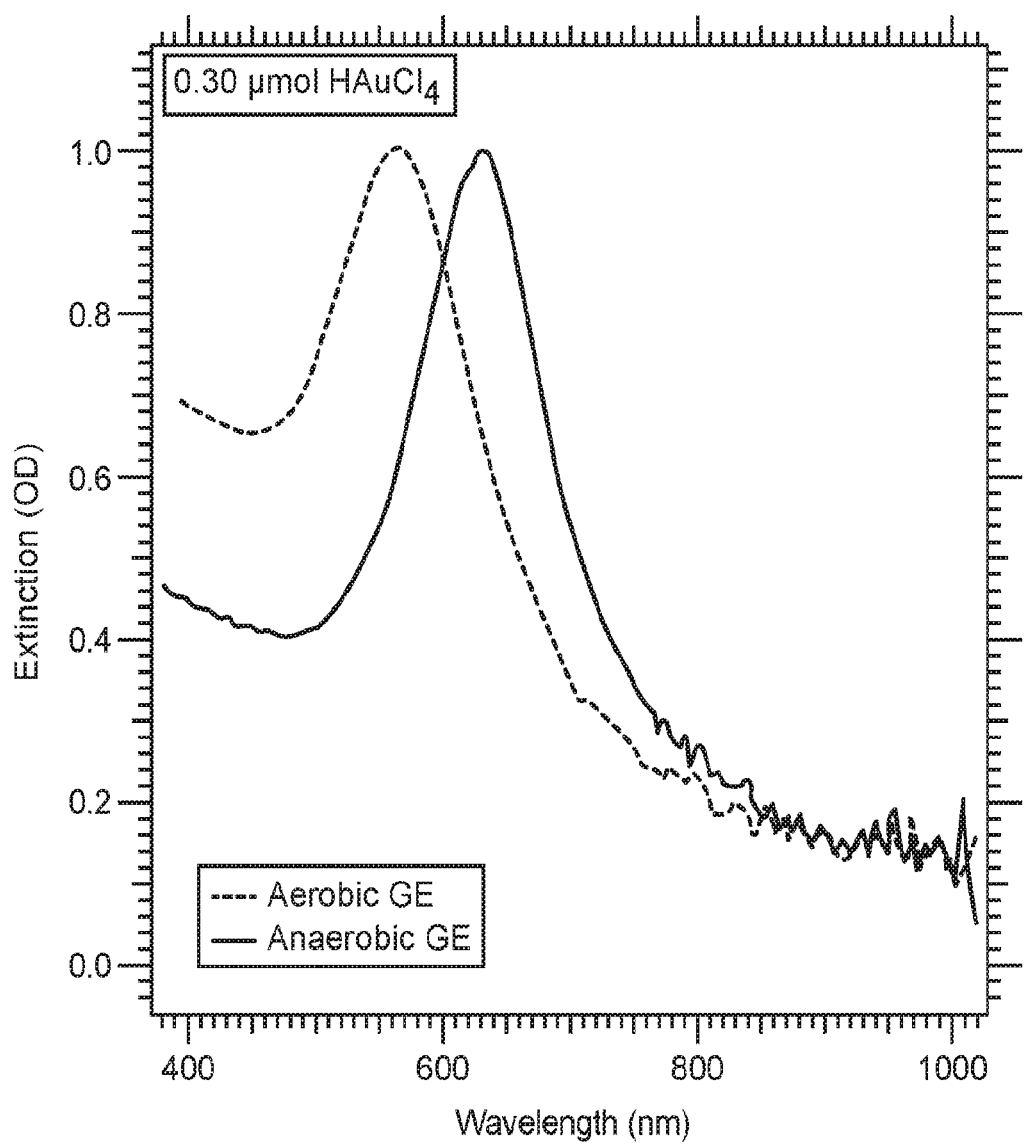
FIG. 19 Extinction spectra for HGNs made via galvanic exchange between $Co_xB_y$ Scaffold 5 (23±3 nm) and 0.30 μmol $HAuCl_4$. Results for aerobic (dashed line) and anaerobic (solid line) GE protocols are shown.
Figure 21:
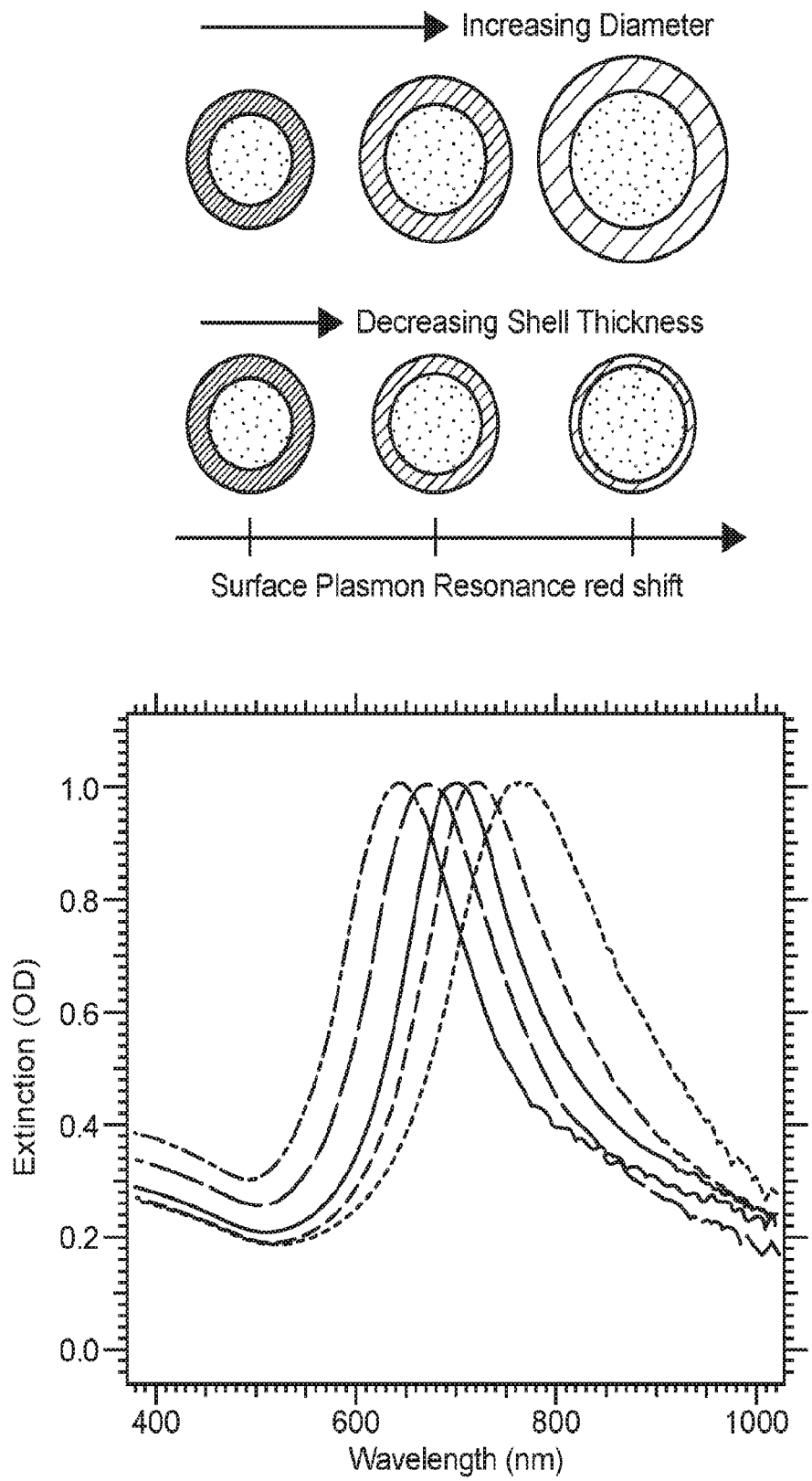
FIG. 21 Schematic illustration of the effects of HGN diameter and shell thickness on extinction spectrum.

Importantly, the anaerobic galvanic exchange was able to produce and stabilize relatively thinner shells before they lost structural integrity. The degree to which the SPR red-shifted as the amount of $HAuCl_4$ was decreased is much greater for the anaerobic galvanic exchange protocol overall. For instance, the anaerobic SPR shifted to 870 nm while the aerobic SPR was only able to reach 670 nm. Proposed herein is that because anaerobic galvanic exchange allows the scaffold to be protected while it exchanges with gold, no competition exists between gold and oxygen during shell formation and gold is therefore able to reduce onto the scaffold in a more uniform manner. The uniformity of plating enables thinner shells to form and be continuous enough to remain intact. This is especially advantageous for tuning the SPR of small HGNs to longer wavelengths, which has been a difficult task as red-shifting a small particle requires the formation of a very thin shell. The red-shift in SPR with anaerobic galvanic exchange is demonstrated for the smaller diameter Scaffold 5 in Supporting Information FIGS. 17 and 19.

Finally, the effect of oxygen was assessed during the final synthesis step of the anaerobic protocol, the residual $Co_xB_y$ NP core oxidation. Specifically, the rate of $Co_xB_y$ NP from the Co NP/Au structures was considered by varying the rate of oxygen addition. This work is discussed in Supporting Information Discussion S5 and the results suggest that the shell is still alterable even after galvanic exchange. In total, shown here is that a range of SPR frequencies, spanning upwards of 150 nm, may be accessed from the same starting $Co_xB_y$ NP scaffold and gold solutions through different routes of oxygen introduction. It is possible that larger shifts in SPR are obtainable with more finely controlled oxygenation during and after galvanic exchange.

Demonstrating Twofold Tunability: Independent Control of HGN Diameter and SPR

Figure 13:
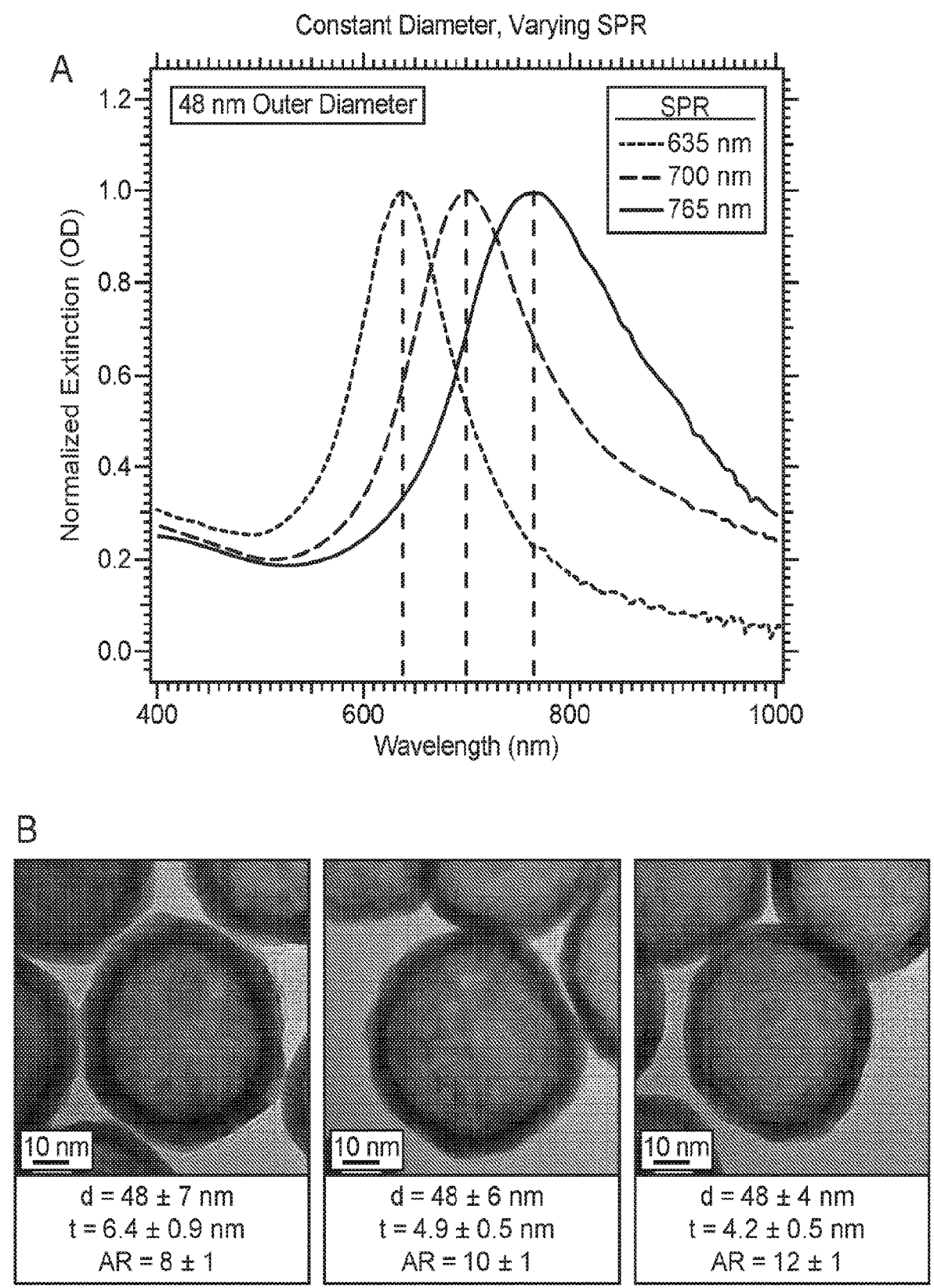
FIG. 13 Demonstration of two-fold tunability. Panel A: Normalized extinction for HGNs with the same outer diameter but different SPR: 48 nm HGNs with 635 nm, 700 nm, and 765 nm SPR. Panel B: Corresponding HRTEM images with average diameter (d), shell thickness (t), and aspect ratio (AR) as indicated, scale bar 10 nm. Panel C: Normalized extinction for HGNs with different outer diameter but the same SPR: 73±6 nm, 48±6 nm, and 37±4 nm HGNs with 700 nm SPR. After normalization, the 48±6 nm and 73±6 nm extinctions were offset on the y-axis by 0.25 and 0.50 OD, respectively. Panel D: Corresponding HRTEM images with average diameter, shell thickness, and aspect ratio as indicated, scale bar 10 nm.

With control of $Co_xB_y$ NP diameter and an understanding of how to achieve high quality, uniform shells, demonstrated herein is the twofold tunability of HGNs. As shown in FIG. 13 Panel A, by controlling both diameter and shell thickness, HGNs were synthesized with the same outer diameter with different SPRs. Conversely, as shown FIG. 13 Panel B, also synthesized were HGNs of different outer diameters with the same SPR by keeping the aspect ratio constant. This degree of tunability is unique to date and is especially advantageous for HGN use in applications that are sensitive to both size and SPR. Furthermore, the present approach provides opportunities to investigate fundamental size-dependence of photophysical and photocatalytic properties, such as those for plasmonic hot carriers, by enabling uniform energy distributions for a range of nanoparticle sizes.

Supplemental Information

The following information and data is supplemental to the preceding information and data of the present Example.

Identity of the $Co_xB_y$ NP Scaffold

Figure 14:
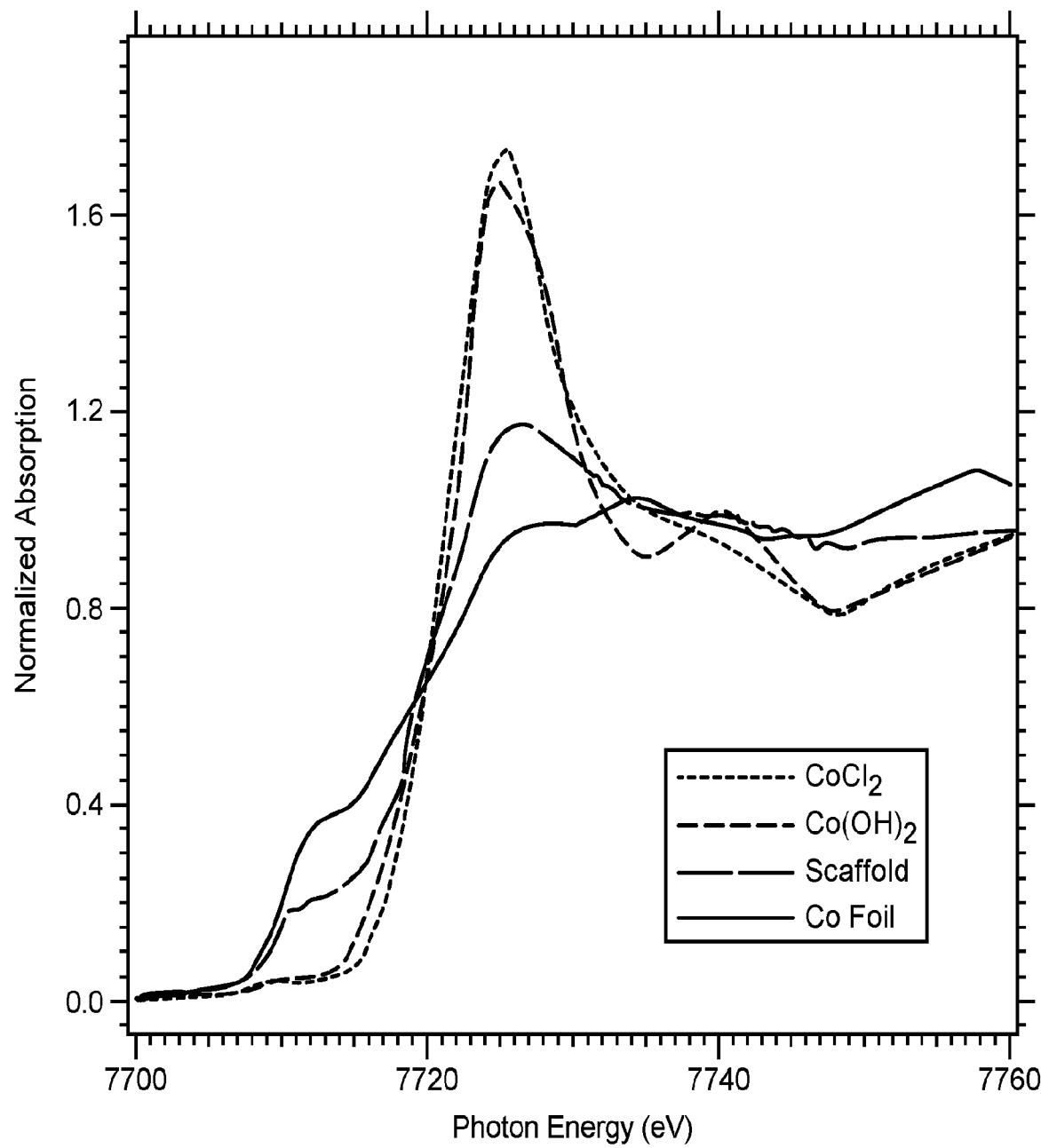
FIG. 14 Co 2p (Panel A) and B 1s (Panel B) XPS spectra of isolated scaffold product. Panel C: XANES spectra of as-synthesized scaffold solution (blue) as well as Co Foil (black), $Co(OH)_2$ (green), and $CoCl_2$ (red) references.

X-Ray photoelectron spectroscopy (XPS) and X-Ray absorption spectroscopy (XAS) were used to investigate the chemical composition of the cobalt-based nanoparticle (NP) scaffolds made from reacting $CoCl_2$ with $NaBH_4$ in the presence of a citrate capping ligand. The XPS Co 2p spectrum of the resultant product is shown in FIG. 14 Panel A. The binding energy of the Co $2p_{3/2}$ peak is slightly shifted from that of elemental cobalt (777.3 eV).[61] The Co $2p_{3/2}$ peak at 778.4 eV and the Co $2p_{1/2}$ peak at 793.4 eV are in good agreement with what has been previously observed for cobalt combined with boron (Co—B).[62,64] The remaining Co $2p_{3/2}$ and Co $2_{p1/2}$ peaks indicate the presence of a $Co^{2+}$ oxidation state.[63] This could mean that an oxide layer formed, potentially due to atmospheric exposure during sample transfer to the instrument. The B 1s spectrum (FIG. 14 Panel B) echoes these findings. The binding energy of 188.33 eV is slightly shifted from that of elemental boron (187 eV) and agrees with what has been previously reported for Co—B compounds.[62,63] The feature at 192.41 eV agrees with what has been previously reported for boron oxides.[62-64] For ease of reference, peak binding energies and comparison to previous reports are tabulated in Table 2. The results clearly demonstrate that the scaffold is not elemental cobalt, but a type of Co—B compound.

The XPS results were supported with XAS analysis. The X-ray absorption near edge structure (XANES) spectrum for the as-synthesized scaffold solution and a number of Co references are compared in FIG. 14 Panel C. The pre-edge position for the scaffold (blue line) matches well with that of Co Foil (black line) and can be attributed to a 1s to 3d electron transition. However, the intensity and slope of the feature confirm that the average oxidation state of Co in the scaffold is greater than 0, as would be expected for Co—B and in agreement with previous reports.[64] The feature at greater energy (~7725 eV) agrees well with that of $CoCl_2$ and $Co(OH)_2$ and could therefore arise from the presence of unreacted $CoCl_2$ or oxidized cobalt, in accordance with the XPS analysis. Although precautions were taken to ensure the sample remained as air-free as possible, the presence of a surface oxide layer could explain these results. Overall, the XPS and XANES results are in good agreement with what has been reported in the literature for $Co_2B$.

TABLE 2

XPS Co 2p and B 1s binding energies (BE) for the isolated scaffold product and comparison with literature references.

| Level | BE (eV) | Reference BE (eV) | Reference Species | Reference |
|---|---|---|---|---|
| B 1s | 188.3 | 188.3 | $Co_2B$ | 2 |
|  |  | 187.7 | Co-B | 3 |
|  |  | 189.0 | Co-B | 4 |
| B 1s | 192.4 | 191.3 | Oxidized $Co_2B$ | 2 |
|  |  | 191.5 | Boron-oxo | 3 |
|  |  | 191.2 | $B_2O_3$ | 4 |
| Co $2p_{3/2}$ | 778.3 | 777.6 | $Co_2B$ | 2 |
|  |  | 778.07 | $Co_2B$ | 3 |

TABLE 2-continued

XPS Co 2p and B 1s binding energies (BE) for the isolated scaffold product and comparison with literature references.

| Level | BE (eV) | Reference BE (eV) | Reference Species | Reference |
|---|---|---|---|---|
| Co $2p_{3/2}$ | 781.4 | 781.0 | $Co(OH)_2$ | 1 |
| | | 780.83 | CoO or $Co(OH)_2$ | 3 |
| | | 786.4 | $Co(OH)_2$ | 1 |
| Co $2p_{1/2}$ | 793.4 | 793.19 | $Co_2B$ | 3 |
| Co $2p_{1/2}$ | 797.4 | 796.9 | $Co(OH)_2$ | 1 |
| | | 796.75 | CoO or $Co(OH)_2$ | 3 |
| | 803.0 | 802.6 | $Co(OH)_2$ | 1 |

Hydrolysis of $BH_4^-$ to $B(OH)_4^-$

To obtain $B(OH)_4^-$, aqueous 1M $NaBH_4$ was prepared and left to hydrolyze under ambient conditions. Proton-coupled $^{11}B$ NMR was used to identity the hydrolyzed $BH_4^-$ species over the course of 48 hr. To inhibit continued hydrolysis during NMR measurements, aliquots at each timepoint were transferred to a 0.1 M KOH solution immediately before measurement as self-hydrolysis of borohydride is negligible above pH 13.[65] NMR results for 0 hr, 24 hr, and 48 hr hydrolysis timepoints are shown in FIG. 15, Panels A and B.

Before hydrolysis, the $^{11}B$ NMR spectra showed a symmetric quintet centered ~−41.7 ppm with 1:4:6:4:1 relative amplitude, indicating four magnetically equivalent, tetrahedrally arranged H atoms (FIG. 15 Panels A and B, red curve). This signal may be confidently assigned to the borohydride anion, $BH_4^-$, in agreement with previous reports.[66-68] No other NMR signals were present for the 0 hr sample. At 24 hr hydrolysis, the $BH_4^-$ quintet was still present but reduced to 13% of its original amplitude. A broad, low-field singlet also appeared ~1.7 ppm, and has previously been assigned to $B(OH)_4^-$.[66] At 48 hr hydrolysis, the NMR quintet was no longer discernible and the singlet increased in amplitude. Thus, a timespan of 48 hours is enough for full conversion of $BH_4^-$ to the final hydrolysis product. It should be noted that these measurements and all syntheses reported herein were performed with newly received $NaBH_4$ which was kept in a dry environment under nitrogen protection and opened sparingly. Because $NaBH_4$ reacts readily with moisture in the air, exact results may vary depending on chemical age and storage conditions.

Although only two species were observable in the NMR measurements, the conversion of $BH_4^-$ to $B(OH)_4^-$ likely proceeds through a number of short-lived intermediates. Without KOH, self-hydrolysis progressed and an intermediate quartet appeared downfield, centered ~−12.7 ppm with relative intensity of 1:3:3:1. This signal arises from three magnetically equivalent protons, suggesting a $BH_3$ moiety, and has been attributed in previous work to a short-lived $BH_3(OH)^-$ hydroxyborate.[66] For the present system, it has been concluded that $BH_4^-$ fully converts to $B(OH)_4^-$ within 48 hrs, potentially through a chain of hydroxyborate intermediates, with B—OH bonds replacing B—H bonds. As such, 48 hr $BH_4^-$ was used as the source of $B(OH)_4^-$ for scaffold synthesis.

Cyclic voltammetry was also used to monitor the hydrolysis conversion. The cyclic voltammogram (CV) at 0 hr hydrolysis showed one singular anodic peak at 0.0 V, attributed to $BH_4^-$ (FIG. 15, Panel D, red curve). By 48 hr hydrolysis, the $BH_4^-$ peak was essentially completely diminished (FIG. 15, Panel D, black curve). An understanding of the relative reduction potentials of $BH_4^-$ and its hydrolysis products can be used to understand the role of $B(OH)_4^-$ in the nucleation and growth of $Co_xB_y$ NPs. Because a new peak does not appear in this range by 48 hr hydrolysis, it is concluded that the final hydrolysis product is not electrochemically active within the present measurement parameters. Therefore, $B(OH)_4^-$ must have a role in scaffold formation other than the initial reduction of cobalt ions to form nucleation centers.

Elucidating the Role of $B(OH)_4^-$ in $Co_xB_y$ NP Formation

To that end, confirming that $B(OH)_4^-$ does not serve as a reducing agent. Indeed, $B(OH)_4^-$ alone does not nucleate ions in any appreciable manner; the initial cobalt ions are still present in solution 120 minutes after addition of $B(OH)_4^-$. Additionally, the spectral positions for both $B(OH)_4^-$ and hydrated $Co^{2+}$ red-shift when $B(OH)_4^-$ and $CoCl_2$ are combined, suggesting formation of a complex between $B(OH)_4^-$ and hydrated $Co^{2+}$ in the presence of citrate.

Figure 16:
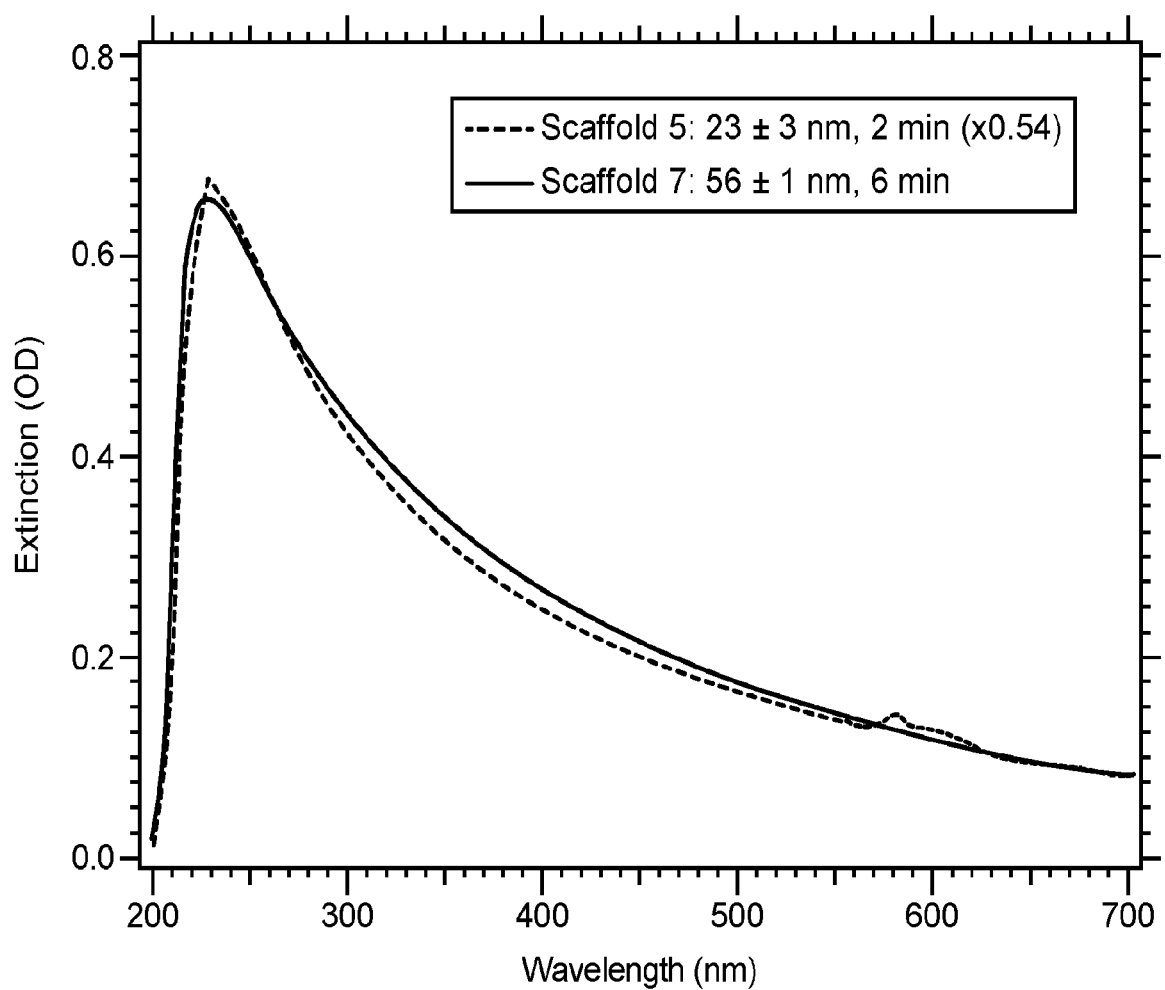
FIG. 16 Panel A: Extinction spectra for aqueous $CoCl_2$, $B(OH)_4^-$, and the combination of $CoCl_2$ and $B(OH)_4^-$ in the presence of citrate. The hydrated $Co^{2+}$ feature ~500 nm is highlighted in the inset. Panel B: For all spectra, spectral contribution from citrate was been removed to highlight the appearance of extinction below 300 nm. Panel C: Good agreement in extinction profile between $Co_xB_y$ NP Scaffold 7: 56±1 nm at six minute growth and Scaffold 5: 23±3 nm at two minute growth (scaled by 0.54 on the y-axis).

Interestingly, the spectral profile for Scaffold 7 at six minutes is equivalent to that of Scaffold 5 at two minutes, although only 54% of the intensity, as shown in FIG. 16 Panel C. Shown herein is that the shape of the extinction curve is indicative of particle diameter, which suggests that Scaffold 7 is able to create the same size clusters as Scaffold 5, but roughly half as many over a longer period of time. This suggests that the two scaffolds formed through the same initial mechanism, albeit at different speeds and to different extents. After this point, the scaffold growth behaviors deviated; Scaffold 5 remained unchanged while Scaffold 7 grew for an additional 2 minutes, leading to a broader extinction profile and larger diameter. This observation supports the proposed growth mechanism. Concluded herein is that while $BH_4^-$ is responsible for reduction of the $Co^{2+}$ ions, $B(OH)_4^-$ serves as a growth agent.

In order to clearly examine the temporal behavior of each species, singular-value decomposition (SVD) was used to deconvolve the spectral contributions from the $Co^{2+}$+$B(OH)_4^-$ complex and the $Co_xB_y$ scaffold. SVD enables factorization of the spectral evolution of Scaffold 7 by the following equation:

$$M = U\Sigma V^T \quad \text{Equation (2)}$$

where M represents the original Scaffold 7 spectrotemporal matrix, U comprises eigenvectors of $MM^T$, $\Sigma$ is a singular value matrix comprising the square roots of nonzero eigenvalues of $MM^T$ and $M^TM$, V comprises eigenvectors of $M^TM$, and $V^T$ is the conjugate transpose of V.

Figure 17:
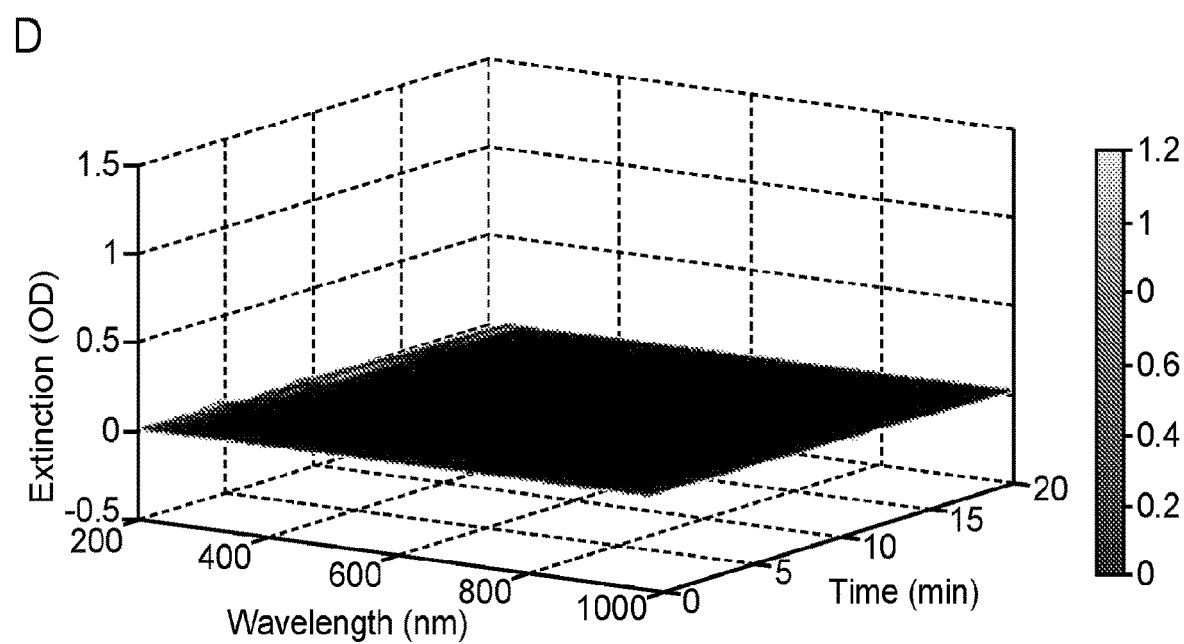
FIG. 17 SVD of Scaffold 7. Panel A: Spectral evolution of Scaffold 7: 56±1 nm extinction over the course of 20 minutes. Panel B: SVD representation of the data using two basis vectors. Panel C: Time-independent (U) and wavelength-independent (V) basis vectors extracted from SVD of Panel A. Panel D: SVD residual.

All SVD calculations were carried out in MatLab. FIG. 17 Panel B represents a recreation of M using the first two basis vectors extracted by SVD. The time-independent vectors, $U_1$ and $U_2$, are shown in FIG. 17 Panel C. Based on their spectral profiles, $U_1$ can be correlated to the $Co^{2+}$+$B(OH)_4^-$ complex and $U_2$ to the $Co_xB_y$ scaffold. The time component for each (the corresponding wavelength-independent basis vectors, $V_1$ and $V_2$) are also shown. The $\Sigma$ matrix included singular values of 14.6379 and 0.8163 for $\sigma_{1,1}$ and $\sigma_{2,2}$, respectively. Comparison of the recreation with the original spectra (FIG. 17 Panels A and B) reveal that this is a good interpretation of the data. The residual is provided in FIG. 17 Panel D.

With successful deconvolution, the spectral contribution of the $Co_xB_y$ scaffold at 230 nm was then determined by multiplying the $V_1$ vector by two scalers: the associated singular value ($\sigma_1$) and the associated time-dependence at 220 nm ($u_{1,220nm}$). The spectral contribution of the $Co^{2+}$+$B(OH)_4^-$ complex at 220 nm was also determined in this manner. Associated equations are provided below, and results are shown in FIG. 9 Panel D of the main text.

$$Co_2B_{230nm} = u_{1,230nm}\sigma_{1,1}V_1 \quad \text{Equation (3)}$$

$$Co^{2+}+B(OH)_{4\ 220nm}^- = u_{2,220\ nm}\sigma_{2,2}V_2 \quad \text{Equation (4)}$$

The Effect of Environmental Oxygen during Galvanic Exchange for the Formation of HGNs from $Co_xB_y$ NP Scaffolds The optical and structural effects of environmental oxygen during galvanic exchange have previously been described. Here, additional extinction spectra and high-resolution transmission electron microscopy (HRTEM) images are provided for galvanic exchange between $Co_xB_y$ Scaffold 7 and $HAuCl_4$ amounts ranging from 0.20 to 1.0 μmol. $Co_xB_y$ Scaffold 7 was made with 5.00 $BH_4^-$:$Co^{2+}$ and 1.00 $B(OH)_4^-$:$BH_4^-$ mole ratios and had a hydrodynamic diameter of 56±1 nm.

The stabilization of thinner shells with the anaerobic galvanic exchange protocol is especially advantageous when trying to red-shift smaller diameter HGNs. This is demonstrated in FIG. 19, where $Co_xB_y$ Scaffold 5 was taken through galvanic exchange with 0.30 μmol $HAuCl_4$, using both aerobic and anaerobic protocols. $Co_xB_y$ Scaffold 5 was made with 5.00 $BH_4^-$:$Co^{2+}$, included no $B(OH)_4^-$ growth agent, and had a hydrodynamic diameter of 23±3 nm.

The Effect of Environmental Oxygen During Residual Core Oxidation in the Formation of HGNs from $Co_xB_y$ NP Scaffolds In the conversion of a $Co_xB_y$ NP to an HGN, shown herein is that oxygen is a reactant in galvanic exchange, affecting the structural and optical properties of the final product. To this end, the effect of oxygen was assessed during the final synthesis step, the residual $Co_xB_y$ NP core oxidation. Specifically, the rate of $Co_xB_y$ NP removal from the $Co_xB_y$/Au structures was analyzed. To do so, aliquots of the same $Co_xB_y$ NP/Au solution were oxidized with either 700 rpm stirring for 3 minutes or with vortexing for 10 seconds. Vortexing maximizes the $Co_xB_y$ NP/Au solution-air interface and thus represents a relatively instantaneous oxidation. This was done for $Co_xB_y$ NP/Au solutions made from Scaffold 7 $Co_xB_y$ NPs taken through anaerobic galvanic exchange with 0.40 and 0.50 μmol $HAuCl_4$. Resultant extinction spectra are shown in FIG. 20, where the solid line represents the 700 rpm oxidation protocol and the circle markers represent the vortex oxidation protocol. The dashed lines in FIG. 20 Panels A and B represent the previously discussed aerobic oxidation method and are added for easy SPR comparison. HRTEM images corresponding to FIG. 20 Panel A are provided for structural comparison (FIG. 20 Panels C and D).

For HGNs made with 0.40 μmol and 0.50 μmol $HAuCl_4$ (FIG. 20 Panels A and B respectively), vortex oxidation resulted in an additional, non-negligible red-shift of the SPR: a 35 nm shift for the 0.40 μmol $HAuCl_4$ HGNs and a 45 nm shift for the 0.50 μmol $HAuCl_4$ HGNs. This suggests that the shell is still alterable even after galvanic exchange. The corresponding HRTEM images reveal that the vortex protocol generated shells with many thin and holey areas. It could be the case that the vortex protocol removes the cobalt from the core so quickly that a greater number of routes of cobalt extraction are accessed/created.

Example 3—Hollow Metal Nanosphere Surface Morphology Control Via pH Modulation

Introduction

The photophysical properties of HGNs are strongly influenced by their surface morphology. Absorption, scattering, and coherent vibrational oscillations can all be tuned by modifying the HGN surface. In addition, creating bumpy surface structures can provide increased surface area for catalytic reactions or loading of drug or targeting ligands, allowing tuning of HGN performance for photothermal therapy, diagnostic imaging, and catalysis. Moreover, the bumpy HGNs retain their hollow core, providing increased performance at lower weight and lower cost (less material) as compared to similarly-sized solid nanostructures.

Shown in the present example is that the surface morphology of hollow metal nanospheres may be controlled by modulating the pH at which galvanic exchange occurs. In this particular example, the surface morphology of hollow gold nanospheres (HGNs) is controlled by modulation of pH.

HGN Synthesis for Surface Morphology Control

A $Co_xB_y$ solution and a gold solution are prepared as described in Example 1 or Example 2 herein.

As the gold solution is stirred, a pH modulation agent (in this example, NaOH, e.g., 1M NaOH) is added to modulate the pH as desired, e.g., increase the pH to a desired pH using NaOH. The inventors determined that pH ~4 produced slightly rough structures, pH ~7 produced rough structures, and pH ~10 produced very rough structures. pH>11 may result in the particles being so rough that the shells essentially fall apart.

Next, an aliquot of the $Co_xB_y$ solution is transferred to the stirring, pH-modified gold solution via cannula transfer. The gold may be deaerated or not deaerated. Deaeration of the gold will produce a red-shifted SPR.

Figure 7:
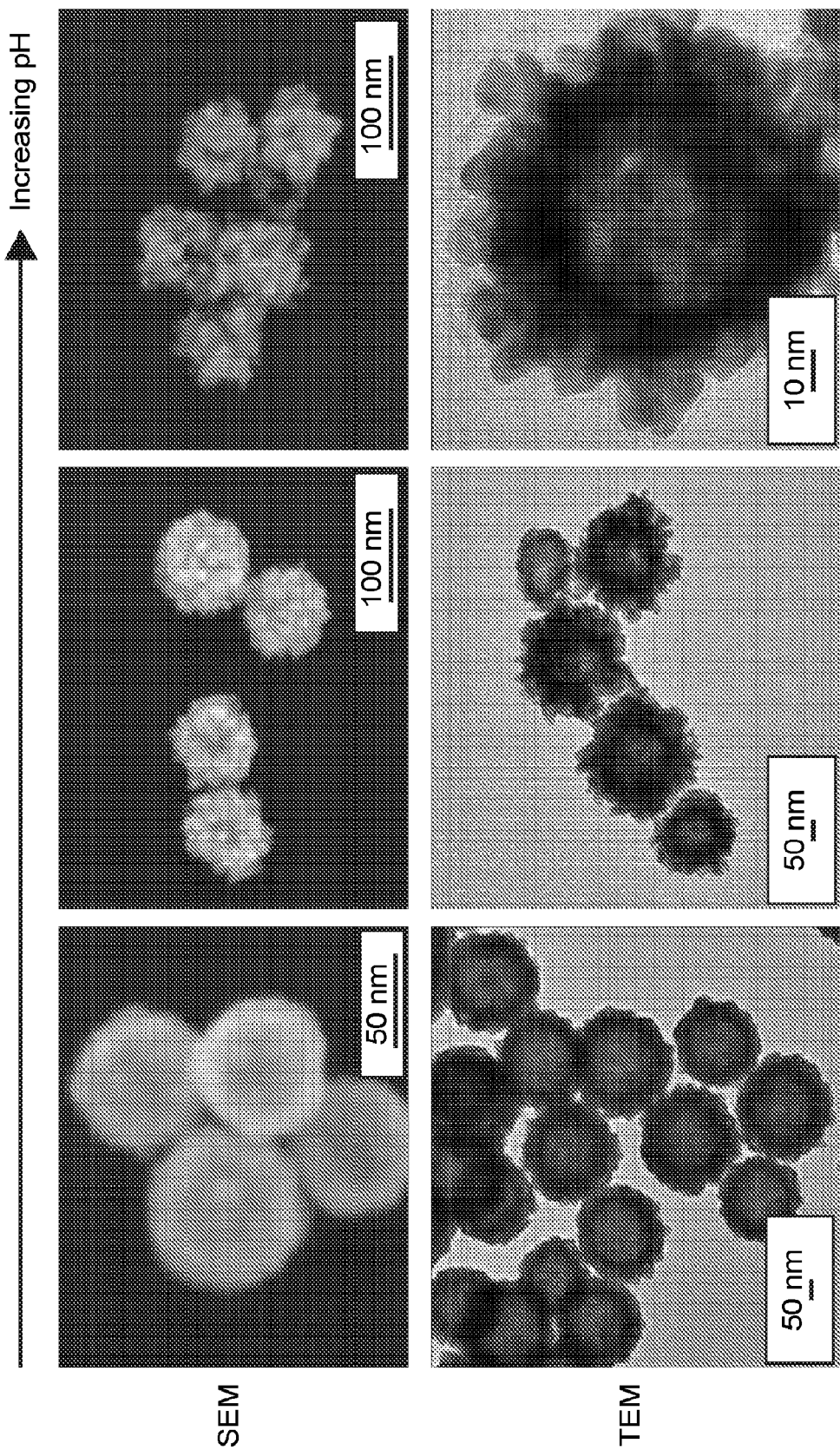
FIG. 7 SEM and transmission electron microscope (TEM) images of HGNs synthesized with increasing surface roughness by increasing the pH of the gold solution from 3 to 10 before galvanic exchange.

Shown in FIG. 7 are the resulting HGNs as the pH of the chloroauric acid is taken from pH 3 to pH 10 before galvanic exchange. Generally, when the gold is kept at its initial pH ~3, the resultant structure is smooth. When the pH of the chloroauric acid is increased to pH ~4-5 with addition of NaOH, small studs form on the resultant HGN shell. When the pH is further increased to pH ~6-8, the shell becomes very rough. Further increase to pH 10 results in very jagged structures. The galvanic exchange, a very quick process at acidic pH, takes longer to occur at the basic pH conditions.

In addition to different structural properties, the resultant structures exhibit different optical properties. The SPR red-shifts with an increase in surface roughness. The full-width-half-max (FWHM) also broadens with increasing surface roughness.

Control experiments were performed to investigate the mechanism behind the structural surface change. When galvanic exchange was performed immediately upon NaOH addition (at high pH), the resultant SPR was dramatically red-shifted and the shell surface was very jagged. When the same amount of NaOH was added, but the solution allowed to equilibrate for 60 minutes, the resultant SPR was not as red-shifted and the shell surface was far less jagged. When the solution was allowed to equilibrate, the pH slowly dropped, indicating fewer free $OH^-$ ions in solution. During this time, the free $OH^-$ in solution likely replaced the chloride ligands on chloroauric acid. Depending on the degree of replacement, $HAuCl_4$ can become $HAuCl_3OH$, $HAuCl_2OH_2$, $HAuClOH_3$, or $HAuOH_4$, with greater replacement favored with increasing basicity. The speciation of $HAuCl_4$ greatly affects its reactivity and was considered as a possible explanation for the jagged structure. However, because the resultant shell morphology was only slightly jagged when the solution was allowed the equilibrate for 60 minutes, it is likely the presence of free $OH^-$ in solution, not the speciation of $HAuCl_4$, that dictates the final structure.

The inventors have found that a constant absorption wavelength can be maintained while varying the thickness of the bumpy shell by keeping the Au:OH ratio constant while increasing or decreasing the volume of gold. This means that the particle diameter can be increased or decreased while maintaining the very bumpy surface and also maintaining an SPR of choice.

Example 4—Production of HMNs with Enhanced Absorption and Heat Generation

Introduction

Nanoparticles can both absorb and scatter incident light, with absorption/scattering ratios that are size- and structure-dependent. Thus, a high degree of optical and structural tunability is necessary for use in applications that rely on their photophysical performance. One such application is plasmonic photothermal therapy (PTT). In PTT, plasmonic nanoparticles are targeted to cancer cells where they act as nanoscale light-to-heat converters, absorbing incident light and converting it to heat, raising the temperature of the cancerous environment above the point of cell viability. Because it is the absorbed light that is converted to heat, it is desirable to optimize the dimensions of a nanoparticle to maximum the absorption component of light extinction. Additionally, PTT is both size-restrictive and SPR-restrictive: the particles should be below 100 nm for optimum biocompatibility and the particles should have an SPR in the near-infrared (NIR) to match the NIR window of biological tissue.

Hollow gold nanospheres (HGNs) are ideal candidates for plasmonic PTT. They are nontoxic, highly biocompatible in terms of composition and size range, and can be made with a strong SPR in the NIR. Furthermore, their two-fold tunability as demonstrated in the preceding Examples allows the formation of different diameters with NIR SPR. As such, HGNs may be studied as model systems for understanding the size dependence of extinction, absorption, scattering, and photothermal conversion, and the size that maximizes absorption may be identified.

In the present Example, discrete dipole approximation (DDA) was used to model HGNs of different diameters, each with shell thickness selected for 795 nm SPR. The results indicate that diameters ~50 nm will maximize the absorption component of the extinction and could therefore maximize heat generation. Experimental studies support this calculation. HGNs of different sizes were synthesized with 795 nm SPR and heat generation studies were carried out to assess and compare the photothermal coupling ability of the particles. For each size, photothermal coupling efficiency was assessed as a function of amount of gold. The findings reveal that 50 nm HGNs generate ~2 times the heat per μg gold as their 70 nm counterparts and ~1.5 times the heat per μg gold as their 30 nm counterparts.

Materials and Methods

DDA Simulation

Extinction simulation was carried out using the discrete dipole approximation (DDA) method with the latest version of DDSCAT 7.3 software. The HGNs were modeled as solvent-filled shells of gold, with outer diameter of 25, 30, 35, 40, 45, 70, and 90 nm and shell thickness of 1.4, 1.7, 2.0, 2.3, 2.6, 4.3, 5.7 nm, respectively. In each case, the shell thickness was selected to result in an SPR ~795 nm for each size. Absorption and scattering contributions were calculated separately. The dielectric function of gold was chosen from Johnson and Christy's study and the refractive index of water was chosen for that of the inner and outer surrounding medium.

Synthesis of $Co_xB_y$ NP Scaffolds

Cobalt(II) chloride hexahydrate ($CoCl_2.6H_2O$) was purchased from Sigma-Aldrich, trisodium citrate dihydrate ($Na_3C_6H_5O_7.2H_2O$) was purchased from VWR International, and sodium borohydride ($NaBH_4$) was purchased from Fisher Scientific. All water used in synthesis was ultrapure in quality, with a resistivity of 18.3 MΩ.

$Co_xB_y$ NP scaffolds were synthesized in accordance with the preceding Examples. Briefly, a 100 mL solution of 0.40 mM $CoCl_2.6H_2O$ and 4.0 mM $Na_3C_6H_5O_7.2H_2O$ was prepared in a 500 mL round bottom flask and deaerated by bubbling with nitrogen for 1 hour. During this time, the solution was stirred at 700 RPM with a magnetic stir bar. Then, a given volume of freshly prepared aqueous 1 M $NaBH_4$ was injected while the solution continued to stir under nitrogen protection. After addition of $NaBH_4$, the solution turned from pale pink to brown, indicating the reduction of $Co^{2+}$ ions and the formation of the $Co_xB_y$ NP scaffold. After 2 minutes, the stir bar was magnetically suspended above the solution and the $Co_xB_y$ NPs were subsequently allowed to stand under constant nitrogen flow for 2 hours to ensure complete hydrolysis of the borohydride reducing agent. The size of the $Co_xB_y$ scaffold was controlled by adding a given volume of $B(OH)_4^-$ (20-200 μL) to the freshly prepared aqueous 1 M $NaBH_4$ before injection into the cobalt salt solutions. To obtain $B(OH)_4^-$, a 1.0 mL aliquot of aqueous 1.0 M $NaBH_4$ was prepared and allowed to hydrolyze in ambient conditions for 48 hr.

Synthesis and PEGylation of HGNs with 790 nm SPR

Chloroauric acid ($HAuCl_4$) was purchased from Fisher Scientific. Heterobifunctional polyethylene glycol functionalized with orthopyridyl disulfide and succinimidyl valerate (OPSS-PEG-SVA) was purchased from Laysan Bio, Inc. All water used in synthesis was ultrapure in quality, with a resistivity of 18.3 MΩ. For anaerobic galvanic exchange, a given volume (3.6-10.0 μL) of 0.10 M $HAuCl_4$ was added to 30 mL ultrapure water and deaerated by bubbling with nitrogen gas for one hour under magnetic stirring at 700 RPM. Once deaerated, galvanic exchange was initiated by transferring 30 mL of the $Co_xB_y$ NP solution to the stirring gold solution via air-free cannula transfer. The resultant core/shell Co NP/Au particles were stirred for two minutes under nitrogen protection at 700 rpm before final oxidation of the remaining $Co_xB_y$ NP cores. The residual cobalt cores were fully oxidized by removing the septa and stirring at 700 rpm for five minutes under ambient conditions. Resultant HGNs were centrifuged twice at 1300 rpm for 3 minutes and resuspended in ultrapure water to a concentration of 4.0 OD. For PEGylation, 100 μl of 1 mg/ml OPSS-PEG-SVA was added to 500 μl of 4.0 OD HGN and shaken overnight. The resultant HGN-PEG solution was centrifuged once at 1300 rpm for 3 minutes to remove residual PEG and resuspended in ultrapure water.

UV-Vis Spectroscopy

UV-Vis spectra were recorded with an Agilent Technologies Cary 60 UV-Vis spectrophotometer using a 700 μL quartz cuvette with standard 10 mm optical path length.

Electron Microscopy

High-resolution transmission electron microscopy (HR-TEM) was performed at the National Center for Electron Microscopy (NCEM) at the Lawrence Berkeley National Laboratory Molecular Foundry on an FEI UT Tecnai microscope operated at 200 kV acceleration voltage. Before HRTEM, as-prepared HGN solutions were centrifuged twice in ambient conditions at 13,000 RPM for 3 minutes and resuspended in ultrapure water.

Heat Generation Measurement 1 ml of HGN-PEG was placed in a quartz cuvette and exposed to a 795 nm NIR CW laser with spot size of 7 mm and power density of 1 W/cm². The solution was stirred continuously at 300 rpm. The laser was incident upon the sample for 25 minutes (heating cycle) and then blocked for 25 minutes (cooling cycling). For each heating and cooling cycle, the temperature of the solution was measured continuously with a 33-gauge hypodermic thermocouple (Omega) and data logger (Supco) at a rate of one readout per second. The thermocouple was placed directly in the solution. The solution remained capped for the entirety of the measurement. For each size, heat generation measurements were taken on four particle concentrations (1.0, 0.5, 0.25, and 0.125 OD).

Results

Simulation of Size-Dependent Extinction

Figure 22:
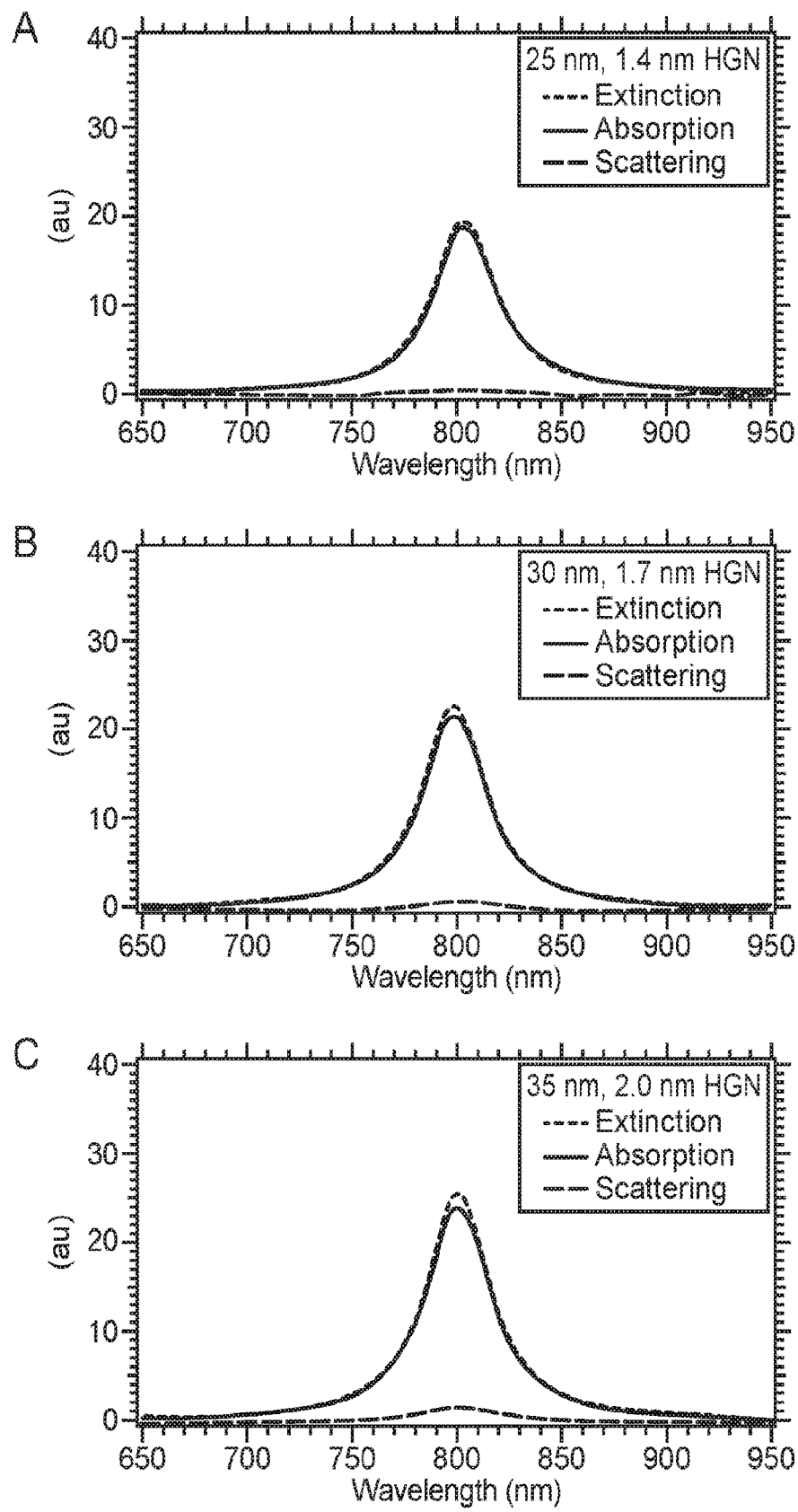
FIG. 22 DDA simulation of the absorption and scattering components of HGN extinction for diameter, shell combinations of a) 25 nm, 1.4 nm, b) 30 nm, 1.7 nm, c) 35 nm, 2.0 nm, d) 40 nm, 2.3 nm, e) 45 nm, 2.6 nm, f) 70 nm, 4.3 nm, and g) 90 nm, 5.7 nm. In each case, shell thickness has been tuned for SPR ~795 nm. Comparison of percent absorption (%A) and absorption-to-scattering ratios (A/S) as a function of diameter, measured at a wavelength of 795 nm (panel H) and the extinction, absorption, and scattering values (panel I).
Figure 22:
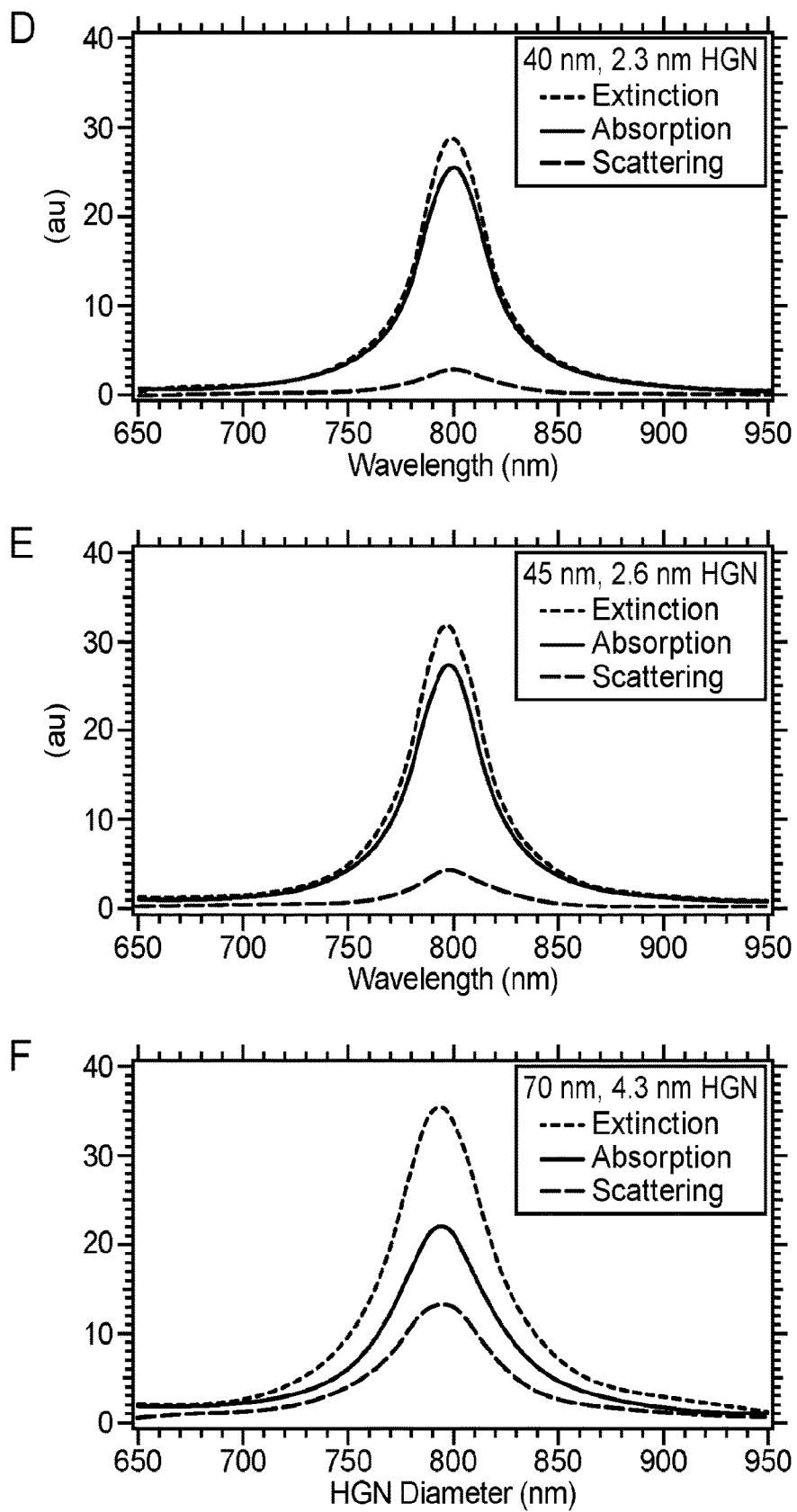
Figure 22:
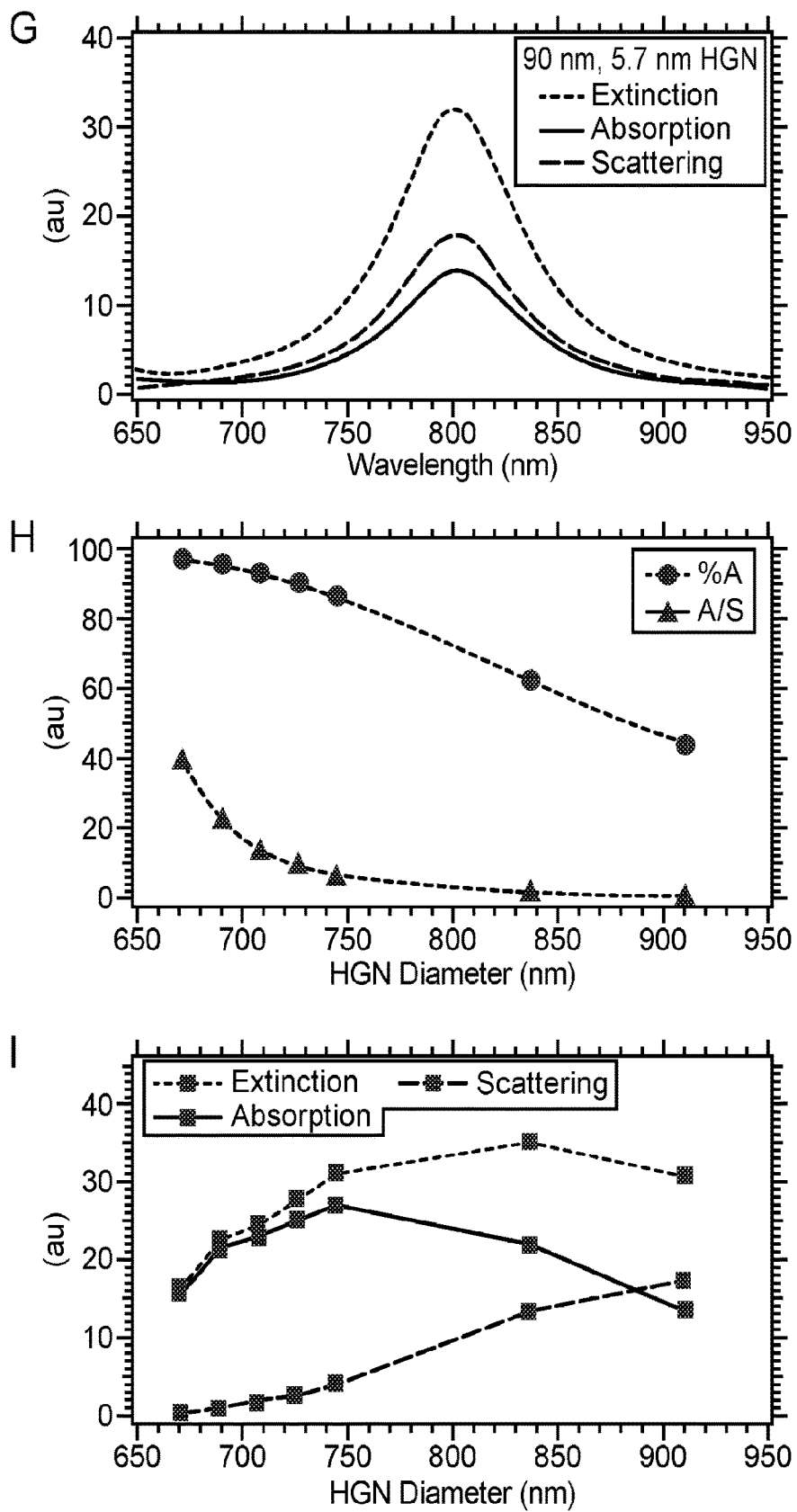

The simulated extinctions, with absorption and scattering components, are shown in FIG. 22, panels A-H for HGNs with 25, 30, 35, 40, 45, 70, and 90 nm outer diameter and 1.4, 1.7, 2.0, 2.3, 2.6, 4.3, and 5.7 nm shell thickness, respectively. For each diameter, the shell thickness has been selected for 795 nm SPR, to be compatible with the NIR window of biological tissue. It is apparent that 25 nm HGNs are almost entirely absorbing, with absorption accounting for 97.5% of the extinction and an absorption:scattering ratio (A/S) of 39.7. As the particle diameter increases, however, the scattering component increases. Once the particle reaches 90 nm, absorption accounts for only 43.8% of the extinction and the A/S decreases to 0.78. The percent absorption (% A) and A/S are compiled in FIG. 22, panel H. However, because the total extinction also changes with particle size, absolute absorption as a function of diameter peaks ~50 nm, as seen in FIG. 22, panel H. Thus, it appears there is an optimum HGN diameter for light absorption. Furthermore, it is not likely that HGNs above 70 nm will be efficient heat generators since the % A drops drastically, and scattering becomes a major contributor to total extinction.

Structural and Optical Characterization of HGNs

To test the absorption and heat generation experimentally, three sizes of HGNs (30, 50, and 70 nm) were synthesized with SPR ~795 nm. SEM images and resultant extinction spectra are displayed in FIG. 23. Reagent information is given in Table 3.

TABLE 3

Reagent information for HGNs with 795 nm SPR.

| HGN Diameter | $BH_4^-:Co^{2+}$ | $B(OH)_4^-:BH_4^-$ | $Au^{3+}$ (µmol) |
|---|---|---|---|
| 30 nm | 9.0 | 0.11 | 0.36 |
| 50 nm | 5.0 | 1.0 | 0.55 |
| 70 nm | 2.5 | 2.0 | 0.75 |
| 90 nm | 2.0 | 2.5 | 1.0 |

Experimental Heat Generation and Photothermal Conversion Efficiency

Heat generation measurements allow temperature increase to be determined as a function of amount of gold. Results show that 50 nm HGNs are capable of producing two times the heat per µg gold as their 70 nm counterparts and 1.5 times the heat per µg gold as their 30 nm counterparts.

TABLE 4

Size-Dependent Heat Generation Efficiency for 795 nm SPR HGNs.

| | Heat Generation (C.°/µg) | | |
|---|---|---|---|
| Extinction (OD) | 30 nm | 50 nm | 70 nm |
| 1.0 | 0.43 | 0.65 | 0.31 |
| 0.50 | 0.68 | 1.1 | 0.47 |
| 0.25 | 0.85 | 1.3 | 0.58 |
| 0.125 | 1.1 | 1.7 | 0.71 |

REFERENCES (1) Papavassiliou, G. C. Optical Properties of Small Inorganic and Organic Metal Particles. Prog. Solid St. Chem. 1979, 12, 185-271.
(2) Creighton, J. A.; Eadon, D. G. Ultraviolet-Visible Absorption Spectra of the Colloidal Metallic Elements. J. Chem. Soc. Faraday Trans. 1991, 87, 3881-3891.
(3) Link, S.; El-Sayed, M. A. Size and Temperature Dependence of the Plasmon Absorption of Colloidal Gold Nanoparticles. J. Phys. Chem. B 2009, 103, 4212-4217.
(4) Sherry, L. J.; Jin, R.; Mirkin, C. A.; Schatz, G. C.; Van Duyne, R. P. Localized Surface Plasmon Resonance Spectroscopy of Single Silver Triangular Nanoprisms. Nano Lett. 2006, 6, 2060-2065.
(5) Jain, P. K.; Lee, K. S.; El-Sayed, I. H.; El-Sayed, M. A. Calculated Absorption and Scattering Properties of Gold Nanoparticles of Different Size, Shape, and Composition: Applications in Biological Imaging and Biomedicine. J. Phys. Chem. B 2006, 110, 7238-7248.
(6) Lim, W.; Gao, Z. Plasmonic Nanoparticles in Biomedicine. Nano Today 2016, 11, 168-188.
(7) Lane, L.; Qian, X.; Nie, S. SERS Nanoparticles in Medicine: From Label-Free Detection to Spectroscopic Tagging. Chem. Rev. 2015, 115, 10489-10529.
(8) Peng, H.; Strohsahl, C. M.; Leach, K. E.; Krauss, T. D.; Miller, B. L. Label-Free DNA Detection on Nanostructured Ag Surfaces. ACS Nano 2009, 3, 2265-2273.
(9) Kosaka, P. M.; Pini, V.; Ruz, J. J.; Da Silva, R. A.; Gonzalez, M. U.; Ramos, D.; Calleja, M.; Tamayo, J. Detection of Cancer Biomarkers in Serum Using a Hybrid Mechanical and Optoplasmonic Nanosensor. Nat. Nanotechnol. 2014, 9, 1047-1053.
(10) You, J.; Zhang, G.; Li, C. Exceptionally High Payload of Doxorubicin in Hollow Gold Nanospheres for Near-Infrared Light-Triggered Drug Release. ACS Nano 2010, 4, 1033-1041.
(11) Vijayaraghavan, P.; Liu, C.; Vankayala, R.; Chiang, C.; Hwang, K. C. Designing Multi-Branched Gold Nanoechinus for NIR Light Activated Dual Modal Photodynamic and Photothermal Therapy in the Second Biological Window. Adv. Mater. 2014, 26, 6689-6695.
(12) Xing, R.; Liu, K.; Jiao, T.; Zhang, N.; Ma, K.; Zhang, R.; Zou, Q.; Ma, G.; Yan, X. An Injectable Self-Assembling Collagen-Gold Hybrid Hydrogel for Combinatorial Antitumor Photothermal/Photodynamic Therapy. Adv. Mater. 2016, 28, 3669-3676.
(13) Yang, P.; Zheng, J.; Xu, Y.; Zhang, Q.; Jiang, L. Colloidal Synthesis and Applications of Plasmonic Metal Nanoparticles. Adv. Mater. 2016, 28, 10508-10517.
(14) Maier, S.; Brongersma, M. L.; Kik, P. G.; Meltzer, S.; Requicha, A. A. G.; Atwater, H. Plasmonics—A Route to Nanoscale Optical Devices. Adv. Mater. 2001, 13, 1501-1505.

(15) Sheldon, M. T.; Van de Groep, J.; Brown, A. M.; Polman, A.; Atwater, H. A. Plasmoelectric Potentials in Metal Nanostructures. Science 2014, 346, 829-831.

(16) Choi, H.; Ko, S.; Choi, Y.; Joo, P.; Kim, T.; Lee, B. R.; Jung, J. W.; Choi, H. J.; Cha, M.; Jeong, J.; Hwang, I.; Song, M. H.; Kim, B.; Kim, J. Y. Versatile Surface Plasmon Resonance of Carbon-Dot Supported Silver Nanoparticles in Polymer Optoelectronic Devices. Nat. Phot. 2013, 7, 732-738.

(17) Kim, T.; Kang, H.; Jeong, S.; Kang, D. J.; Lee, C.; Lee, C.; Seo, M.; Lee, J.; Kim, B. J. Au@Polymer Core-Shell Nanoparticles for Simultaneously Enhancing Efficiency and Ambient Stability of Organic Optoelectronic Devices. ACS Appl. Mater. Interfaces 2014, 6, 16956-16965.

(18) Zhong, L.; Jiang, Y.; Liow, C.; Meng, F.; Sun, Y.; Chandran, B.; Liang, Z.; Jiang, L.; Li, S.; Chen, X. Highly Sensitive Electro-Plasmonic Switches Based on Fivefold Stellate Polyhedral Gold Nanoparticles. Small 2015, 11, 4395-5401.

(19) Linic, S.; Christopher, P.; Ingram, D. B. Plasmonic-Metal Nanostructures for Efficient Conversion of Solar to Chemical Energy. Nat. Mater. 2011, 10, 911-921.

(20) Clavero, C. Plasmon-Induced Hot-Electron Generation at Nanoparticle/Metal-Oxide Interfaces for Photovoltaic and Photocatalytic Devices. Nat. Photonics 2014, 8, 95-103.

(21) Meng, X.; Liu, L.; Ouyang, S.; Xu, H.; Wang, D.; Zhao, N.; Ye, J. Nanometals for Solar-to-Chemical Energy Conversion: From Semiconductor-Based Photocatalysis to Plasmon-Mediated Photocatalysis and Photo-Thermocatalysis. Adv. Mater. 2016, 28, 6781-6803.

(22) Christopher, P.; Xin, H.; Linic, S. Visible-Light-Enhanced Catalytic Oxidation Reactions on Plasmonic Silver Nanostructures. Nat. Chem. 2011, 3, 467-472.

(23) Liu, H.; Meng, X.; Dao, T. D.; Zhang, H.; Li, P.; Chang, K.; Wang, T.; Li, M.; Nagao, T.; Ye, J. Conversion of Carbon Dioxide by Methane Reforming under Visible-Light Irradiation: Surface-Plasmon-Mediated Nonpolar Molecule Activation. Angew. Chem. Int. Ed. 2015, 54, 11545-11549.

(24) Sun, Y.; Mayers, B.; Xia, Y. Metal Nanostructures with Hollow Interiors. Adv. Mater. 2003, 15, 641-646.

(25) Mahmoud, M. A.; Snyder, B.; El-Sayed, M. A. Surface Plasmon Fields and Coupling in the Hollow Gold Nanoparticles and Surface-Enhanced Raman Spectroscopy. Theory and Experiment. J. Phys. Chem. C 2010, 114, 7436-7443.

(26) Zeng, J.; Zhang, Q.; Chen, J.; Xia, Y. A Comparison Study of the Catalytic Properties of Au-Based Nanocages, Nanoboxes, and Nanoparticles. Nano Lett. 2010, 10, 30-35.

(27) Genc, A.; Patarroyo, J.; Sancho-Parramon, J.; Bastús, N. G.; Puntes, V.; Arbiol, J. Hollow Metal Nanostructures for Enhanced Plasmonics: Synthesis, Local Plasmonic Properties, and Applications. Nanophotonics 2017, 6, 193-213.

(28) Hazra, B.; Chandra, M. Plasmon Hybridization Mediated Structure-Specific Refractive Index Sensitivity of Hollow Gold Nanoprism in the Vis-NIR Region. ACS Sens. 2016, 1, 536-542.

(29) Schwartzberg, A.; Olson, T. Y.; Talley, C. E.; Zhang, J. Z. Synthesis, Characterization, and Tunable Optical Properties of Hollow Gold Nanospheres. J. Phys. Chem. B 2006, 110, 19935-19944.

(30) Newhouse, R. J.; Wang, H.; Hensel, J. K.; Wheeler, D. A.; Zou, S.; Zhang, J. Z. Coherent Vibrational Oscillations of Hollow Gold Nanospheres. J. Phys. Chem. Lett. 2011, 2, 228-235.

(31) Dowgiallo, A.; Schwartzberg, A. M.; Knappenberger, K. L. Structure-Dependent Coherent Acoustic Vibrations of Hollow Gold Nanospheres. Nano. Lett. 2011, 11, 3258-3262.

(32) Dowgiallo, Z.; Knappenberger, K. L. Ultrafast Electron-Phonon Coupling in Hollow Gold Nanospheres. Phys. Chem. Chem. Phys. 2011, 13, 21585-21592.

(33) Preciado-Flores, S.; Wang, D.; Wheeler, D. A.; Newhouse, R.; Hensel, J. K.; Schwartzberg, A.; Wang, L.; Zhu, J.; Barboza-Flores, M.; Zhang, J. Z. Highly Reproducible Synthesis of Hollow Gold Nanospheres with Near Infrared Surface Plasmon Absorption Using PVP as a Stabilizing Agent. J. Mater. Chem. 2011, 21, 2344-2350.

(34) Adams, S.; Thai, D.; Mascona, X.; Schwartzberg, A. M.; Zhang, J. Z. Key Factors Affecting the Reproducibility of Synthesis and Growth Mechanism of Near-Infrared Absorbing Hollow Gold Nanospheres. Chem. Mater. 2014, 26, 6805-6810.

(35) Adams, S.; Zhang, J. Z. Unique Optical Properties and Applications of Hollow Gold Nanospheres (HGNs). Coord. Chem. Rev. 2016, 320-321, 18-37.

(36) Schwartzberg, A. M.; Oshiro, T. Y.; Zhang, J. Z.; Huser, T.; Talley, C. E. Improving Nanoprobes Using Surface-Enhanced Raman Scattering from 30-nm Hollow Gold Particles. Anal. Chem. 2006, 78, 4732-4736.

(37) Lee, S.; Chon, H.; Lee, M.; Choo, J.; Shin, S. Y.; Lee, Y. H.; Rhyu, I. J.; Son, S. W.; Oh, C. H.; Surface-Enhanced Raman Scattering Imaging of HER2 Cancer Markers Overexpressed in Single MCF7 Cells Using Antibody Conjugated Hollow Gold Nanospheres. Biosens. Bioelectron. 2009, 24, 2260-2263.

(38) Lu, W.; Melancon, M. P.; Xiong, C.; Huang, Q.; Elliott, A.; Song, S.; Zhang, R.; Flores, L. G.; Gelovani, J. G.; Wang, L. V.; Ku, G.; Stafford, R. J.; Li, C. Effects of Photoacoustic Imaging and Photothermal Ablation Therapy Mediated by Targeted Hollow Gold Nanospheres in an Orthotopic Mouse Xenograft Model of Glioma. Cancer Res. 2011, 71, 6116-6121.

(39) Liang, H.; Wan, L.; Bai, C.; Jiang, L. Gold Hollow Nanospheres: Tunable Surface Plasmon Resonance Controlled by Interior-Cavity Sizes. J. Phys. Chem. B 2005, 109, 7795-7800.

(40) Chen, Y.; Liew, K. Y.; Li, J. Size Controlled Synthesis of Co Nanoparticles by Combination of Organic Solvent and Surfactant. Appl. Surf. Sci. 2009, 255, 4039-4044.

(41) Dávila-Ibáñez, A. B.; Legido-Soto, J. L.; Rivas, J.; Salgueirino, V. Amorphous Tunable-Size Co—B Magnetic Nanoparticles from the Cobalt-Catalyzed NaBH4 Hydrolysis. Phys. Chem. Chem. Phys. 2011, 13, 20146-20154.

(42) Pu, Y.; Song, F.; Zhang, W.; Lindley, S.; Adams, S.; Zhang, J. Z. Size-Tunable Synthesis of Hollow Gold Nanospheres through Control of Reaction Temperature. Part. Part. Syst. Charact. 2017, 34, 1600255.

(43) An, K.; Hyeon, T. Synthesis and Biomedical Applications of Hollow Nanostructures. Nano Today 2009, 4, 359-373.

(44) Chen, M.; Gao, L. Synthesis and Characterization of Ag Nanoshells by a Facile Sacrificial Template Route through in situ Replacement Reaction. Inorg. Chem. 2006, 45, 5145-5149.

(45) Zeng, J.; Huang, J.; Lu, W.; Wang, X.; Wang, B.; Zhang, S.; Hou, J. Necklace-like Noble-Metal Hollow Nanoparticle Chains: Synthesis and Tunable Optical Properties. Adv. Mater. 2007, 19, 2172-2176.
(46) Liang, H.; Zhang, H.; Hu, J.; Guo, Y.; Wan, L.; Bai, C. Pt Hollow Nanospheres: Facile Synthesis and Enhanced Electrocatalysis. Angew. Chem. 2004, 116, 1566-1569.
(47) Glavee, G. N.; Klabunde, K. J.; Sorensen, C. M.; Hadjapanayis, G. C. Borohydride Reductions of Metal Ions. A New Understanding of the Chemistry Leading to Nanoscale Particles of Metals, Borides, and Metal Borates. Langmuir 1992, 8, 771-773.
(48) Glavee, G.; Klabunde, K.; Sorensen, C. M.; Hadjipanayis, G. C. Borohydride Reduction of Cobalt Ions in Water. Chemistry Leading to Nanoscale Metal, Boride, or Borate Particles. Langmuir 1993, 9, 162-169.
(49) Masa, J.; Weide, P.; Peeters, D.; Sinev, I.; Xia, W.; Sun, Z.; Somsen, C.; Muhler, M.; Schuhmann, W. Amorphous Cobalt Boride (Co2B) as a Highly Efficient Nonprecious Catalyst for Electrochemical Water Splitting: Oxygen and Hydrogen Evolution. Adv. Energy Mater. 2016, 6, 1502313.
(50) LaMer, V. K.; Dinegar, R. H. Theory, Production and Mechanism of Formation of Monodispersed Hydrosols. J. Am. Chem. Soc. 1950, 72, 4847-4854.
(51) Thanh, N. T. K.; Maclean, N.; Mahiddine, S. Mechanisms of Nucleation and Growth of Nanoparticles in Solution. Chem. Rev. 2014, 114, 7610-7630.
(52) Bartecki, A.; Taczaa, T. The Color of Transition Metal Compounds. I. Trichromaticity Colorimetry of Aqueous Solutions of Some Cr(III), Co(II), Ni(II) and Cu(II) Compounds. Spectrosc. Lett. 1990, 23, 727-739.
(53) Van Hyning, D. L.; Zukoski, C. F. Formation Mechanisms and Aggregation Behavior of Borohydride Reduced Silver Particles. Langmuir 1998, 14, 7034-7046.
(54) Van Hyning, D. L.; Klemperer, W. G.; Zukoski, C. F. Characterization of Colloidal Stability during Precipitation Reactions. Langmuir 2001, 17, 3120-3127.
(55) Van Hyning, D. L.; Klemperer, W. G.; Zukoski, C. F. Silver Nanoparticle Formation: Predictions and Verification of the Aggregative Growth Model. Langmuir 2001, 17, 3128-3135.
(56) Richards, V. N.; Rath, N. P.; Buhro, W. E. Pathway from a Molecular Precursor to Silver Nanoparticles: The Prominent Role of Aggregative Growth. Chem. Mater. 2010, 22, 3556-2567.
(57) Polte, J.; Erler, R.; Thunemann, A. F.; Sokolov, S.; Ahner, T. T.; Rademann, K.; Emmerling, F.; Kraehnert, R. Nucleation and Growth of Gold Nanoparticles Studied via In Situ Small Angle X-Ray Scattering at Millisecond Time Resolution. ACS Nano 2010, 4, 1076-1082.
(58) Polte, J.; Tuaev, X.; Wuithschick, M.; Fischer, A.; Thuenemann, A. F.; Rademann, K.; Kraehnert, R.; Emmerling, F. Formation Mechanism of Colloidal Silver Nanoparticles: Analogies and Differences to the Growth of Gold Nanoparticles. ACS Nano 2012, 6, 5791-5802.
(59) Wuithschick, M.; Paul, B.; Bienert, R.; Sarfraz, A.; Vainio, U.; Sztucki, M.; Kraehnert, R.; Strasser, P.; Rademann, K.; Emmerling, F.; Polte, J. Size-Controlled Synthesis of Colloidal Silver Nanoparticles Based on Mechanistic Understanding. Chem. Mater. 2013, 25, 4679-4689.
(60) Netskina, O. V.; Komova, O. V.; Simagina, V. I.; Odegova, G. V.; Prosvirin, I. P.; Bulavchenko, O. A. Aqueous-Alkaline NaBH4 solution: The Influence of Storage Duration of Solutions on Reduction and Activity of Cobalt Catalysts. Renew. Energy 2016, 99, 1073-1081.
(61) Tan, B. J.; Klabunde, K. J.; Sherwood, P. M. A. XPS Studies of Solvated Metal Atom Dispersed Catalysts. Evidence for Layered Cobalt-Manganese Particles on Alumina and Silica. J. Am. Chem. Soc. 1991, 113, 885-861.
(62) Mavel, G.; Escard, J. ESCA Surface Study of Metal Borides. Surf. Sci. 1973, 35, 109-116.
(63). Chen, Y. Z.; Wu, K. J. Hydrogenation Activity and Selectivity of Cobalt Borides. Appl. Catal. 1991, 78, 185-197.
(64) Masa, J.; Weide, P.; Peeters, D.; Sinev, I.; Xia, W.; Sun, Z.; Somsen, C.; Muhler, M.; Schuhmann, W. Amorphous Cobalt Boride (Co2B) as Highly Efficient Nonprecious Catalyst for Electrochemical Water Splitting: Oxygen and Hydrogen Evolution. Adv. Energy Mater. 2016, 6, 1502313.
(65) Bartkus, T. P.; T'ien, J. S.; Sung, C. A semi-global reaction rate model based on experimental data for the self-hydrolysis kinetics of aqueous sodium borohydride. Int. J. Hydrogen Energy 2013, 38, 4024-4033.
(66) Andrieux, J.; Demirci, U. B.; Hannauer, J.; Gervais, C.; Goutaudier, C.; Miele, P. Spontaneous Hydrolysis of Sodium Borohydride in Harsh Conditions. Int. J. Hydrogen Energy, 2011, 36, 224-233.
(67) Smith, W. Boron-11 NMR. J. Chem. Ed. 1977, 54, 469-473.
(68) Ogg, R. A. Nuclear Magnetic Resonance Spectra and Structure of Borohydride Ion and Diborane. J. Chem. Phys. 1954, 22, 1933-1935.

Notwithstanding the appended claims, the disclosure is also defined by the following clauses:

1. A method of producing cobalt-based nanoparticles ($Co_xB_y$ NPs) of a pre-selected diameter, comprising:
   nucleating $Co^{2+}$ ions with a sodium borohydride ($NaBH_4$) solution having a selected ratio of tetrahydroxyborate ($B(OH)_4^-$) to tetrahydroborate ($BH_4^-$) based on the pre-selected diameter, wherein the ratio of $B(OH)_4^-$ to $BH_4^-$ is positively correlated with the pre-selected diameter,
   to produce $Co_xB_y$ NPs of the pre-selected diameter.

2. The method according to Clause 1, wherein the pre-selected diameter is from about 10 to about 100 nm.

3. The method according to Clause 1 or Clause 2, wherein the nucleating comprises:
   combining:
      a cobalt salt comprising the $Co^{2+}$ ions;
      a capping agent; and
      the $NaBH_4$ solution having the selected ratio of $B(OH)_4^-$ to $BH_4^-$.

4. The method according to Clause 3, wherein the combining comprises:
   combining:
      a deaerated solution comprising the cobalt salt and the capping agent; and
      the $NaBH_4$ solution having the selected ratio of $B(OH)_4^-$ to $BH_4^-$.

5. The method according to Clause 3 or Clause 4, wherein the cobalt salt is selected from the group consisting of: cobalt chloride ($CoCl_2$), $CoBr_2$, $CoI_2$, $Co(NO_3)_2$, $Co(acac)_2$, Cobalt(II) acetate, and combinations thereof.

6. The method according to any one of Clauses 3 to 5, wherein the capping agent is selected from the group consisting of: a sodium salt of citrate, polyvinylpyrrolidone (PVP), polyethylene glycol (PEG), polyvinyl alcohol (PVA), polyethyleneimine (PEI), cetyltrimethyl ammonium bromide (CTA-Br), cetyltrimethyl ammonium chloride (CTA-Cl), and combinations thereof.

7. The method according to any one of Clauses 1 to 6, wherein the nucleating is performed in an anaerobic environment.

8. The method according to any one of Clauses 1 to 7, further comprising producing $Co_xB_y$ NPs of a different pre-selected diameter by:
nucleating $Co^{2+}$ ions with a sodium borohydride ($NaBH_4$) solution having a different selected ratio of tetrahydroxyborate ($B(OH)_4^-$) to tetrahydroborate ($BH_4^-$) based on the different pre-selected diameter, wherein the different ratio of $B(OH)_4^-$ to $BH_4^-$ is positively correlated with the different pre-selected diameter,
to produce $Co_xB_y$ NPs of the different pre-selected diameter.

9. The method according to any one of Clauses 1 to 8, further comprising, subsequent to producing the $Co_xB_y$ NPs, producing hollow metal nanospheres (HMNs) using the $Co_xB_y$ NPs as scaffolds.

10. The method according to Clause 9, wherein producing the HMNs comprises producing $Co_xB_y$ NP core/metal shell structures via a galvanic exchange reaction.

11. The method according to Clause 10, wherein the galvanic exchange reaction is performed in an anaerobic environment.

12. The method according to Clause 10 or Clause 11, wherein the galvanic exchange reaction comprises combining:
a solution comprising the $Co_xB_y$ NPs of the pre-selected diameter; and
a solution comprising a metal.

13. The method according to Clause 12, wherein the solution comprising the metal is deaerated prior to the combining with the solution comprising the $Co_xB_y$ NPs of the pre-selected diameter.

14. The method according to Clause 12 or Clause 13, comprising modulating the pH of the solution comprising the metal prior to the combining with the solution comprising the $Co_xB_y$ NPs of the pre-selected diameter.

15. The method according to Clause 14, wherein modulating the pH of the solution comprising the metal comprises increasing the pH of the solution comprising the metal.

16. The method according to any one of Clauses 10 to 15, wherein producing the HMNs comprises oxidizing the $Co_xB_y$ NP cores of the $Co_xB_y$ NP core/metal shell structures.

17. The method according to Clause 16, wherein the oxidizing is by oxygenation.

18. The method according to Clause 17, wherein the oxygenation is controlled oxygenation.

19. The method according to any one of Clauses 9 to 18, wherein the HMNs exhibit a surface plasmon resonance (SPR) absorption with a maximum peak position of from about 565 to about 850 nm.

20. The method according to any one of Clauses 9 to 19, wherein the HMNs are hollow gold nanospheres (HGNs).

21. The method according to any one of Clauses 9 to 20, further comprising, subsequent to producing the HMNs, attaching a targeting moiety to the surface thereof.

22. The method according to Clause 21, wherein the targeting moiety is selected from the group consisting of: an antibody, a ligand, an aptamer, a nucleic acid, and a small molecule.

23. The method according to Clause 21 or Clause 22, wherein the targeting moiety binds to a molecule on the surface of a target cell.

24. The method according to Clause 23, wherein the target cell is a cancer cell.

25. Cobalt-based nanoparticles ($Co_xB_y$ NPs) produced according to the methods of any one of Clauses 1 to 8.

26. A kit, comprising:
the $Co_xB_y$ NPs of Clause 25; and
instructions for using the $Co_xB_y$ NPs to produce hollow metal nanospheres (HMNs).

27. Hollow metal nanospheres (HMNs) produced according to the methods of any one of Clauses 9 to 24.

28. A composition comprising the HMNs of Clause 27.

29. A pharmaceutical composition, comprising:
the HMNs of Clause 27; and
a pharmaceutically acceptable carrier.

30. A kit, comprising:
the HMNs of Clause 27, the composition of Clause 28, or the pharmaceutical composition of Clause 29; and
instructions for using the HMNs to detect an analyte in vitro or in vivo.

31. A kit, comprising:
the HMNs of Clause 27, the composition of Clause 28, or the pharmaceutical composition of Clause 29; and
instructions for administering the HMNs to an individual in need thereof.

32. A method of producing cobalt-based nanoparticle ($Co_xB_y$ NP) core/metal shell structures, comprising:
combining in an anaerobic galvanic exchange reaction:
a deaerated solution comprising $Co_xB_y$ NP scaffolds; and
a deaerated solution comprising a metal,
to produce the $Co_xB_y$ NP core/metal shell structures.

33. The method according to Clause 32, comprising modulating the pH of the solution comprising the metal prior to the combining with the solution comprising the $Co_xB_y$ NP scaffolds.

34. The method according to Clause 33, wherein modulating the pH of the solution comprising the metal comprises increasing the pH of the solution comprising the metal.

35. The method according to any one of Clauses 32 to 34, further comprising producing hollow metal nanospheres (HMNs) from the $Co_xB_y$ NP core/metal shell structures.

36. The method according to Clause 35, wherein producing the HMNs comprises oxidizing the $Co_xB_y$ NP cores of the $Co_xB_y$ NP core/metal shell structures.

37. The method according to Clause 36, wherein the oxidizing is by oxygenation.

38. The method according to Clause 37, wherein the oxygenation is controlled oxygenation.

39. The method according to any one of Clauses 35 to 38, wherein the HMNs exhibit a surface plasmon resonance (SPR) absorption with a maximum peak position of from about 565 to about 850 nm.

40. The method according to any one of Clauses 35 to 39, wherein the HMNs are hollow gold nanospheres (HGNs).

41. The method according to any one of Clauses 35 to 40, further comprising, subsequent to producing the HMNs, attaching a targeting moiety to the surface thereof.

42. The method according to Clause 41, wherein the targeting moiety is selected from the group consisting of: an antibody, a ligand, an aptamer, a nucleic acid, and a small molecule.

43. The method according to Clause 41 or Clause 42, wherein the targeting moiety binds to a molecule on the surface of a target cell.

44. The method according to Clause 43, wherein the target cell is a cancer cell.

45. The method according to any one of Clauses 32 to 44, wherein the $Co_xB_y$ NP scaffolds are $Co_xB_y$ NPs produced according to the methods of any one of Clauses 1 to 8.

46. Hollow metal nanospheres (HMNs) produced according to the methods of any one of Clauses 35 to 45.

47. A composition comprising the HMNs of Clause 46.

48. A pharmaceutical composition, comprising:
the HMNs of Clause 46; and
a pharmaceutically acceptable carrier.

49. A kit, comprising:
the HMNs of Clause 46, the composition of Clause 47, or the pharmaceutical composition of Clause 48; and
instructions for using the HMNs to detect an analyte in vitro or in vivo.

50. A kit, comprising:
the HMNs of Clause 46, the composition of Clause 47, or the pharmaceutical composition of Clause 48; and
instructions for administering the HMNs to an individual in need thereof.

51. A method comprising administering to an individual in need thereof the HMNs of Clause 27 or Clause 46, or the pharmaceutical composition of Clause 29 or Clause 48.

52. The method according to Clause 51, wherein the individual in need thereof is in need of photothermal therapy (PTT).

53. The method according to Clause 51 or Clause 52, wherein the individual has a cell proliferative disorder.

54. The method according to Clause 53, wherein the cell proliferative disorder is cancer.

55. The method according to any one of Clauses 51 to 54, wherein the HMNs are targeted to cells of the cancer via a targeting moiety on the surface of the HMNs.

Accordingly, the preceding merely illustrates the principles of the present disclosure. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein.

What is claimed is:

1. A method of producing cobalt-based nanoparticles ($Co_xB_y$ NPs) of a pre-selected diameter, comprising:
(a) pre-selecting a desired diameter of $Co_xB_y$ NPs prior to production of the $Co_xB_y$ NPs;
(b) adding tetrahydroxyborate ($B(OH)_4^-$) to an initial sodium borohydride ($NaBH_4$) solution to produce a $NaBH_4$ solution having a selected ratio of $B(OH)_4^-$ to tetrahydroborate ($BH_4^-$), wherein the ratio is selected to achieve the pre-selected desired diameter of the $Co_xB_y$ NPs; and
(c) nucleating $Co^{2+}$ ions with the $NaBH_4$ solution having the selected ratio of $B(OH)_4^-$ to $BH_4^-$ to produce $Co_xB_y$ NPs of the pre-selected diameter, wherein the ratio of $B(OH)_4^-$ to $BH_4^-$ is known to be positively correlated with the pre-selected diameter during steps (a) and (b).

2. The method according to claim 1, wherein the pre-selected diameter is from about 10 to about 100 nm.

3. The method according to claim 1, wherein the nucleating comprises:
combining:
a cobalt salt comprising the $Co^{2+}$ ions, wherein the cobalt salt is selected from the group consisting of: cobalt chloride ($CoCl_2$), $CoBr_2$, $CoI_2$, $Co(NO_3)_2$, $Co(acac)_2$, Cobalt(II) acetate, and combinations thereof;
a capping agent; and
the $NaBH_4$ solution having the selected ratio of $B(OH)_4^-$ to $BH_4^-$.

4. The method according to claim 3, wherein the combining comprises:
combining:
a deaerated solution comprising the cobalt salt and the capping agent; and
the $NaBH_4$ solution having the selected ratio of $B(OH)_4^-$ to $BH_4^-$.

5. The method according to claim 3, wherein the capping agent is selected from the group consisting of: a sodium salt of citrate, polyvinylpyrrolidone (PVP), polyethylene glycol (PEG), polyvinyl alcohol (PVA), polyethyleneimine (PEI), cetyltrimethyl ammonium bromide (CTA-Br), cetyltrimethyl ammonium chloride (CTA-CI), and combinations thereof.

6. The method according to claim 1, wherein the nucleating is performed in an anaerobic environment.

7. The method according to claim 1, further comprising, subsequent to producing the $Co_xB_y$ NPs, producing hollow metal nanospheres (HMNs) using the $Co_xB_y$ NPs as scaffolds, wherein producing the HMNs comprises producing $Co_xB_y$ NP core/metal shell structures via a galvanic exchange reaction.

8. The method according to claim 7, wherein the galvanic exchange reaction comprises combining:
a solution comprising the $Co_xB_y$ NPs of the pre-selected diameter; and
a solution comprising a metal.

9. The method according to claim 8, wherein the solution comprising the metal is deaerated prior to the combining with the solution comprising the $Co_xB_y$ NPs of the pre-selected diameter.

10. The method according to claim 8, comprising increasing the pH of the solution comprising the metal prior to the combining with the solution comprising the $Co_xB_y$ NPs of the pre-selected diameter.

11. The method according to claim 7, wherein producing the HMNs comprises oxidizing the $Co_xB_y$ NP cores of the $Co_xB_y$ NP core/metal shell structures by controlled oxygenation.

12. The method according to claim 7, wherein the HMNs exhibit a surface plasmon resonance (SPR) absorption with a maximum peak position of from about 560 to about 1040 nm.

13. The method according to claim 7, wherein the HMNs are hollow gold nanospheres (HGNs).

14. The method according to claim 7, further comprising, subsequent to producing the HMNs, attaching a targeting moiety to the surface thereof.

15. A method of producing cobalt-based nanoparticle ($Co_xB_y$ NP) core/metal shell structures, comprising:
combining in an anaerobic galvanic exchange reaction:
a deaerated solution comprising $Co_xB_y$ NP scaffolds; and
a deaerated solution comprising a metal,
to produce the $Co_xB_y$ NP core/metal shell structures.

* * * * *